(12) United States Patent
Stamler

(10) Patent No.: US 11,931,339 B2
(45) Date of Patent: Mar. 19, 2024

(54) COMPOSITIONS AND METHODS FOR TREATING TISSUE INJURY

(71) Applicant: CASE WESTERN RESERVE UNIVERSITY, Cleveland, OH (US)

(72) Inventor: Jonathan S. Stamler, Cleveland, OH (US)

(73) Assignees: CASE WESTERN RESERVE UNIVERSITY, Cleveland, OH (US); UNIVERSITY HOSPITALS CLEVELAND MEDICAL CENTER, Cleveland, OH (US)

( * ) Notice: Subject to any disclaimer, the term of this patent is extended or adjusted under 35 U.S.C. 154(b) by 114 days.

(21) Appl. No.: 17/256,066

(22) PCT Filed: Jun. 25, 2019

(86) PCT No.: PCT/US2019/038982
§ 371 (c)(1),
(2) Date: Dec. 24, 2020

(87) PCT Pub. No.: WO2020/005938
PCT Pub. Date: Jan. 2, 2020

(65) Prior Publication Data
US 2021/0267943 A1     Sep. 2, 2021

Related U.S. Application Data

(60) Provisional application No. 62/689,416, filed on Jun. 25, 2018.

(51) Int. Cl.
*A61K 31/4166*     (2006.01)
*A61K 31/4178*     (2006.01)
(Continued)

(52) U.S. Cl.
CPC ...... *A61K 31/4166* (2013.01); *A61K 31/4178* (2013.01); *A61K 31/422* (2013.01);
(Continued)

(58) Field of Classification Search
CPC ....................... A61K 31/4166; A61K 31/4178
See application file for complete search history.

(56) References Cited

U.S. PATENT DOCUMENTS 2,683,718 A    7/1954   Dornfeld et al.
4,436,745 A    3/1984   York, Jr.
(Continued)

FOREIGN PATENT DOCUMENTS

EP    1961420 A1    8/2008
EP    1987829 A1    11/2008
(Continued)

OTHER PUBLICATIONS

Gottmann et al., Transplantation 2007 (vol. 84, Issue 6 pp. 755-762) (Year: 2007).*
(Continued)

*Primary Examiner* — Craig D Ricci
*Assistant Examiner* — Janet L Coppins
(74) *Attorney, Agent, or Firm* — TAROLLI, SUNDHEIM, COVELL & TUMMINO, LLP

(57) ABSTRACT

A method for preventing or treating a tissue injury and/or promoting tissue repair in a subject in need thereof, includes administering to the subject a therapeutically effective amount of an ADH inhibitor, AKR inhibitor, SCoR inhibitor, and/or PKM2 inhibitor.

12 Claims, 48 Drawing Sheets

(51) Int. Cl.
  A61K 31/422    (2006.01)
  A61K 31/424    (2006.01)
  A61K 31/4439   (2006.01)
  A61K 31/497    (2006.01)
  A61K 31/506    (2006.01)
  A61K 45/06     (2006.01)
(52) U.S. Cl.
  CPC ........ *A61K 31/424* (2013.01); *A61K 31/4439* (2013.01); *A61K 31/497* (2013.01); *A61K 31/506* (2013.01); *A61K 45/06* (2013.01)

(56)  References Cited

U.S. PATENT DOCUMENTS

| | | | |
|---|---|---|---|
| 5,153,211 | A | 10/1992 | York, Jr. |
| 7,674,795 | B2 | 3/2010 | Mailliet et al. |
| 10,117,842 | B2 | 11/2018 | Nagy |
| 10,537,557 | B2 | 1/2020 | Raffay et al. |
| 2010/0292178 | A1 | 11/2010 | Young |
| 2010/0305078 | A1 | 12/2010 | Schotzinger et al. |
| 2011/0092566 | A1 | 4/2011 | Srivastava et al. |
| 2012/0083501 | A1 | 4/2012 | Hunt et al. |
| 2012/0220001 | A1 | 8/2012 | Marlière |
| 2013/0196342 | A1 | 8/2013 | Stamler et al. |
| 2014/0206693 | A1 | 7/2014 | Srivastava et al. |
| 2017/0360755 | A1* | 12/2017 | Stamler ............... A61P 9/10 |

FOREIGN PATENT DOCUMENTS

| | | |
|---|---|---|
| JP | 58-140020 A | 8/1983 |
| JP | 2004315409 A | 11/2004 |
| JP | 2006510379 A | 3/2006 |
| WO | 2002/047680 A2 | 6/2002 |
| WO | 2004/110488 A1 | 12/2004 |
| WO | 2008/118370 A2 | 10/2008 |
| WO | 2010/104595 A1 | 9/2010 |
| WO | 2016090373 A1 | 6/2016 |

OTHER PUBLICATIONS

Chen and Zhang, Reviews in Pharmacology 2012, vol. 3 (Article 35), pp. 1-6. (Year: 2012).*
Meyler's Side Effects of Drugs (Sixteenth Edition), 2016, "Aldose Reductase Inhibitors," p. 1. (Year: 2016).*
Bhatti et al, Bioorganic Chemistry 75 (2017), pp. 62-70. (Year: 2017).*
Applicant: Case Western Reserve University; PCT International Application No. PCT/US19/52426, Filed: Sep. 23, 2019; PCT International Search Report and Written Opinion, Authorized Officer: Lee Young; Feb. 7, 2020; 9 pgs.
Barski et al. "Tho Aldo-Keto Reductase Superfamily and its Rult:, in Drug Metabolism and Detoxification" Drug Metabolism Reviews. Nov. 6, 2008 (Nov. 6, 2008), vol. 40, p. 553-624.

Fletcher, "What should my cholesterol level be at my age?" Medical News Today. Feb. 20, 2017 (Feb. 20, 2017) https://www.medicalnewstoday.com/articles/315900.php; p. 2, para 2.
Hwang et al. The FASEB Journal, Published online Dec. 2001, pp. 1-22.
International Search Report & Written Opinion for International Application No. PCT/US2015/064308.
Jonathan S. Stamler; "Compositions and Methods of Reducing Serum Cholesterol and PCSK9"; U.S. Appl. No. 16/648,737, filed Mar. 19, 2020; U.S. Non-Final Office Action dated Mar. 7, 2022; 11 pgs.
Malatkova, Pet al., "Human Carbonyl Reductases", Current Drug Metabolism, vol. 11, 2010, 24 pp. 639-658.
Morakinyo, MK et al., "Detailed mechanistic investigation into the Snitrosation of cystearnine", 26 Can. J. Chem. vol. 90, 2012, pp. 724-738.
Morris, SL et al., "Inhibition of Bacillus cereus Spore Outgrowth by Covalent Modification of a Sulfhydryl Group by Nitrosothiol and Iodoacetate", Journal of Bacteriology, vol. 148, No. 2, Nov. 1981, pp. 465-471.
Partial Supplementary European Search Report for Application No. 15864966.5-1112/3226859.
PubChem CID 20267156, create date, Dec. 5, 2007 p. 2 formula.
PubChem CID 20267160, create date, Dec. 5, 2007 p. 1 formula.
PubChem-CID-10335836, Create Date: Oct. 25, 2006; p. 2.
Puneet Anand et al., "Identification of S-nitroso-CoA reductases that regulate protein S-nitrosylation", Proceedings of the National Academy of Sciences, vol. 111, No. 52, Dec. 15, 2014, pp. 8572-18577.
Puneet Anand, "Purification and Characterization of Novel Denitrosylases from Yeast and Mammals", Dec. 31, 2012, pp. 1-156.
Roediger, Wew. Review article: nitric oxide from dysbiotic bacterial respiration of nitrate in the pathogenesis and as a target for therapy of ulcerative colitis"Ailment Pharmacol", Ther. vol. 27, 2008, pp. 531-541.
Soda, M et al., "Inhibition of Human Aldose Reductase-Like Protein (AKR1810) by alpha- and gamma-Mangostins, Major Components of Pericarps of Mangosteen", Biol. Pharm. Bull. Vol. 35, No. 11, 2012, pp. 2075-2080.
Supplemental European search report for application No. 15864966.5-1112/3226859, dated Nov. 30, 2018.
Suropean Search Report for application No. 15864966.5-1112/3226859.
Tao B et al: "Synthesis of Conformationally Constrained Spirohydantoins With a Dibenzoaa, Doheptadiene Ring", Synthesis, Georg Thieme Verlag, Stutigart, De, No. 10, Feb. 29, 2000, pp. 1449-1453.
Zhang, HH et al., "Estrogen-Responsive nitroso-Proteorne in Uterine Artery Endothelial Cells: Role of Endothelial Nitric Oxide Synthase and Estrogen Receptor-beta", J. Cell Physiol. vol. 227, No. 1, Jan. 2012, pp. 146-159.
Japanese Application No. 2020-516839; Japanese Office Action—Notice of Reasons for Rejection; Oct. 18, 2022; 15 pgs.
Kaukola, Sirkka, et al. "Effect of phenytoin on serum lipoproteins in middle-aged men." Journal of Cardiovascular Pharmacology 3.1 (1981): 207-214.

* cited by examiner c

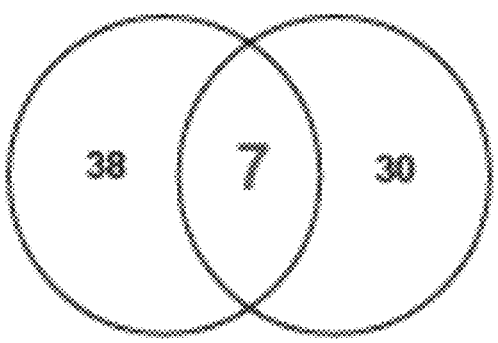

Fig. 2C d

| | | ID UniProt | | Description | Major GO term |
|---|---|---|---|---|---|
| 4 | 3 | Q91Y97 | Aldob | Fructose-bisphosphate aldolase B | Gluconeogenesis Glycolytic process |
| 5 | 23 | Q8BWT1 | Acaa2 | 3-ketoacyl-CoA thiolase | Lipid metabolic process Fatty acid beta-oxidation |
| 6 | 7 | Q05920 | Pcx | Pyruvate carboxylase | Gluconeogenesis Lipid metabolic process |
| 7 | 15 | P54071 | Idh2 | Isocitrate dehydrogenase 2 | Glyoxylate cycle Tricarboxylic acid cycle |
| 24 | 43 | P52480 | PKM2 | Isoform M2 of Pyruvate kinase isozymes | Glycolytic process Response to hypoxia |
| 31 | 8 | P10126 | Eef1a1 | Elongation factor 1 alpha 1 | tRNA binding Translation elongation factor |
| 35 | 11 | O88844 | Idh1 | Isocitrate dehydrogenase 1 | Glyoxylate cycle Tricarboxylic acid cycle |

Fig. 2D

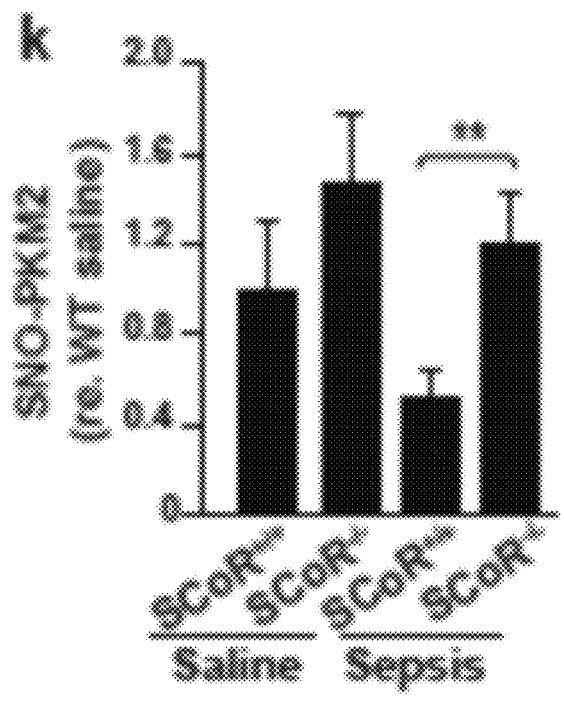
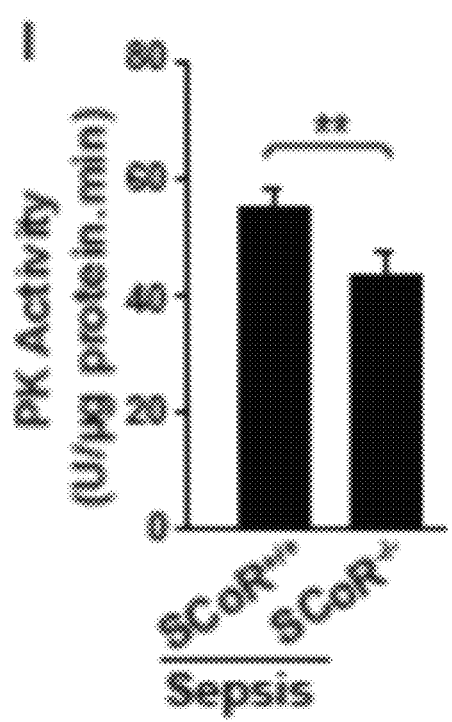
Fig. 7K
Fig. 7L
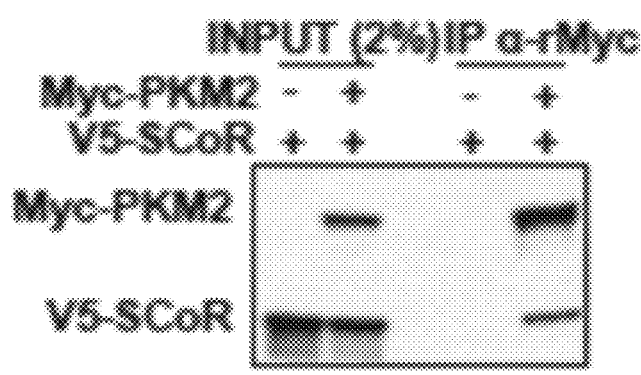
Fig. 8A a b

COMPOSITIONS AND METHODS FOR TREATING TISSUE INJURY

RELATED APPLICATION

This application claims priority from U.S. Provisional Application No. 62/689,416 filed Jun. 25, 2018, the subject matter of which is incorporated herein by reference in their entirety.

GOVERNMENT FUNDING

This invention was made with government support under Grant Nos. HL075443, HL128192, and HL126900 awarded by The National Institutes of Health. The United States government has certain rights to the invention.

BACKGROUND

The chemical compound nitric oxide is a gas with chemical formula NO. NO is one of the few gaseous signaling molecules known in biological systems, and plays an important role in controlling various biological events. For example, the endothelium uses NO to signal surrounding smooth muscle in the walls of arterioles to relax, resulting in vasodilation and increased blood flow to hypoxic tissues. NO is also involved in regulating smooth muscle proliferation, platelet function, and neurotransmission, and plays a role in host defense. Although NO is highly reactive and has a lifetime of a few seconds, it can both diffuse freely across membranes and bind to many molecular targets. These attributes make NO capable of controlling biological events between adjacent cells and within cells, but present problems with the ability to regulate its activity.

As free radical gas, NO is reactive and unstable, thus NO is short lived in vivo, having a half life of 3-5 seconds or less under physiologic conditions. In the presence of oxygen or metals, NO can combine with thiols to generate a biologically important class of stable NO adducts called S-nitrosothiols (SNO's). This stable pool of NO has been postulated to act as a regulated source of bioactive NO and as such appears to be important in health and disease, given the centrality of NO in cellular homeostasis (Stamler et al., Proc. Natl. Acad. Sci. USA, 89:7674-7677 (1992)). Protein SNO's play broad roles in the function of cardiovascular, respiratory, metabolic, gastrointestinal, immune, and central nervous system (Foster et al., Trends in Molecular Medicine, 9 (4):160-168, (2003)).

Acute kidney injury (AKI) is an important clinical problem associated with high rates of morbidity and mortality (1.7 million deaths annually). Considerable effort has been directed toward the development of preventive strategies for AKI using various agents and animal models. Despite advances in prevention strategies, no specific treatment for AKI has yet been developed.

The main causes of AKI are hypoxia and oxidative stress due to renal ischemic reperfusion injury (IRI). During periods of transient reduction in renal blood flow (RBF), an insufficient oxygen supply can cause energy impairment (ATP depletion) in the renal outer medulla, resulting in the injury and death of the tubular epithelial cells due to acute tubular necrosis (ATN) and apoptosis. The inflammation due to oxygen-free radicals after reperfusion leads to the extension phase of ischemic AKI. Resistance to hypoxia and the reduction of oxidative stress are treatment targets for ischemic AKI.

SUMMARY

Embodiments described herein relate to compositions and methods of modulating protein nitrosylation and particularly relates to the use of alcohol dehydrogenase (ADH) inhibitors (e.g., ADH6 inhibitors), aldoketo reductase (AKR) inhibitors (e.g., AKR1A1 inhibitors), SNO-Coenzyme A reductase (SCoR) inhibitors (e.g., ADH6 inhibitors and AKR1A1 inhibitors), and/or pyruvate kinase M2 (PKM2) inhibitors to prevent, treat, or reduce tissue injury and/or promote tissue repair as well as to use the of SNO-Coenzyme A (SNO-CoA) as a PKM2 inhibitor.

It was previously discovered that Co-enzymeA (CoA) serves as an endogenous source of SNOs through its conjugation with NO to form S-nitroso-CoA (SNO-CoA), and that S-nitrosylation of proteins by SNO-CoA is governed by its cognate denitrosylase, SNO-CoA reductase (SCoR). It was found that the SNO-CoA/SCoR system is highly expressed in renal proximal tubules where it transduces the activity of eNOS in reprogramming of intermediary metabolism, thereby protecting kidneys from acute kidney injury (AKI). It was further found that protection by the SNO-CoA/SCoR system is mediated by inhibitory S-nitrosylation of pyruvate kinase M2 (PKM2). S-nitrosylation of PKM2 by SNO-CoA forces glucose flux into the pentose phosphate pathway (PPP) to detoxify reactive oxygen species (ROS), alleviate oxidative stress, and protect against AKI. Moreover, PKM2 inhibition also increases serine synthesis, which serves as a precursor for lipids, proteins and nucleotides, and may be used to regenerate tissues following injury. Therefore, inhibition of SCoR and/or PKM2 can advantageously be used to treat injurious conditions and/or tissue injuries, including acute tissue injuries, such as AKI.

Accordingly, in some embodiments, compositions and methods of inhibiting SCoR and/or PKM2 can be used to prevent, treat, or reduce tissue injury and/or promote tissue repair and, more particularly, prevent, treat, or reduce the severity of renal ischemia reperfusion injury (IRI) or acute kidney injury (AKI).

In some embodiments, a composition that is used to prevent, treat, or reduce tissue injury and/or promote tissue repair in a subject in need thereof includes a therapeutically effective amount of an ADH inhibitor, AKR inhibitor, SCoR inhibitor, and/or PKM2 inhibitor.

In some embodiments, a therapeutically effective amount of an ADH inhibitor, AKR inhibitor, and/or SNO-CoAR inhibitor can be an amount(s) effective to promote S-nitrosylation of proteins in the subject, promote S-nitrosylation of PKM2, and/or inhibit formation of tetrameric PKM2.

In other embodiments, a therapeutically effective amount of a PKM2 inhibitor can be an amount effective to inhibit formation of tetrameric PKM2, shunt metabolic intermediates through the pentose phosphate pathway (PPP), and/or alleviate oxidative stress in the subject.

In some embodiments, the ADH inhibitor, AKR inhibitor, SCoR inhibitor, and/or PKM2 inhibitor can prevent or treat acute kidney injury (AKI) associated with renal ischemia reperfusion injury (IRI).

In other embodiments, the amount of ADH inhibitor, AKR inhibitor, SCoR inhibitor, and/or PKM2 inhibitor administered to the subject can be an amount effective to induce renal vasodilatation, enhance resistance to hypoxia, improve renal hemodynamics, decrease renal oxidative stress, reduce renal inflammation, and preserve renal function.

In other embodiments, the amount of ADH inhibitor, AKR inhibitor, SCoR inhibitor, and/or PKM2 inhibitor administered to the subject is an amount effective to reduce serum creatinine and/or blood urea nitrogen (BUN) levels in a subject.

In other embodiments, nicotinamide adenine dinucleotide (NADI and/or a NAD precursor can be administered in combination with the ADH inhibitor, AKR inhibitor, SCoR inhibitor. The NAD+ precursor can be selected from the group consisting of tryptophan, nicotinic acid, nicotinic acid riboside, nicotinamide riboside (NR), and nicotinamide.

In other embodiments, the ADH inhibitor, AKR inhibitor, SCoR inhibitor, and/or PKM2 inhibitor can be administered to the subject before an ischemia reperfusion injury and/or tissue injury. For example, the ADH inhibitor, AKR inhibitor, SCoR inhibitor, and/or PKM2 inhibitor can administered at a range of about 1 minute to about 72 hours before the ischemia reperfusion injury or tissue injury, about 10 minutes to about 48 hours before the ischemia reperfusion injury or tissue injury, or about 30 minutes to about 36 hours before the ischemia reperfusion injury or tissue injury.

In other embodiments, the ADH inhibitor, AKR inhibitor, SCoR inhibitor, and/or PKM2 inhibitor can be administered at a time selected from the group consisting of 2 hours, 8 hours, 24 hours, and 26 hours before the ischemia reperfusion injury or tissue injury.

In other embodiments, the ADH inhibitor, AKR inhibitor, SCoR inhibitor, and/or PKM2 inhibitor can be administered at a time selected from the group consisting of about at least about 30 minutes, 2 hours, 8 hours, 24 hours, or 48 hours after the ischemic reperfusion injury.

In some embodiments, the ischemia reperfusion injury (IRI) or tissue injury is associated with an organ transplant, such as a kidney transplant, in the subject.

In other embodiments, the ischemia reperfusion injury (IRI) or tissue injury is associated with cardiovascular surgery or sepsis.

In some embodiment, the AKR inhibitor is an AKR1A1 inhibitor. In other embodiments, the AKR1A1 inhibitor includes imirestat and analogues thereof.

In some embodiments, the PKM2 inhibitor can selectively inhibit PKM2 (relative to PKM1). Examples of PKM2 inhibitors include a polynucleotide complementary to all or part of a PKM2 gene (e.g., a PKM2-targeted shRNA, siRNA or miRNA) a small molecule inhibitor or a prodrug of such as small molecule inhibitor. Examples of small molecule PKM2 inhibitors include the compounds detailed herein and those disclosed in U.S. Pat. Pub. 2010/0099726, which is specifically incorporated herein by reference in their entirety.

DETAILED DESCRIPTION

Figure 1:
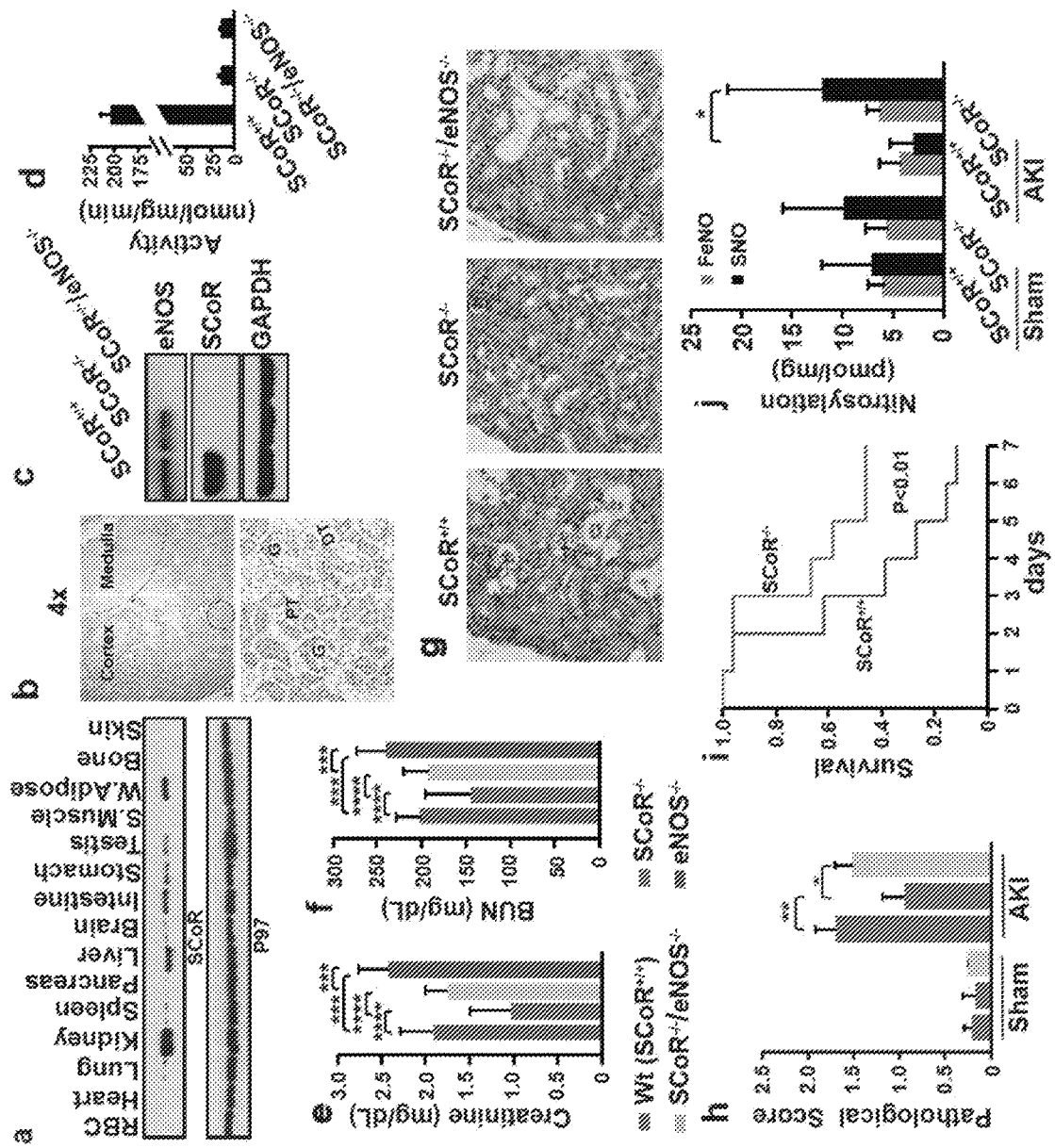
FIGS. 1(a-j) illustrates plots and images showing knockout of SCoR protects against AKI in a NO-dependent manner (a) Expression of SCoR in fifteen different mouse tissues. AAA ATPase P97 is used as loading control. (b) Expression of SCoR in proximal tubule (PT). Immunostaining: 20× image derives from circle area (4×). DT, distal tubule; G, glomerulus. (c) Expression of SCoR and eNOS in the kidney of wild-type control (SCoR$^{+/+}$), SCoR$^{-/-}$ and SCoR$^{-/-}$/eNOS$^{-/-}$ mice. (d) NADPH-dependent SNO-CoA metabolizing activity was measured in kidney extracts from SCoR$^{+/+}$, SCoR$^{-/-}$ and SCoR$^{-/-}$/eNOS$^{-/-}$ mice (n=6 mice per group). (e-f) Serum creatinine and blood urea nitrogen (BUN) in AKI-operated SCoR$^{+/+}$, SCoR$^{-/-}$, SCoR$^{-/-}$ eNOS$^{-/-}$ and eNOS$^{-/-}$ mice. (SCoR$^{+/+}$ and SCoR$^{-/-}$: >30 mice per group; SCoR$^{-/-}$/eNOS$^{-/-}$: 13 mice; eNOS$^{-/-}$: 10 mice). AKI induced by I/R. (g) H&E stain for tubular injury in sham-treated and AKI-damaged kidneys. Renal tubular injury includes severe tubular lysis (black arrow), loss of brush borders (green arrow) and sloughed debris in the tubular lumen (red arrow). (h) Pathological scores of tubular injury among SCoR$^{+/+}$, SCoR$^{-/-}$ and SCoR$^{-/-}$/eNOS$^{-/-}$ mice (n=5 mice per group). (i) Survival curve following I/R-induced AKI (n=24-26 mice for SCoR$^{+/+}$ and SCoR$^{-/-}$). Survival was analyzed by Kaplan-Meier estimation using the SAS program. P=0.0026 for the Wilcoxon test. (j) Endogenous SNO-protein levels and iron nitrosyl (FeNO) levels were quantified in sham- or AKI-kidney extracts by mercury-coupled photolysis-chemiluminescence (n=6 mice per group). Results are presented as mean±SD. One-way ANOVA with Tukey post hoc was used to detect significance in FIGS. 1e, 1f, 1h and 1j. P<0.05, P<0.01, *P<0.001, and ****P<0.0001.

While the following terms are believed to be well understood by one of ordinary skill in the art, the following definitions are set forth to facilitate explanation of the presently disclosed subject matter.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

The term "pharmaceutically acceptable salts" include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods. The term "pharmaceutically acceptable salts" also includes those obtained by reacting the active compound functioning as an acid, with an inorganic or organic base to form a salt, for example salts of ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, and the like. Non limiting examples of inorganic or metal salts include lithium, sodium, calcium, potassium, magnesium salts and the like.

Additionally, the salts of the compounds described herein, can exist in either hydrated or unhydrated (the anhydrous) form or as solvates with other solvent molecules. Non-limiting examples of hydrates include monohydrates, dihydrates, etc. Nonlimiting examples of solvates include ethanol solvates, acetone solvates, etc.

The term "solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds and salts described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The terms below, as used herein, have the following meanings, unless indicated otherwise:

"Amino" refers to the —$NH_2$ radical.

"Cyano" refers to the —CN radical.

"Halo" or "halogen" refers to bromo, chloro, fluoro or iodo radical.

"Hydroxy" or "hydroxyl" refers to the —OH radical.

"Imino" refers to the =NH substituent.

"Nitro" refers to the —$NO_2$ radical.

"Oxo" refers to the =O substituent.

"Thioxo" refers to the =S substituent.

"Alkyl" or "alkyl group" refers to a fully saturated, straight or branched hydrocarbon chain radical having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and Cm alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to a straight or branched divalent hydrocarbon chain radical, having from two to twelve carbon atoms, and having one or more carbon-carbon double bonds. Non-limiting examples of $C_2$-$C_{12}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" refers to a radical of the formula —$OR_a$ where $R_a$ is an alkyl, alkenyl or alknyl radical as defined above containing one to twelve carbon atoms. Unless stated otherwise specifically in the specification, an alkoxy group can be optionally substituted.

"Alkylamino" refers to a radical of the formula —$NHR_a$ or —$NR_aR_a$ where each $R_a$ is, independently, an alkyl, alkenyl or alkynyl radical as defined above containing one to twelve carbon atoms. Unless stated otherwise specifically in the specification, an alkylamino group can be optionally substituted.

"Alkylcarbonyl" refers to the $C(=O)R_a$ moiety, wherein $R_a$ is an alkyl, alkenyl or alkynyl radical as defined above.

A non-limiting example of an alkyl carbonyl is the methyl carbonyl ("acetal") moiety. Alkylcarbonyl groups can also be referred to as "$C_W$-$C_Z$ acyl" where w and z depicts the range of the number of carbon in $R_a$, as defined above. For example, "$C_1$-$C_{10}$ acyl" refers to alkylcarbonyl group as defined above, where $R_a$ is $C_1$-$C_{10}$ alkyl, $C_2$-$C_{10}$ alkenyl, or $C_2$-$C_{10}$ alkynyl radical as defined above. Unless stated otherwise specifically in the specification, an alkyl carbonyl group can be optionally substituted.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from phenyl (benzene), aceanthrylene, acenaphthylene, acephenanthrylene, anthracene, azulene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aralkyl" or "arylalkyl" refers to a radical of the formula —$R_b$—$R_c$ where $R_b$ is an alkylene group as defined above and $R_c$ is one or more aryl radicals as defined above. Aralkyl radicals include, but are not limited to, benzyl, diphenylmethyl and the like. Unless stated otherwise specifically in the specification, an aralkyl group can be optionally substituted.

"Aralkenyl" or "arylalkenyl" refers to a radical of the formula —$R_b$—$R_c$ where $R_b$ is an alkenylene group as defined above and $R_c$ is one or more aryl radicals as defined above. Unless stated otherwise specifically in the specification, an aralkenyl group can be optionally substituted.

"Aralkynyl" or "arylalkynyl" refers to a radical of the formula —$R_b$—$R_c$ where $R_b$ is an alkynylene group as defined above and $R_c$ is one or more aryl radicals as defined above. Unless stated otherwise specifically in the specification, an aralkynyl group can be optionally substituted.

"Carbocyclyl," "carbocyclic ring" or "carbocycle" refers to a ring structure, wherein the atoms which form the ring are each carbon. Carbocyclic rings can comprise from 3 to 20 carbon atoms in the ring. Carbocyclic rings include aryls and cycloalkyl. Cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused, bridged, or spiral ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused, bridged, or spiral ring systems, having from three to twenty carbon atoms, preferably having from three to ten carbon atoms, and which is attached to the rest of the molecule by a single bond. Monocyclic cycloalkenyl radicals include, for example, cyclopentenyl, cyclohexenyl, cycloheptenyl, cyclooctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused, bridged, or spiral ring systems, having from three to twenty carbon atoms, preferably having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Cycloalkylalkyl" refers to a radical of the formula —$R_b$—$R_d$ where $R_b$ is an alkylene, alkenylene, or alkynylene group as defined above and $R_d$ is a cycloalkyl, cycloalkenyl, cycloalkynyl radical as defined above. Unless stated otherwise specifically in the specification, a cycloalkylalkyl group can be optionally substituted.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Haloalkenyl" refers to an alkenyl radical, as defined above, that is substituted by one or more halo radicals, as defined above, e.g., 1-fluoropropenyl, 1,1-difluorobutenyl, and the like. Unless stated otherwise specifically in the specification, a haloalkenyl group can be optionally substituted.

"Haloalkynyl" refers to an alkynyl radical, as defined above, that is substituted by one or more halo radicals, as defined above, e.g., 1-fluoropropynyl, 1-fluorobutynyl, and the like. Unless stated otherwise specifically in the specification, a haloalkynyl group can be optionally substituted.

"Heterocyclyl," "heterocyclic ring" or "heterocycle" refers to a stable 3- to 20-membered non-aromatic, partially aromatic, or aromatic ring radical which consists of two to twelve carbon atoms and from one to six heteroatoms selected from the group consisting of nitrogen, oxygen and sulfur. Heterocyclycl or heterocyclic rings include heteroaryls as defined below. Unless stated otherwise specifically in the specification, the heterocyclyl radical can be a monocyclic, bicyclic, tricyclic or tetracyclic ring system, which can include fused, bridged, and spiral ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, aziridinyl, oextanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, pyridine-one, and the like. The point of attachment of the heterocyclyl, heterocyclic ring, or heterocycle to the rest of the molecule by a single bond is through a ring member atom, which can be carbon or nitrogen. Unless stated otherwise specifically in the specification, a heterocyclyl group can be optionally substituted.

"Heterocyclylalkyl" refers to a radical of the formula —$R_b$—$R_c$ where $R_b$ is an alkylene group as defined above and $R_c$ is a heterocyclyl radical as defined above. Unless stated otherwise specifically in the specification, a heterocyclylalkyl group can be optionally substituted.

"Heterocyclylalkenyl" refers to a radical of the formula —$R_b$—$R_c$ where $R_b$ is an alkenylene group as defined above and $R_c$ is a heterocyclyl radical as defined above. Unless stated otherwise specifically in the specification, a heterocyclylalkenyl group can be optionally substituted.

"Heterocyclylalkynyl" refers to a radical of the formula —$R_b$—$R_c$ where $R_b$ is an alkynylene group as defined above and $R_c$ is a heterocyclyl radical as defined above. Unless stated otherwise specifically in the specification, a heterocyclylalkynyl group can be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group can be optionally substituted.

"Heteroaryl" refers to a 5- to 20-membered ring system radical one to thirteen carbon atoms and one to six heteroatoms selected from the group consisting of nitrogen, oxygen and sulfur, as the ring member. For purposes of this invention, the heteroaryl radical can be a monocyclic, bicyclic, tricyclic or tetracyclic ring system, which can include fused or bridged ring systems, wherein at least one ring containing a heteroatom ring member is aromatic. The nitrogen, carbon or sulfur atoms in the heteroaryl radical can be optionally oxidized and the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, pyrazolopyridine, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

"Heteroarylalkyl" refers to a radical of the formula —$R_b$—$R_f$ where $R_b$ is an alkylene chain as defined above and $R_f$ is a heteroaryl radical as defined above. Unless stated otherwise specifically in the specification, a heteroarylalkyl group can be optionally substituted.

"Heteroarylalkenyl" refers to a radical of the formula —$R_b$—$R_f$ where $R_b$ is an alkenylene, chain as defined above and $R_f$ is a heteroaryl radical as defined above. Unless stated otherwise specifically in the specification, a heteroarylalkenyl group can be optionally substituted.

"Heteroarylalkynyl" refers to a radical of the formula —$R_b$—$R_f$ where $R_b$ is an alkynylene chain as defined above and $R_f$ is a heteroaryl radical as defined above. Unless stated otherwise specifically in the specification, a heteroarylalkynyl group can be optionally substituted.

"Thioalkyl" refers to a radical of the formula —$SR_a$ where $R_a$ is an alkyl, alkenyl, or alkynyl radical as defined above containing one to twelve carbon atoms. Unless stated otherwise specifically in the specification, a thioalkyl group can be optionally substituted.

The term "substituted" used herein means any of the above groups (e.g., alkyl, alkylene, alkenyl, alkenylene, alkynyl, alkynylene, alkoxy, alkylamino, alkylcarbonyl, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl, heteroarylalkyl, heteroarylalkenyl, heteroarylalkynyl, etc) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)ORh$, —$NR_gSO_2R_h$, —$OC(=O)NR_g R_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the symbol "  " (hereinafter can be referred to as "a point of attachment bond") denotes a bond that is a point of attachment between two chemical entities, one of which is depicted as being attached to the point of attachment bond and the other of which is not depicted as being attached to the point of attachment bond.

For example, "  " indicates that the chemical entity "A" is bonded to another chemical entity via the point of attachment bond. Furthermore, the specific point of attachment to the non-depicted chemical entity can be specified by inference. For example, the compound

wherein X is " 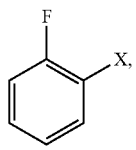 " infers that the point of attachment bond is the bond by which X is depicted as being attached to the phenyl ring at the ortho position relative to fluorine.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

All percentages and ratios used herein, unless otherwise indicated, are by weight.

The terms "gene expression" or "protein expression" includes any information pertaining to the amount of gene transcript or protein present in a sample, as well as information about the rate at which genes or proteins are produced or are accumulating or being degraded (e.g., reporter gene data, data from nuclear runoff experiments, pulse-chase data etc.). Certain kinds of data might be viewed as relating to both gene and protein expression. For example, protein levels in a cell are reflective of the level of protein as well as the level of transcription, and such data is intended to be included by the phrase "gene or protein expression information". Such information may be given in the form of amounts per cell, amounts relative to a control gene or protein, in unitless measures, etc.; the term "information" is not to be limited to any particular means of representation and is intended to mean any representation that provides relevant information. The term "expression levels" refers to a quantity reflected in or derivable from the gene or protein expression data, whether the data is directed to gene transcript accumulation or protein accumulation or protein synthesis rates, etc.

The terms "healthy" and "normal" are used interchangeably herein to refer to a subject or particular cell or tissue that is devoid (at least to the limit of detection) of a disease condition.

The term "nucleic acid" refers to polynucleotides such as deoxyribonucleic acid (DNA), and, where appropriate, ribonucleic acid (RNA). The term should also be understood to include analogues of either RNA or DNA made from nucleotide analogues, and, as applicable to the embodiment being described, single-stranded (such as sense or antisense) and double-stranded polynucleotides. In some embodiments, "nucleic acid" refers to inhibitory nucleic acids. Some categories of inhibitory nucleic acid compounds include antisense nucleic acids, RNAi constructs, and catalytic nucleic acid constructs. Such categories of nucleic acids are well-known in the art.

Embodiments described herein relate to compositions and methods of modulating protein nitrosylation and particularly relates to the use of alcohol dehydrogenase (ADH) inhibitors (e.g., ADH6 inhibitors), aldoketo reductase (AKR) inhibitors (e.g., AKR1A1 inhibitors), SNO-Coenzyme A reductase (SCoR) inhibitors (e.g., ADH6 inhibitors and AKR1A1 inhibitors), and/or pyruvate kinase M2 (PKM2) inhibitors to prevent, treat, or reduce tissue injury and/or promote tissue repair as well as to use the of SNO-Coenzyme A (SNO-CoA) as a PKM2 inhibitor.

It was previously discovered that Co-enzymeA (CoA) serves as an endogenous source of SNOs through its conjugation with NO to form S-nitroso-CoA (SNO-CoA), and that S-nitrosylation of proteins by SNO-CoA is governed by its cognate denitrosylase, SNO-CoA reductase (SCoR). It was found that the SNO-CoA/SCoR system is highly expressed in renal proximal tubules where it transduces the activity of eNOS in reprogramming of intermediary metabolism, thereby protecting kidneys from acute kidney injury (AKI). It was further found that protection by the SNO-CoA/SCoR system is mediated by inhibitory S-nitrosylation of pyruvate kinase M2 (PKM2). S-nitrosylation of PKM2 by SNO-CoA forces glucose flux into the pentose phosphate pathway (PPP) to detoxify reactive oxygen species (ROS), alleviate oxidative stress, and protect against AKI. Moreover, PKM2 inhibition also increases serine synthesis, which serves as a precursor for lipids, proteins and nucleotides, and may be used to regenerate tissues following injury.

Administration of ADH inhibitors, AKR inhibitors, SCoR inhibitors, and/or PKM2 inhibitors as well as SNO-CoA (or derivatives thereof, e.g., SNO-cysteamine) to a subject in need thereof can raise SNO levels and/or inhibit PKM2 activity in the subject to prevent, treat, or reduce tissue injury and/or promote tissue repair and, more particularly, prevent, treat, or reduce the severity of ischemia reperfusion injury (IRI) or acute tissue injury.

In some embodiments, a composition that is used to prevent, treat, or reduce tissue injury and/or promote tissue repair in a subject in need thereof includes a therapeutically effective amount of an ADH inhibitor, AKR inhibitor, SCoR inhibitor, and/or PKM2 inhibitor.

In some embodiments, a therapeutically effective amount of an ADH inhibitor, AKR inhibitor, and/or SCoR inhibitor can be an amount(s) effective to promote S-nitrosylation of proteins in the subject, promote S-nitrosylation of PKM2, and/or inhibit formation of tetrameric PKM2.

In other embodiments, a therapeutically effective amount of a PKM2 inhibitor can be an amount effective to inhibit formation of tetrameric PKM2, shunt metabolic intermediates through the pentose phosphate pathway (PPP), and/or alleviate oxidative stress in the subject.

A subject having a tissue injury described herein can include those having one or more of: myocardial injury, brain injury, spinal cord injury, muscular injury, skeletal injury, acute tubular necrosis, bowel injury, lung injury, liver injury, kidney injury, bone injury, skin injury, hernia repair, vascular anastomoses, atherosclerotic plaque, hemangioma, and/or traumatic injury.

In some embodiments, the tissue injury can be renal ischemia reperfusion injury (IRI) or acute kidney injury (AKI).

In certain embodiments, the subject has been identified as having AKI based on the Acute Kidney Injury Network (AKIN) criteria or Risk/Injury/Failure/Loss/ESRD (RIFLE) criteria.

In another embodiment, the subject has been identified as having an elevated level of serum creatinine, plasma creatinine, urine creatinine, or blood urea nitrogen (BUN), compared to a healthy control subject.

In another embodiment, the subject has been identified as having an elevated level of serum or urine neutrophil gelatinase-associated lipocalin, serum or urine interleukin-18, serum or urine cystatin C, or urine MM-1, compared to a healthy control subject.

In some embodiments, the acute kidney injury is an ischemic acute kidney injury. In one embodiment, the subject is a human who has been identified as having reduced effective arterial volume. In one embodiment, the subject has been identified as having intravascular volume depletion (e.g., due to hemorrhage, gastrointestinal loss, renal loss, skin and mucous membrane loss, nephrotic syndrome, cirrhosis, or capillary leak). In one embodiment, the subject has been identified as having reduced cardiac output (e.g., due to cardiogenic shock, pericardial disease, congestive heart failure, valvular heart disease, pulmonary disease, or sepsis). In one embodiment, the subject has been identified as having systemic vasodilation (e.g., caused by cirrhosis, anaphylaxis, or sepsis). In one embodiment, the subject has been identified as having renal vasoconstriction (e.g., caused by early sepsis, hepatorenal syndrome, acute hypercalcemia, a drug, or a radiocontrast agent).

In some embodiments, the acute kidney injury is a nephrotoxic acute kidney injury. In one embodiment, the human subject has been exposed to a nephrotoxin. For example, the nephrotoxin can be a nephrotoxic drug selected from the group consisting of an antibiotic (e.g., an aminoglycoside), a chemotherapeutic agent (e.g., cis-platinum), a calcineurin inhibitor, amphotericin B, and a radiographic contrast agent. In another example, the nephrotoxin can be an illicit drug or a heavy metal.

In certain embodiments, the subject has undergone a trauma injury or a crush injury.

In certain embodiments, the subject will undergo or has undergone an organ transplant surgery (e.g., a kidney transplant surgery or heart transplant surgery).

In certain embodiments, the subject will undergo or has undergone a surgery complicated by hypoperfusion.

In certain embodiments, the subject will undergo or has undergone cardiothoracic surgery or a vascular surgery.

In certain embodiments, the subject will be taking or has taken medication (e.g., an anticholinergic) that interferes with normal emptying of the bladder.

In certain embodiments, the subject has benign prostatic hypertrophy or a cancer (e.g., prostate cancer, ovarian cancer, or colorectal cancer).

In certain embodiments, the subject has a kidney stone.

In certain embodiments, the subject has an obstructed urinary catheter.

In certain embodiments, the subject has taken a drug that causes or leads to crystalluria, a drug that causes or leads to myoglobinuria, or a drug that causes or leads to cystitis.

Other embodiments, described herein relate to a method for protecting a kidney from injury in a subject. The method involves administering to the subject an effective amount of an ADH inhibitor, AKR inhibitor, SCoR inhibitor, and/or PKM2 inhibitor to protect the subject's kidney from injury. In some embodiments, the subject has been or will be exposed to an ischemic or nephrotoxic insult. In some embodiments, the human subject has been exposed to oxidative damage (e.g., by free radicals, such as reactive oxygen or nitrogen species).

Still further embodiments relate to a method for protecting a human subject's kidney from acute kidney injury during transplantation. The method involves administering to the subject an effective amount of an ADH inhibitor, AKR inhibitor, SCoR inhibitor, and/or PKM2 inhibitor to protect the subject's kidney from injury. In certain embodiments, the method further comprises administering to the human subject one or more doses of an ADH inhibitor, AKR inhibitor, SCoR inhibitor, and/or PKM2 inhibitor before and/or after (e.g., 0.1, 0.2, 0.3, 0.4, 0.5, 1, 2, 3, 4, 5, 6, 7, 8, 9, 10, 11, 12, 24, 48, 72, 96, 168 hours, or 1 week, 2 weeks, 3 weeks or 1 month) the organ transplantation.

Agents tested as an ADH inhibitor, AKR inhibitor, SCoR inhibitor, and/or PKM2 inhibitor can be any small chemical molecule or compound. Typically, test compounds will be small chemical molecules, natural products, or peptides. The assays are designed to screen large chemical libraries by automating the assay steps and providing compounds from any convenient source to assays, which are typically run in parallel (e.g., in microtiter formats on microtiter plates in robotic assays).

In some embodiments, the AKR inhibitor administered to a subject can be a partially selective AKR1A1 inhibitor and/or partially selective AKR1B1 inhibitor. For example, the AKR inhibitor can inhibit both AKR1A1 and AKR1B1, inhibit AKR1B1 at a lower $IC_{50}$ than AKR1A1, or inhibit AKR1A1 at a lower $IC_{50}$ than AKR1B1. Optionally, a selective or partially selective AKR1A1 inhibitor can be administered in combination with a selective or partially selective AKR1B1 inhibitor.

In some embodiments, the AKR1A1 inhibitor can have an $IC_{50} \leq 5$ µM, $\leq 1$ µM, or $\leq 100$ nM. In other embodiments, the AKR1A1 inhibitor can have a selectivity for AKR1A1 versus AKR1B1 $\geq 2$ times, $\geq 5$ times, $\geq 10$ times, $\geq 20$ times, $\geq 30$ times, $\geq 40$ times, $\geq 50$ times or more times. In other embodiments, the AKR1A1 inhibitor can have a selectivity for AKR1A1 versus other AKRs $\geq 2$ times, $\geq 5$ times, $\geq 10$ times, $\geq 20$ times, $\geq 30$ times, $\geq 40$ times, $\geq 50$ times or more times. In still other embodiments, the AKR1A1 inhibitor can have an AKR1A1 $IC_{50} \leq 400$ nM, $\leq 300$ nM, $\leq 200$ nM, $\leq 100$ nM, $\leq 50$ nM, or $\leq 25$ nM and a combined AKR1B1 and AKR1A1 $IC_{50} \leq 500$ nM, $\leq 400$ nM, $\leq 300$ nM, $\leq 200$ nM (e.g., less than 100 nM).

In some embodiments, the selectivity of the AKR inhibitor for AKR1A1 inhibition versus other AKRs, such as AKR1B1, can be measured using SCoR as a substrate. In this instance where SCoR is used as a substrate to measure AKR activity, the AKR inhibitor can have a selectivity for AKR1A1 versus AKR1B1 of $\geq 2$ times, $\geq 5$ times, $\geq 10$ times, $\geq 20$ times, $\geq 30$ times, $\geq 40$ times, $\geq 50$ times or more. In some embodiments, the AKR inhibitor can have neglible inhibition of AKR1B1 activity of SNO-CoA, and particularly compared to AKR1A1 activity.

In other embodiments, the AKR1B1 inhibitor can have an $IC_{50} \leq 5$ µM, $\leq 1$ µM, or $\leq 100$ nM. In other embodiments, the AKR1B1 inhibitor can have a selectivity for AKR1B1 versus AKR1A1 $\geq 2$ times, $\geq 5$ times, $\geq 10$ times, $\geq 20$ times, $\geq 30$ times, $\geq 40$ times, $\geq 50$ times or more times. In other embodiments, the AKR1B1 inhibitor can have a selectivity for AKR1B1 versus other AKRs $\geq 50$ times. In still other embodiments, the AKR1B1 inhibitor can have an AKR1B1 $IC_{50} \leq 300$ nM, $\leq 200$ nM, $\leq 100$ nM, $\leq 50$ nM, or $\leq 25$ nM and a combined AKR1B1 and AKR1A1 $IC_{50} \leq 500$ nM, $\leq 400$ nM, $\leq 300$ nM, $\leq 200$ nM (e.g., less than 100 nM).

Examples of selective and partially selective AKR1A1 inhibitors, including partially selective inhibitors of AKR1A1 activity of SCoR, can include Imirestat (2,7-Difluoro-2'H,5'H-spirolfluorene-9,4'-imidazolidinel-2',5'-dione) and analogues thereof. Other examples of selective and partially selective AKR1A1 inhibitors can include Tolrestat, Oxo-Tolrestat, Epalrestat, Fidarestat, Statil, Sorbinil, Ranirestat, and Minalrestat.

In some embodiments, the imirestat analogues can include compounds selected from the group consisting of:

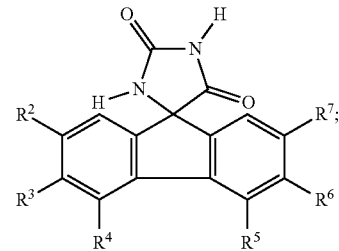

-continued
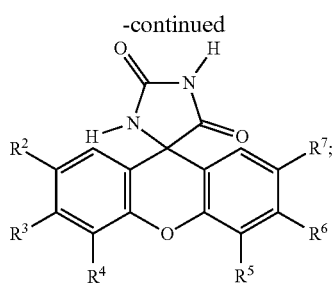
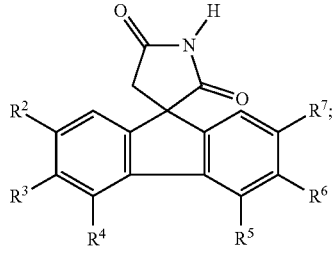
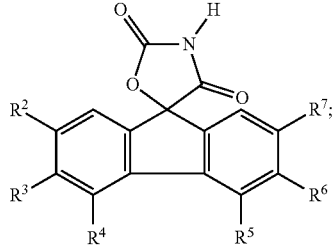
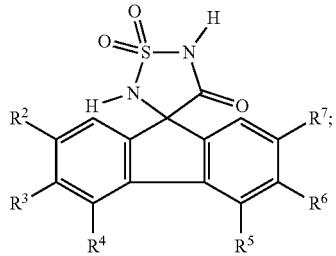
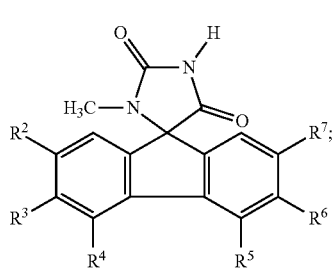
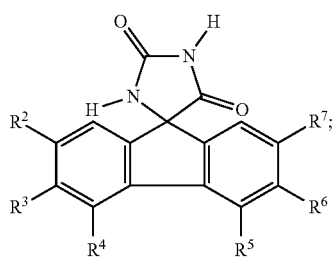
-continued
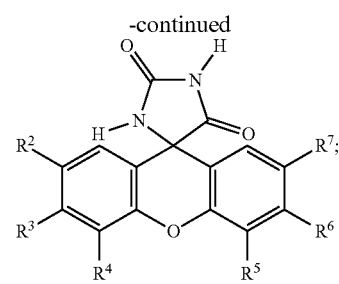
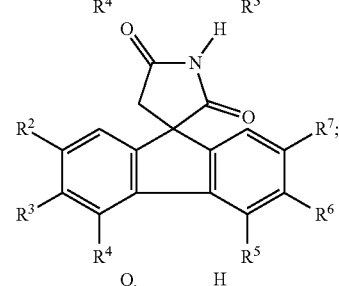
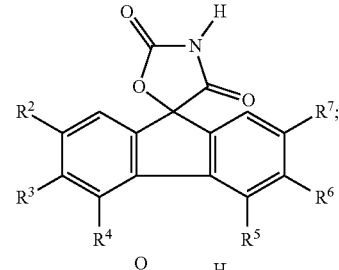
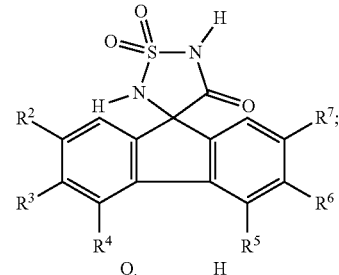
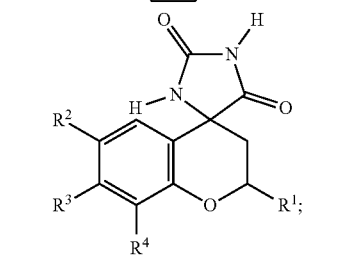

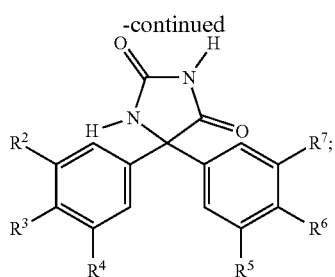

wherein IV, $R^2$, $R^3$, $R^4$, $R^5$, $R^6$, and $R^7$ are the same or different and are independently selected from the group consisting of hydrogen, halogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), carbamido (—NH—(CO)—NH$_2$), cyano (—CN), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO$_2$NR$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide, and combinations thereof; and pharmaceutically acceptable salts thereof.

In other embodiments, $R^1$, $R^2$, $R^3$, $R^4$, $R^5$, $R^6$, and $R^7$ are the same or different and are independently selected from the group consisting of hydrogen, halogen, alkyl, haloalkyl, cycloalkyl, heterocyclyl, heteroaryl, —OH, carboxyl, alkylene carboxyl, alkylene cycloalkyl, alkylene heterocyclyl, alkylene heteroaryl, alkylene-C(O)N(R$^8$)$_m$, —O-alkylene-carboxyl, —O-arylene-carboxyl, —O-alkylene-arylene, —O-alkylene-heteroaryl, —O-alkylene-heterocyclyl, carboxyl, alkyne carboxyl, —O-alkylene-N(R$^8$)$_2$, —N(R$^8$)$_2$, —N(R$^8$)(alkylene-OH), —C(O)N(R$^8$)$_m$, —C(O)N(R$^8$)(alkylene-OH), —C(O)N(R$^8$)(alkylene car-boxyl), —C(O)N(R$^8$)S(O)$_m$-alkyl, —C(O)-alkyl, —C(O)O-alkyl, alkoxy, or —S(O)$_m$-alkyl;

each R$^8$ is independently, H, alkyl, -alkylene-OH optionally substituted with —OH, -alkylene-NH$_2$, -alkylene-N(R$^9$)$_2$, -alkylene-O-alkylene-OH, -alkylene-O-alkylene-NH$_2$, —C(O)-alkyl, —C(O)O-alkyl, -alkylene-COOH, or —S(O)$_m$-alkyl;

or alternatively, two R$^8$ together with the N atom to which they are attached can form a 4- to 7-membered heterocycle, optionally containing an additional heteroatom selected from O, S, or N, and wherein the heterocycle is optionally substituted with R$^9$; and R$^9$ is halogen, alkyl, or alkoxy, m is 0, 1, or 2; and pharmaceutically acceptable salts thereof.

In other embodiments, the imirestat analogues can include compounds selected from the group consisting of:

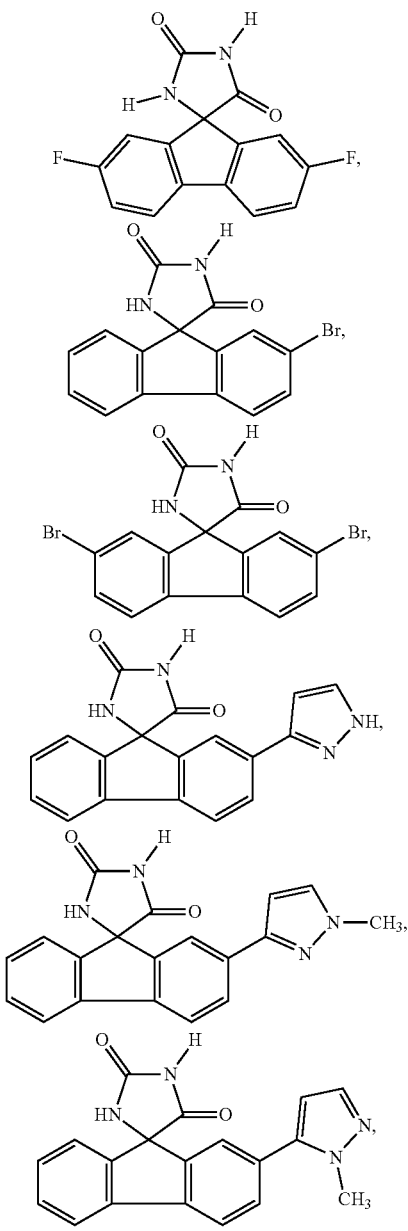

-continued
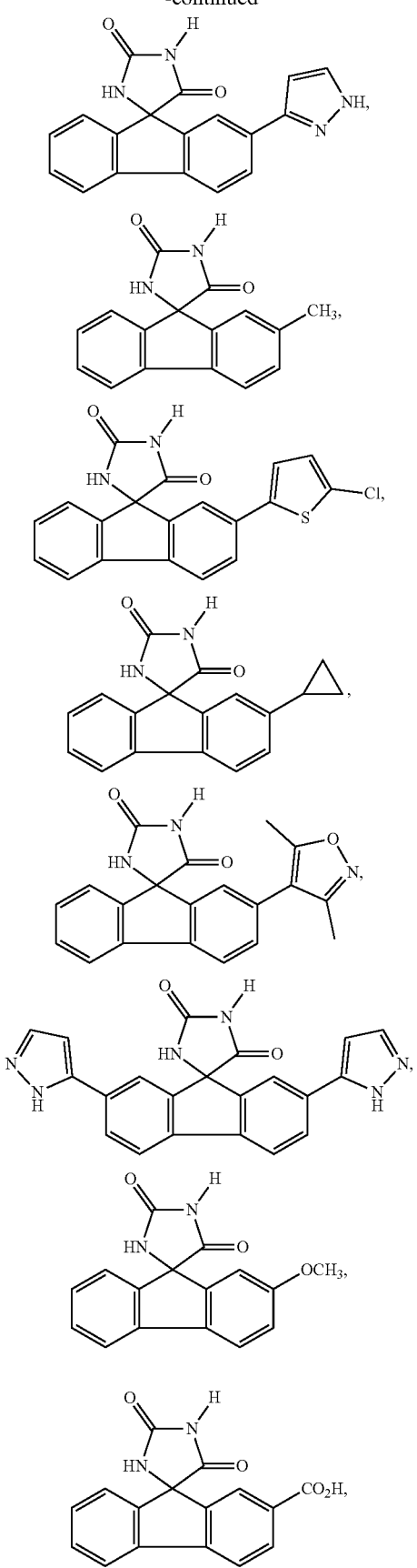
-continued
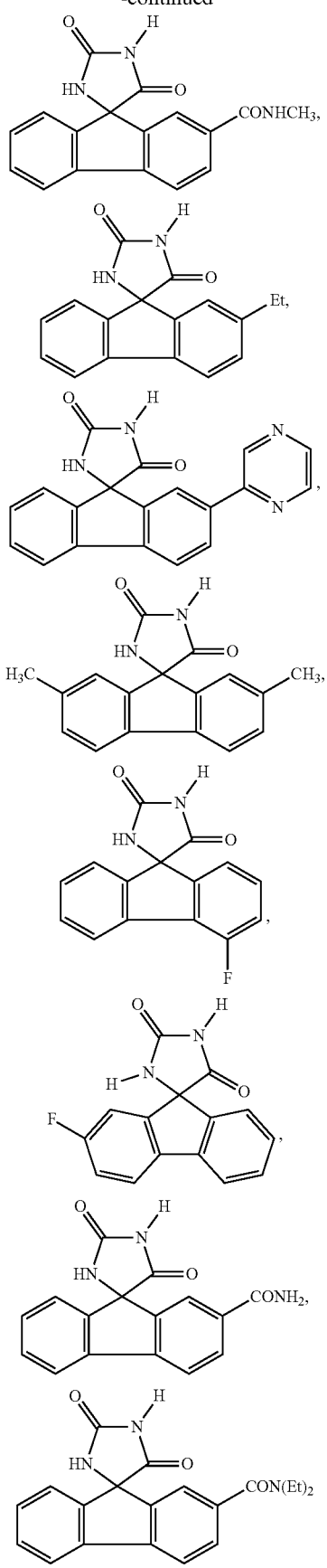

-continued

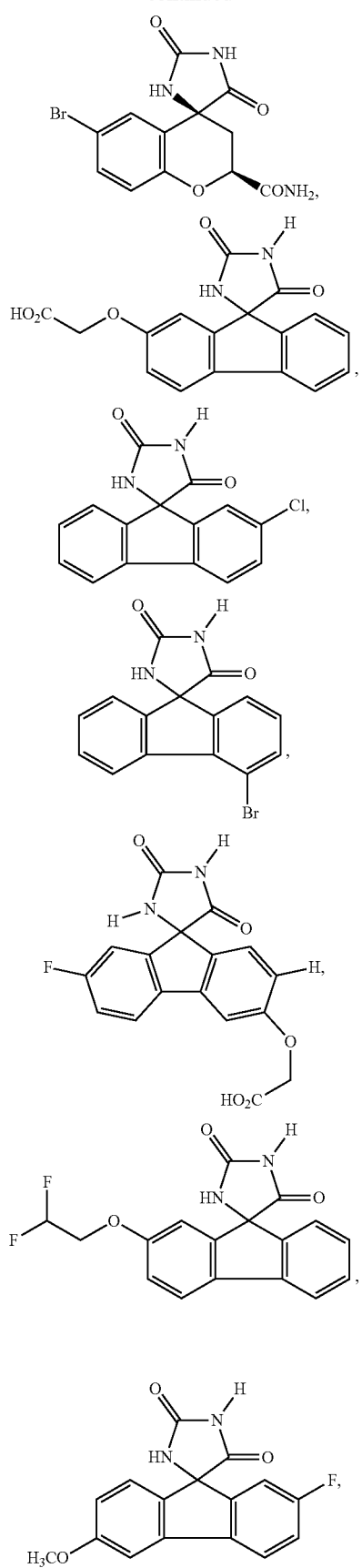
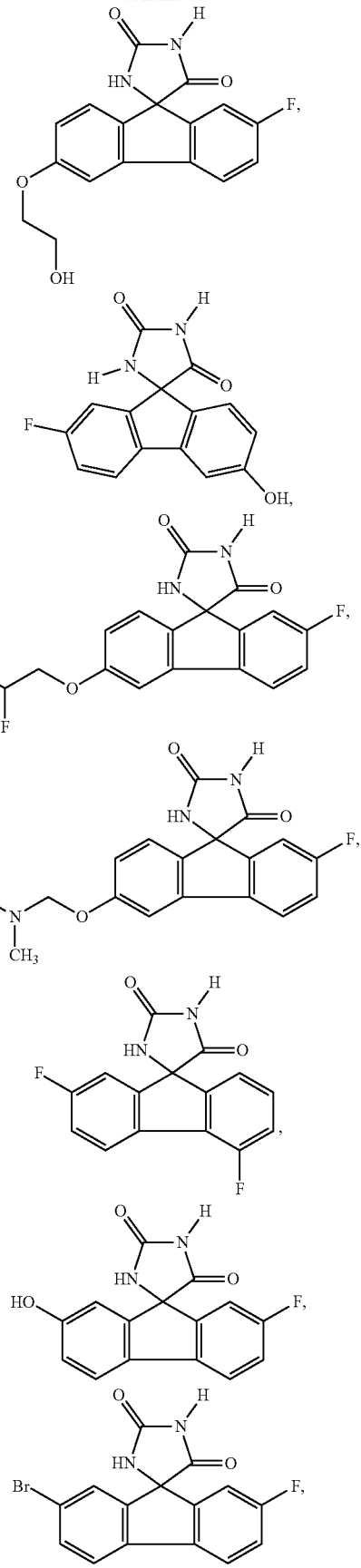

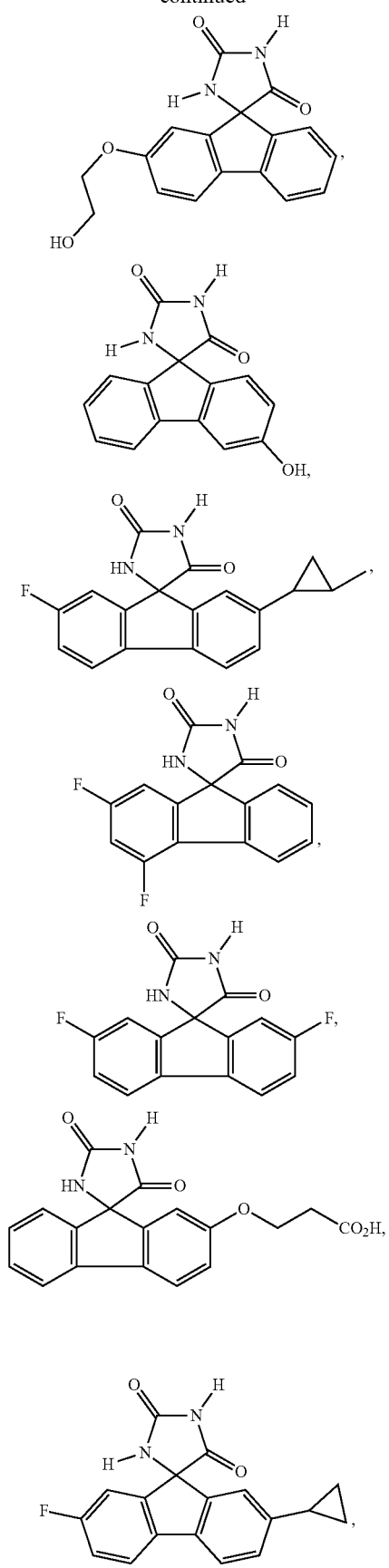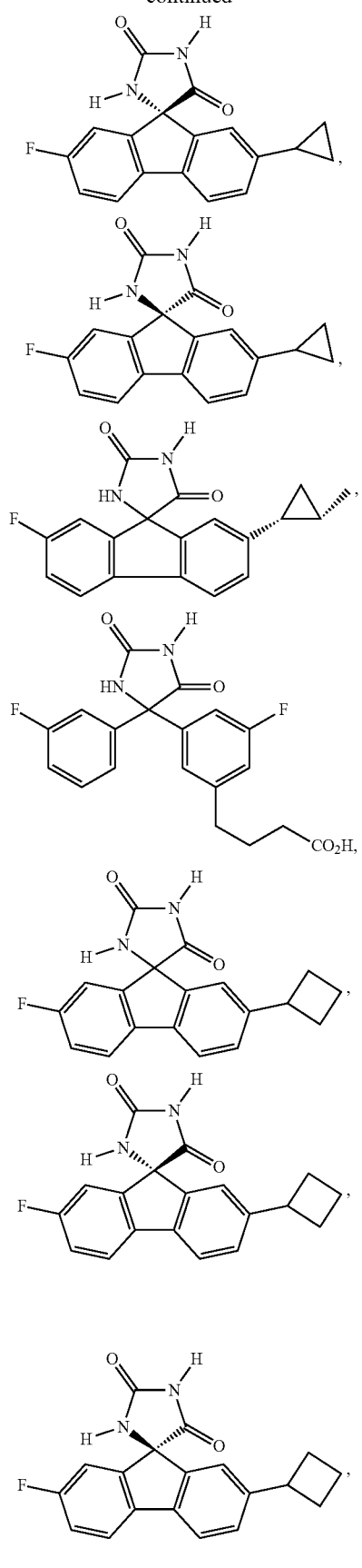

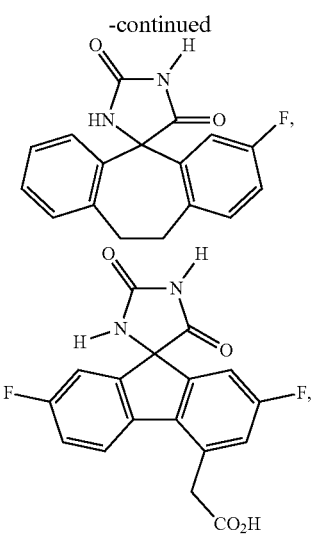
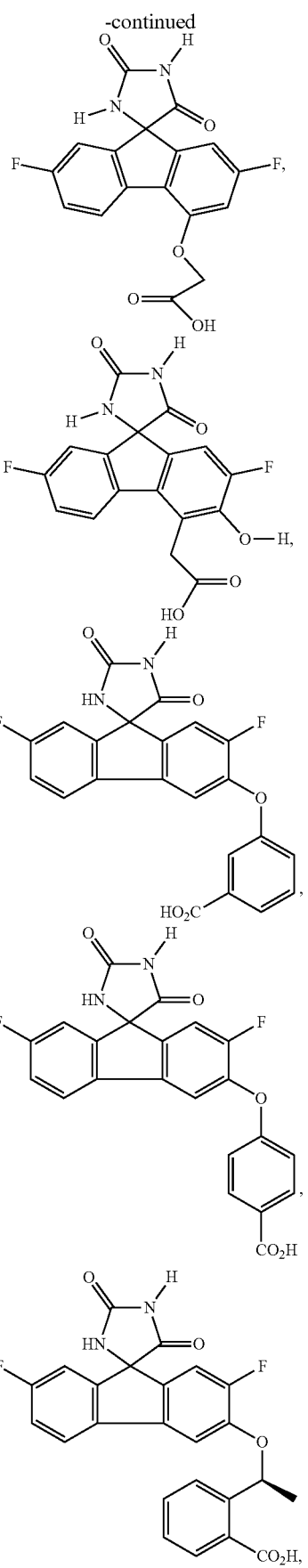

35
-continued
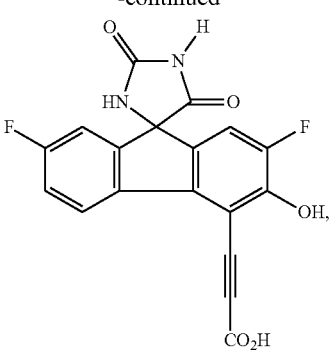
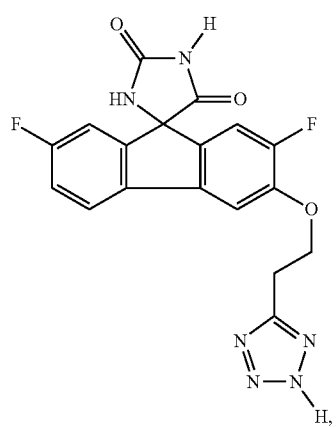
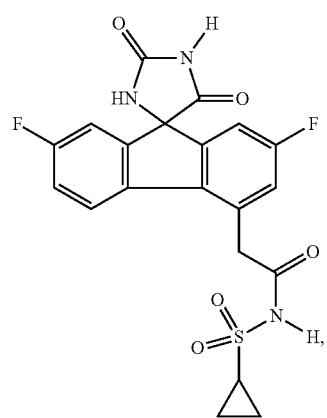
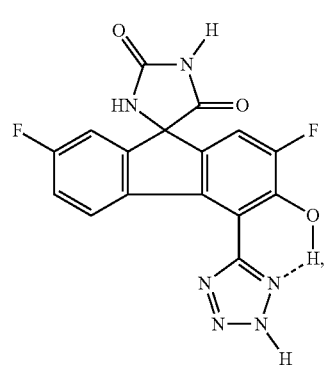
36
-continued
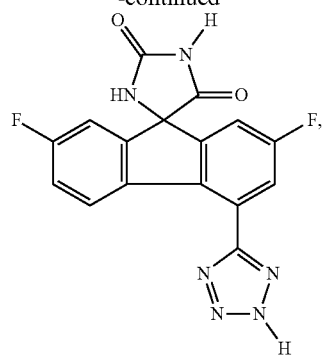
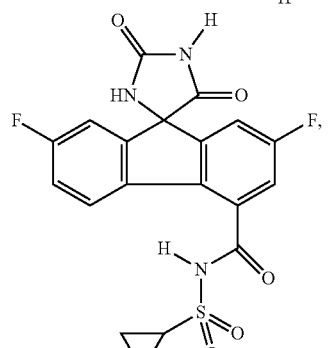
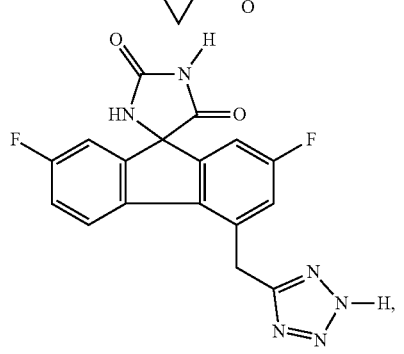
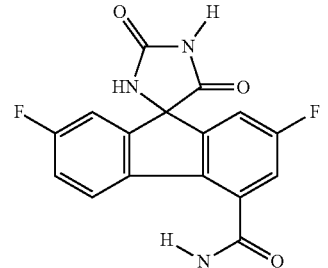
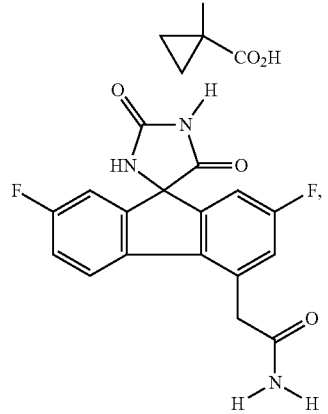

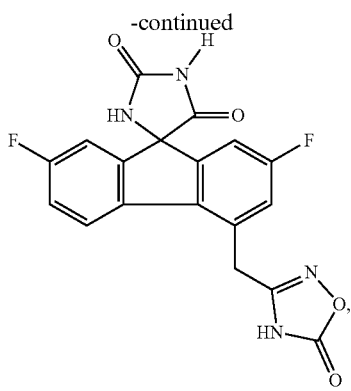

and pharmaceutically acceptable salts thereof.

Still other examples of selective and/or partially selective AKR1A1 inhibitors are disclosed in the following publications: Mechanism of Human Aldehyde Reductase: Characterization of the Active Site Pocket, Oleg A. Barski et al., Biochemistry 1995, 34, 11264-11275, In vivo role of aldehyde reductase, M. Takahashi et al., Biochim Biophys Acta. 2012 November; 1820(11):1787-96, The Aldo-Keto Reductase Superfamily and its Role in Drug Metabolism and Detoxification, Oleg A. Barski et al., Drug Metab Rev. 2008; 40(4): 553-624, Asborin Inhibits Aldo/Keto Reductase 1A1, Matthias Scholz et al., ChemMedChem, 2011, 6, 89-93, Inhibition of Aldehyde Reductase by Aldose Reductase Inhibitors, Sanai Sato et al., Biochemical Pharmacology, 1990. 40, 1033-1042, Inhibition of human aldose and aldehyde reductases by non-steroidal anti-inflammatory drugs, D. Michelle Ratliff et al., Advances in Experimental Medicine and Biology, Volume: 463, Issue: Enzymology and Molecular Biology of Carbonyl Metabolism 7, Pages: 493-499 (1999), Inhibition of aldehyde reductases, Philip J. Schofield et al., Progress in Clinical and Biological Research, 1987, 232, Issue: Enzymol. Mol. Biol. Carbonyl Metab., 287-96, Aldose Reductase Inhibitors as Potential Therapeutic Drugs of Diabetic Complications, By Changjin Zhu, DOI: 10.5772/54642, Aldose Reductase Inhibitors: A Potential New Class of Agents for the Pharmacological Control of Certain Diabetic Complications, Peter F. Kador et al., Journal of Medicinal Chemistry, 1985, 28, 841-849, Recent clinical experience with aldose reductase inhibitors, H. M. J. Krans, Journal of Diabetes and its Complications, 1992, 6, 39-44, A Novel Series of Non-Carboxylic Acid, Non-Hydantoin Inhibitors of Aldose Reductase with Potent Oral Activity in Diabetic Rat Models: 6-(5-Chloro-3-methylbenzofuran-2-sulfonyl)-2H-pyridazin-3-one and Congeners, Banavara L. Mylari et al., J. Med. Chem. 2005, 48, 6326-6339, A Diverse Series of Substituted Benzenesulfonamides as Aldose Reductase Inhibitors with Antioxidant Activity: Design, Synthesis, and in Vitro Activity, Polyxeni Alexiou et al., J. Med. Chem. 2010, 53, 7756-7766, Aldose Reductase Inhibitors as Potential Therapeutic Drugs of Diabetic Complications, By Changjin Zhu, DOI: 10.5772/54642, Aldose Reductase Inhibitors: A Potential New Class of Agents for the Pharmacological Control of Certain Diabetic Complications, Peter F. Kador et al., Journal of Medicinal Chemistry, 1985, 28, 841-849, Recent clinical experience with aldose reductase inhibitors, H. M. J. Krans, Journal of Diabetes and its Complications, 1992, 6, 39-44, A Novel Series of Non-Carboxylic Acid, Non-Hydantoin Inhibitors of Aldose Reductase with Potent Oral Activity in Diabetic Rat Models: 6-(5-Chloro-3-methylbenzofuran-2-sulfonyl)-2H-pyridazin-3-one and Congeners, Banavara L. Mylari et al., J. Med. Chem. 2005, 48, 6326-6339, A Diverse Series of Substituted Benzenesulfonamides as Aldose Reductase Inhibitors with Antioxidant Activity: Design, Synthesis, and in Vitro Activity, Polyxeni Alexiou et al., J. Med. Chem. 2010, 53, 7756-7766, all of which are incorporated herein by reference in their entirety. It will be appreciated that any potential selective or partially selective AKR1A1 inhibitors can be used in the compositions and methods recited herein.

The ADH inhibitors used in the methods described herein can include auramine O, allicin, 1,5-anilinonaphthalenesulfonic acid, 1,7-anilinonaphthalenesulfonic acid, 1,8-anilinonaphthalenesulfonic acid, berberine, canavanine, 2,2'-diprypyl, imidazole, m-methylbenzamide, 4-methylpyrazole, pyrazole, 4-pentylpyrazole, 0-phenanthroline, alrestatin, anthranic acid, O-carboxybenzaldehyde, 2,3-dimethylsuccinic acid, ethacrynic acid, isonicotinic acid, phenacemide, quercetin, quercitrin, sorbinil, tetramethyleneglutaric acid, valproic acid, propranolol, 2,2,2-trichloroethanol, 4,5-diaminopyrazole and its derivatives and 2-ethyl-5-methyl-2H-3,4-diaminopyrazole. See U.S. Patent Application Publication 20030138390, which is incorporated herein by reference in its entirety.

Fomepizole (4-methylpyrazole) is also a competitive inhibitor of ADH. Pyrazole and its 4-substituted derivatives competitively inhibit the binding of alcohol substrates through the formation of a tight enzyme NAD inhibitor complex, in which pyrazole nitrogens interact with both zinc and NAD$^+$. Xie et al., J. Biol. Chem., 272:18558-18563 (1997), herein incorporated by reference.

CNAD (5-beta-D-ribofuranosylnicotinamide adenine dinucleotide) is an isomeric and isomeric analogue of NAD, in which the nicotinamide ring is linked to the sugar via a C-glycosyl (C5-C1') bond. CNAD acts as a general dehydrogenase inhibitor but shows unusual specificity and affinity for liver alcohol dehydrogenase. Goldstein et al., J. Med. Chem., 37:392-9 (1994), herein incorporated by reference.

Other ADH inhibitors include dimethyl sulfoxide, Perlman and Wolff, Science, 160:317-9 (1968); and p-methylbenzyl hydroperoxide, Skursky et al., Biochem Int., 26:899-904 (1992), herein incorporated by reference.

In some embodiments, the ADH inhibitor can be a selective ADH6 inhibitor or partially selective ADH6 inhibitor that does not inhibit ADH3. In other embodiments, the ADH inhibitor does not inhibit ADH3 but inhibits other ADHs, such as ADH6.

The PKM2 inhibitors used in the methods described herein can include any agent that can inhibit the activity of PKM2. Examples of PKM2 inhibitors include agents that can S-nitrosylate PKM2, such as SNO-CoA (or derivatives thereof e.g. SNO-cysteamine) as well as small molecule inhibitors of PKM2. For example, the small molecule inhibitor can be Alkannin, Shikonin or a derivative or prodrug thereof. Further examples of small molecule PKM2 inhibitor for use according to the embodiments include, without limitation, compounds according the structures (I)-(VIII), below and those disclosed in U.S. Pat. Pub. 2010/0099726, which is incorporated herein by reference in its entirety.

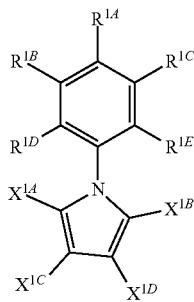

(I)

wherein each of $R^{1A}$, $R^{1B}$, $R^{1C}$, $R^{1D}$, $R^{1E}$, $X^{1A}$, $X^{1B}$, $X^{1C}$, and $X^{1D}$ is independently, selected from H, halide, nitro, $C_{1-4}$ alkyl, $C_{2-4}$ alkenyl, $C_{2-4}$ alkynyl, $OR^{1K}$, $OC(O)R^{1L}$, $NR^{1M}R^{1N}$, $NHC(O)R^{1O}$, $NHC(S)R^{1P}$, $NHC(O)OR^{1Q}$, $NHC(S)OR^{1R}$, $NHC(O)NHR^{1S}$, $NHC(S)NHR^{1T}$, $NHC(O)SR^{1U}$, $NHC(S)SR^{1V}$, $NHS(O)_2R^{1W}$, $C(O)OR^{1X}$, $C(O)NHR^{1Y}$, $(CH_2)_{1-4}OH$, $C(O)R^{1Z}$, $CH_2R^{1AA}$, $SO_3H$, $SO_2R^{1BB}$, $S(O)R^{1CC}$, $SR^{1DD}$, $SO_2NHR^{1EE}$, and $S(CH_2)_{1-4}C(O)OH$; and each of $R^{1K}$, $R^{1L}$, $R^{1M}$, $R^{1N}$, $R^{1O}$, $R^{1P}$, $R^{1Q}$, $R^{1R}$, $R^{1S}$, $R^{1T}$, $R^{1U}$, $R^{1V}$, $R^{1W}$, $R^{1X}$, $R^{1Y}$, $R^{1Z}$, $R^{1AA}$, $R^{1BB}$, $R^{1CC}$, $R^{1DD}$, and $R^{1EE}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl, and salts thereof. In one particular embodiment, $X^{1A}$ and $X^{1B}$ are both methyl, $X^{1C}$ and $X^{1D}$ are both H, and each of $R^{1A}$, $R^{1B}$, $R^{1C}$, $R^{1D}$, and $R^{1E}$ is, independently, selected from H, halide, nitro, $C_{1-4}$ alkyl, $C_{2-4}$ alkenyl, $C_{2-4}$ alkynyl, $OR^{1K}$, $OC(O)R^{1L}$, $NR^{1M}R^{1N}$, $NHC(O)R^{1O}$, $NHC(S)R^{1P}$, $NHC(O)OR^{1Q}$, $NHC(S)OR^{1R}$, $NHC(O)NHR^{1S}$, $NHC(S)NHR^{1T}$, $NHC(O)SR^{1U}$, $NHC(S)SR^{1V}$, $NHS(O)_2R^{1W}$, $C(O)OR^{1X}$, $C(O)NHR^{1Y}$, $(CH_2)_{1-4}OH$, $C(O)R^{1Z}$, $CH_2R^{1AA}$, $SO_3H$, $SO_2R^{1BB}$, $S(O)R^{1CC}$, $SR^{1DD}$, $SO_2NHR^{1EE}$, and $S(CH_2)_{1-4}C(O)OH$; and each of $R^{1K}$, $R^{1L}$, $R^{1M}$, $R^{1N}$, $R^{1O}$, $R^{1P}$, $R^{1Q}$, $R^{1R}$, $R^{1S}$, $R^{1T}$, $R^{1U}$, $R^{1V}$, $R^{1W}$, $R^{1X}$, $R^{1Y}$, $R^{1Z}$, $R^{1AA}$, $R^{1BB}$, $R^{1CC}$, $R^{1DD}$, and $R^{1EE}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl, and salts thereof.

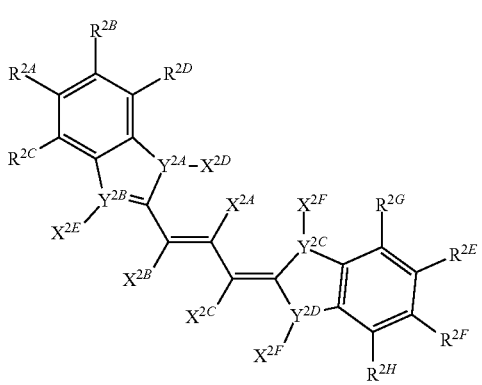

(II)

wherein each of $X^{2A}$, $X^{2B}$, $X^{2C}$, $X^{2D}$, $X^{2E}$, $X^{2E}$, and $X^{2G}$ is, independently, selected from H, $C_{1-8}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-8}$ heteroalkyl; and each of $Y^{2A}$, $Y^{2C}$, and $Y^{2D}$ is, independently, selected from N and CH; and $Y^{2B}$ is, independently, selected from $N^+$ and C; and each of $R^{2A}$, $R^{2B}$, $R^{2C}$, $R^{2D}$, $R^{2E}$, $R^{2F}$, $R^{2G}$, and $R^{2H}$ is, independently, selected from H, halide, nitro, $C_{1-4}$ alkyl, $C_{1-4}$ alkenyl, $C_{1-4}$ alkynyl, $OR^{2K}$, $OC(O)R^{2L}$, $NR^{2M}R^{2N}$, $NHC(O)R^{2O}$, $NHC(S)R^{2P}$, $NHC(O)OR^{2Q}$, $NHC(S)OR^{2R}$, $NHC(O)NHR^{2S}$, $NHC(S)NHR^{2T}$, $NHC(O)SR^{2U}$, $NHC(S)SR^{2V}$, $NHS(O)_2R^{2W}$, $C(O)OR^{2X}$, $C(O)NHR^{2Y}$, $(CH_2)_{1-4}OH$, $C(O)R^{2Z}$, $CH_2R^{2AA}$, $SO_3H$, $SO_2R^{2BB}$, $S(O)R^{2CC}$, $SR^{2DD}$, $SO_2NHR^{2EE}$, and $S(CH_2)_{1-4}C(O)OH$; and each of $R^{2K}$, $R^{2L}$, $R^{2M}$, $R^{2N}$, $R^{2O}$, $R^{2P}$, $R^{2Q}$, $R^{2R}$, $R^{2S}$, $R^{2T}$, $R^{2U}$, $R^{2V}$, $R^{2W}$, $R^{2X}$, $R^{2Y}$, $R^{2Z}$, $R^{2AA}$, $R^{2BB}$, $R^{2CC}$, $R^{2DD}$, and $R^{2EE}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and CM heteroalkyl, and salts thereof. In one particular embodiment, each of $X^{2A}$, $X^{2B}$, $X^{2C}$, $R^{2C}$, $R^{2D}$, $R^{2G}$, and $R^{2H}$ is H; and each of $Y^{2A}$, $Y^{2C}$, and $Y^{2D}$ is N; and $Y^{2B}$ is $N^+$; and each of $X^{2D}$, $X^{2E}$, $X^{2E}$, and $X^{2G}$ is, independently, selected from H, $C_{1-8}$ alkyl, $C_{2-4}$ alkenyl, $C_{2-4}$ alkynyl, and $C_{1-8}$ heteroalkyl; and each of $R^{2A}$, $R^{2B}$, $R^{2E}$, $R^{2F}$ is, independently, selected from H, halide, nitro, $C_{1-4}$ alkyl, $C_{2-4}$ alkenyl, $C_{1-4}$ alkynyl, $OR^{2K}$, $OC(O)R^{2L}$, $NR^{2M}R^{2N}$, $NHC(O)R^{2O}$, $NHC(S)R^{2P}$, $NHC(O)OR^{2Q}$, $NHC(S)OR^{2R}$, $NHC(O)NHR^{2S}$, $NHC(S)NHR^{2T}$, $NHC(O)SR^{2U}$, $NHC(S)SR^{2V}$, $NHS(O)_2R^{2W}$, $C(O)OR^{2X}$, $C(O)NHR^{2Y}$, $(CH_2)_{1-4}OH$, $C(O)R^{2Z}$, $CH_2R^{2AA}$, $SO_3H$, $SO_2R^{2BB}$, $S(O)R^{2CC}$, $SR^{2DD}$, $SO_2NHR^{2EE}$, and $S(CH_2)_{1-4}C(O)OH$; and each of $R^{2K}$, $R^{2L}$, $R^{2M}$, $R^{2N}$, $R^{2O}$, $R^{2P}$, $R^{2Q}$, $R^{2R}$, $R^{2S}$, $R^{2T}$, $R^{2U}$, $R^{2V}$, $R^{2W}$, $R^{2X}$, $R^{2Y}$, $R^{2Z}$, $R^{2AA}$, $R^{2BB}$, $R^{2CC}$, $R^{2DD}$, and $R^{2EE}$ is, independently, selected from H, $C_{1-4}$ alkyl, and salts thereof.

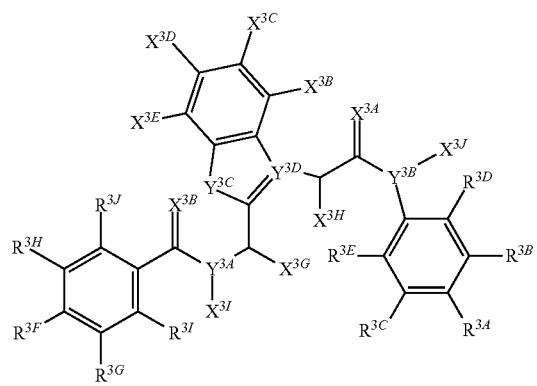

(III)

wherein each of $X^{3A}$ and $X^{3B}$ is, independently, selected from S, O, NH, and $CH_2$; and each of $X^{3G}$ and $X^{3H}$ is, independently, selected from H, $C_{1-8}$ alkyl, $C_{2-4}$ alkenyl, $C_{2-4}$ alkynyl, and $C_{1-8}$ heteroalkyl; and each of $Y^{3A}$ and $Y^{3B}$ is, independently, selected from O, CH, N, and S; and $X^{3I}$ is empty when $Y^{3A}$ is S or O, $X^{3J}$ is empty when $Y^{3B}$ is S or O, otherwise each of $X^{3I}$ and $X^{3J}$ is, independently, selected from H, $C_{1-8}$ alkyl, $C_{2-4}$ alkenyl, $C_{2-4}$ alkynyl, and $C_{1-8}$ heteroalkyl; and each of $Y^{3C}$ and $Y^{3D}$ is, independently, selected from CH and N; and each of $R^{3A}$, $R^{3B}$, $R^{3C}$, $R^{3D}$, $R^{3E}$, $R^{3F}$, $R^{3G}$, $R^{3H}$, $R^{3I}$, $R^{3J}$, $X^{3C}$, $X^{3D}$, $X^{3E}$, and $X^{3E}$ is, independently, selected from H, halide, nitro, CIA alkyl, $C_{2-4}$ alkenyl, $C_{2-4}$ alkynyl, $OR^{3K}$, $OC(O)R^{3L}$, $NR^{3M}R^{3N}$, NHC(O)

$R^{3O}$, $NHC(S)R^{3P}$, $NHC(O)OR^{3Q}$, $NHC(S)OR^{3R}$, $NHC(O)NHR^{3S}$, $NHC(S)NHR^{3T}$, $NHC(O)SR^{3U}$, $NHC(S)SR^{3V}$, $NHS(O)_2R^{3W}$, $C(O)OR^{3X}$, $C(O)NHR^{3Y}$, $(CH_2)_{1-4}OH$, $C(O)R^{3Z}$, $CH_2R^{3AA}$, $SO_3H$, $SO_2R^{3BB}$, $S(O)R^{3CC}$, $SR^{3DD}$ $SO_2NHR^{3EE}$, and $S(CH_2)_{1-4}C(O)OH$; and each of $R^{3K}$, $R^{3L}$, $R^{3M}$, $R^{3N}$, $R^{3O}$, $R^{3P}$, $R^{3Q}$, $R^{3R}$, $R^{3S}$, $R^{3T}$, $R^{3U}$, $R^{3V}$, $R^{3W}$, $R^{3X}$, $R^{3Y}$, $R^{3Z}$, $R^{3AA}$, $R^{3BB}$, $R^{3CC}$, $R^{3DD}$, and $R^{3EE}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl, and salts thereof. In one particular embodiment, each of $X^{3A}$ and $X^{3B}$ is, independently, selected from S and O; and each of $X^{3G}$ and $X^{3H}$, $X^{3I}$, and $X^{3J}$ is H; and each of $Y^{3A}$, $Y^{3B}$, $Y^{3C}$ and $Y^{3D}$ is, independently, selected from CH and N; and each of $R^{3A}$, $R^{3B}$, $R^{3C}$, $R^{3D}$, $R^{3E}$, $R^{3F}$, $R^{3G}$, $R^{3H}$, $R^{3I}$, $R^{3J}$, $X^{3C}$, $X^{3D}$, $X^{3E}$, and $X^{3F}$ is, independently, selected from H, halide, nitro, $C_{1-4}$ alkyl, $C_{2-4}$ alkenyl, $C_{2-4}$ alkynyl, $OR^{3K}$, $OC(O)R^{3L}$, $NR^{3M}R^{3N}$, $NHC(O)R^{3O}$, $NHC(S)R^{3P}$, $NHC(O)OR^{3Q}$, $NHC(S)OR^{3R}$, $NHC(O)NHR^{3S}$, $NHC(S)NHR^{3T}$, $NHC(O)SR^{3U}$, $NHC(S)SR^{3V}$, $NHS(O)_2R^{3W}$, $C(O)OR^{3X}$, $C(O)NHR^{3Y}$, $(CH_2)_{1-4}OH$, $C(O)R^{3Z}$, $CH_2R^{3AA}$, $SO_3H$, $SO_2R^{3BB}$, $S(O)R^{3CC}$, $SR^{3DD}$ $SO_2NHR^{3EE}$, and $S(CH_2)_{1-4}C(O)OH$; and each of $R^{3K}$, $R^{3L}$, $R^{3M}$, $R^{3N}$, $R^{3O}$, $R^{3P}$, $R^{3Q}$, $R^{3R}$, $R^{3S}$, $R^{3T}$, $R^{3U}$, $R^{3V}$, $R^{3W}$, $R^{3X}$, $R^{3Y}$, $R^{3Z}$, $R^{3AA}$, $R^{3BB}$, $R^{3CC}$, $R^{3DD}$, and $R^{3EE}$ is, independently, selected from H and CIA alkyl, and salts thereof.

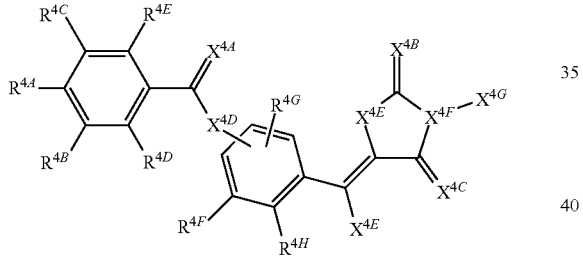

wherein each of $X^{4A}$, $X^{4B}$, and $X^{4C}$ is, independently, selected from S, O, NH, $CH_2$, and two hydrogen atoms; and each of $X^{4G}$ and $X^{4H}$ is, independently, selected from H, $C_{1-8}$ alkyl, $C_{2-4}$ alkenyl, $C_{2-4}$ alkynyl, and $C_{1-8}$ heteroalkyl; and each of $X^{4D}$ and $X^{4E}$ is, independently, selected from O, $CH_2$, NH, and S; and $X^{4F}$ is, independently, selected from CH and N; and each of $R^{4A}$, $R^{4B}$, $R^{4C}$, $R^{4D}$, $R^{4E}$, $R^{4F}$, $R^{4G}$, $R^{4H}$, and $R^{4I}$, is, independently, selected from H, halide, nitro, $C_{1-4}$ alkyl, $C_{1-4}$ alkenyl, $C_{1-4}$ alkynyl, $OR^{4K}$, $OC(O)R^{4L}$, $NR^{4M}R^{4N}$, $NHC(O)R^{4O}$, $NHC(S)R^{4P}$, $NHC(O)OR^{4Q}$, $NHC(S)OR^{4R}$, $NHC(O)NHR^{4S}$, $NHC(S)NHR^{4T}$, $NHC(O)SR^{4U}$, $NHC(S)SR^{4V}$, $NHS(O)_2R^{4W}$, $C(O)OR^{4X}$, $C(O)NHR^{4Y}$, $(CH_2)_{1-4}OH$, $C(O)R^{4Z}$, $CH_2R^{4AA}$, $SO_3H$, $SO_2R^{4BB}$, $S(O)R^{4CC}$, $SR^{4DD}$, $SO_2NHR^{4EE}$, and $S(CH_2)_{1-4}C(O)OH$; and each of $R^{4K}$, $R^{4L}$, $R^{4M}$, $R^{4N}$, $R^{4O}$, $R^{4P}$, $R^{4Q}$, $R^{4R}$, $R^{4S}$, $R^{4T}$, $R^{4U}$, $R^{4V}$, $R^{4W}$, $R^{4X}$, $R^{4Y}$, $R^{4Z}$, $R^{4AA}$, $R^{4BB}$, $R^{4CC}$, $R^{4DD}$, and $R^{4EE}$ is, independently, selected from H, CM alkyl, $C_{1-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl, and salts thereof. In one particular embodiment, each of $X^{4A}$, $X^{4B}$, and $X^{4C}$ is, independently, selected from S, O, and two hydrogen atoms; and $X^{4G}$ is, independently, selected from H, $C_{1-8}$ alkyl, and $C_{1-8}$ heteroalkyl; and $X^{4H}$ is H; and each of $X^{4D}$ and $X^{4E}$ is, independently, selected from O, $CH_2$, NH, and S; and $X^{4F}$ is, independently, selected from CH and N; and each of $R^{4A}$, $R^{4B}$, $R^{4C}$, $R^{4D}$, $R^{4E}$, $R^{4F}$, $R^{4G}$, $R^{4H}$, and $R^{4I}$, is, independently, selected from H, halide, nitro, $C_{1-4}$ alkyl, $C_{2-4}$ alkenyl, $C_{2-4}$ alkynyl, $OR^{4K}$, $OC(O)R^{4L}$, $NR^{4M}R^{4N}$, $NHC(O)R^{4O}$, $NHC(S)R^{4P}$, $NHC(O)OR^{4Q}$, $NHC(S)OR^{4R}$, $NHC(O)NHR^{4S}$, $NHC(S)NHR^{4T}$, $NHC(O)SR^{4U}$, $NHC(S)SR^{4V}$, $NHS(O)_2R^{4W}$, $C(O)OR^{4X}$, $C(O)NHR^{4Y}$, $(CH_2)_{1-4}OH$, $C(O)R^{4Z}$, $CH_2R^{4AA}$, $SO_3H$, $SO_2R^{4BB}$, $S(O)R^{4CC}$, $SR^{4DD}$, $SO_2NHR^{4EE}$, and $S(CH_2)_{1-4}C(O)OH$; and each of $R^{4K}$, $R^{4L}$, $R^{4M}$, $R^{4N}$, $R^{4O}$, $R^{4P}$, $R^{4Q}$, $R^{4R}$, $R^{4S}$, $R^{4T}$, $R^{4U}$, $R^{4V}$, $R^{4W}$, $R^{4X}$, $R^{4Y}$, $R^{4Z}$, $R^{4AA}$, $R^{4BB}$, $R^{4CC}$, $R^{4DD}$, and $R^{4EE}$ is, independently, selected from H and $C_{1-4}$ alkyl, and salts thereof.

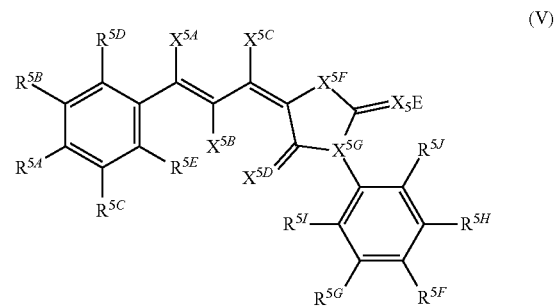

(V)

wherein each of $X^{5A}$, $X^{5B}$, and $X^{5C}$ is, independently, selected from H, $C_{1-8}$ alkyl, $C_{2-4}$ alkenyl, $C_{2-4}$ alkynyl, and $C_{1-8}$ heteroalkyl; and each of $X^{5D}$ and $X^{5E}$ is, independently, selected from S, NH, O, and $CH_2$; and $X^{5E}$ is, independently, selected from O, NH, $CH_2$, and S; and $X^{5G}$ is, independently, selected from CH and N; and each of $R^{5A}$, $R^{5B}$, $R^{5C}$, $R^{5D}$, $R^{5E}$, $R^{5F}$, $R^{5G}$, $R^{5H}$, $R^{5I}$, and $R^{5J}$, is, independently, selected from H, halide, nitro, $C_{1-4}$ alkyl, $C_{2-4}$ alkenyl, $C_{2-4}$ alkynyl, $OR^{5K}$, $OC(O)R^{5L}$, $NR^{5M}R^{5N}$, $NHC(O)R^{5O}$, $NHC(S)R^{5P}$, $NHC(O)OR^{5Q}$, $NHC(S)OR^{5R}$, $NHC(O)NHR^{5S}$, $NHC(S)NHR^{5T}$, $NHC(O)SR^{5U}$, $NHC(S)SR^{5V}$, $NHS(O)_2R^{5W}$, $C(O)OR^{5X}$, $C(O)NHR^{5Y}$, $(CH_2)_{1-4}OH$, $C(O)R^{5Z}$, $CH_2R^{5AA}$, $SO_3H$, $SO_2R^{5BB}$, $S(O)R^{5CC}$, $SR^{5DD}$, $SO_2NHR^{5EE}$, and $S(CH_2)_{1-4}C(O)OH$; and each of $R^{5K}$, $R^{5L}$, $R^{5M}$, $R^{5N}$, $R^{5O}$, $R^{5P}$, $R^{5Q}$, $R^{5R}$, $R^{5S}$, $R^{5T}$, $R^{5U}$, $R^{5V}$, $R^{5W}$, $R^{5X}$, $R^{5Y}$, $R^{5Z}$, $R^{5AA}$, $R^{5BB}$, $R^{5CC}$, $R^{5DD}$, and $R^{5EE}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl, and salts thereof. In one particular embodiment, each of $X^{5A}$, $X^{5B}$, and $X^{5C}$ is H; and each of $X^{5D}$ and $X^{5E}$ is, independently, selected from S and O; and $X^{5E}$ is, independently, selected from O, NH, $CH_2$, and S; and $X^{5G}$ is, independently, selected from CH and N; and each of $R^{5A}$, $R^{5B}$, $R^{5C}$, $R^{5D}$, $R^{5E}$, $R^{5F}$, $R^{5G}$, $R^{5H}$, $R^{5I}$, and $R^{5J}$, is, independently, selected from H, halide, nitro, $C_{1-4}$ alkyl, $C_{2-4}$ alkenyl, $C_{1-4}$ alkynyl, $OR^{5K}$, $OC(O)R^{5L}$, $NR^{5M}R^{5N}$, $NHC(O)R^{5O}$, $NHC(S)R^{5P}$, $NHC(O)OR^{5Q}$, $NHC(S)OR^{5R}$, $NHC(O)NHR^{5S}$, $NHC(S)NHR^{5T}$, $NHC(O)SR^{5U}$, $NHC(S)SR^{5V}$, $NHS(O)_2R^{5W}$, $C(O)OR^{5X}$, $C(O)NHR^{5Y}$, $(CH_2)_{1-4}OH$, $C(O)R^{5Z}$, $CH_2R^{5AA}$, $SO_3H$, $SO_2R^{5BB}$, $S(O)R^{5CC}$, $SR^{5DD}$, $SO_2NHR^{5EE}$, and $S(CH_2)_{1-4}C(O)OH$; and each of $R^{5K}$, $R^{5L}$, $R^{5M}$, $R^{5N}$, $R^{5O}$, $R^{5P}$, $R^{5Q}$, $R^{5R}$, $R^{5S}$, $R^{5T}$, $R^{5U}$, $R^{5V}$, $R^{5W}$, $R^{5X}$, $R^{5Y}$, $R^{5Z}$, $R^{5AA}$, $R^{5BB}$, $R^{5CC}$, $R^{5DD}$, and $R^{5EE}$ is, independently, selected from H and $C_{1-4}$ alkyl, and salts thereof.

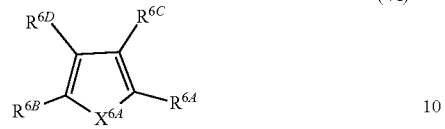

(VI)

wherein $X^{6A}$ is, independently, selected from S, NH, and O; and each of $R^{6A}$, $R^{6B}$, $R^{6C}$, and $R^{6D}$, is, independently, selected from H, halide, nitro, $C_{1-4}$ alkyl, $C_{1-4}$ alkenyl, $C_{1-4}$ alkynyl, $OR^{6K}$, $OC(O)R^{6L}$, $NR^{6M}R^{6N}$, $NHC(O)R^{6O}$, $NHC(S)R^{6P}$, $NHC(O)OR^{6Q}$, $NHC(S)OR^{6R}$, $NHC(O)NHR^{6S}$, $NHC(S)NHR^{6T}$, $NHC(O)SR^{6U}$, $NHC(S)SR^{6V}$, $NHS(O)_2R^{6W}$, $C(O)OR^{6X}$, $C(O)NHR^{6Y}$, $(CH_2)_{1-4}OH$, $C(O)R^{6Z}$, $CH_2R^{6AA}$, $SO_3H$, $SO_2R^{6BB}$, $S(O)R^{6CC}$, $SR^{6DD}$, $SO_2NHR^{6EE}$, and $S(CH_2)_{1-4}C(O)OH$; and each of $R^{6K}$, $R^{6L}$, $R^{6M}$, $R^{6N}$, $R^{6O}$, $R^{6P}$, $R^{6Q}$, $R^{6R}$, $R^{6S}$, $R^{6T}$, $R^{6U}$, $R^{6V}$, $R^{6W}$, $R^{6X}$, $R^{6Y}$, $R^{6Z}$, $R^{6AA}$, $R^{6BB}$, $R^{6CC}$, $R^{6DD}$, and $R^{6EE}$ is, independently, selected from H, $C_{1-4}$ alkyl, $C_{2-4}$ alkenyl, $C_{1-4}$ alkynyl, $C_{2-6}$ heterocyclyl, $C_{6-12}$ aryl, $C_{7-14}$ alkaryl, $C_{3-10}$ alkheterocyclyl, and CM heteroalkyl, and salts thereof. In one particular embodiment, $X^{6A}$ is, independently, selected from S and O; and each of $R^{6C}$ and $R^{6D}$ is H; and each of $R^{6A}$ and $R^{6B}$, is, independently, selected from H, halide, nitro, $C_{1-4}$ alkyl, $C_{2-4}$ alkenyl, $C_{1-4}$ alkynyl, $OR^{6K}$, $OC(O)R^{6L}$, $NR^{6M}R^{6N}$, $NHC(O)R^{6O}$, $NHC(S)R^{6P}$, $NHC(O)OR^{6Q}$, $NHC(S)OR^{6R}$, $NHC(O)NHR^{6S}$, $NHC(S)NHR^{6T}$, $NHC(O)SR^{6U}$, $NHC(S)SR^{6V}$, $NHS(O)_2R^{6W}$, $C(O)OR^{6X}$, $C(O)NHR^{6Y}$, $(CH_2)_{1-4}OH$, $C(O)R^{6Z}$, $CH_2R^{6AA}$, $SO_3H$, $SO_2R^{6BB}$, $S(O)R^{6CC}$, $SR^{6DD}$, $SO_2NHR^{6EE}$, and $S(CH_2)_{1-4}C(O)OH$; and each of $R^{6K}$, $R^{6L}$, $R^{6M}$, $R^{6N}$, $R^{6O}$, $R^{6P}$, $R^{6Q}$, $R^{6R}$, $R^{6S}$, $R^{6T}$, $R^{6U}$, $R^{6V}$, $R^{6W}$, $R^{6X}$, $R^{6Y}$, $R^{6Z}$, $R^{6AA}$, $R^{6BB}$, $R^{6CC}$, $R^{6DD}$, and $R^{6EE}$ is, independently, selected from H and CIA alkyl, and salts thereof.

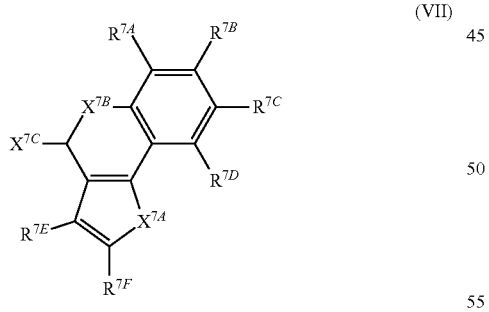

(VII)

wherein each of $X^{7A}$ and $X^{7B}$ is, independently, selected from S, NH, and O; and $X^{7C}$ is, independently, selected from S, NH, $CH_2$, and O; and each of $R^{7A}$, $R^{7B}$, $R^{7C}$, $R^{7D}$, $R^{7E}$, and $R^{7E}$ is, independently, selected from H, halide, nitro, $C_{1-4}$ alkyl, $C_{2-4}$ alkenyl, $C_{2-4}$ alkynyl, $OR^{7K}$, $OC(O)R^{7L}$, $NR^{7M}R^{7N}$, $NHC(O)R^{7O}$, $NHC(S)R^{7P}$, $NHC(O)OR^{7Q}$, $NHC(S)OR^{7R}$, $NHC(O)NHR^{7S}$, $NHC(S)NHR^{7T}$, $NHC(O)SR^{7U}$, $NHC(S)SR^{7V}$, $NHS(O)_2R^{7W}$, $C(O)OR^{7X}$, $C(O)NHR^{7Y}$, $(CH_2)_{1-4}OH$, $C(O)R^{7Z}$, $CH_2R^{7AA}$, $SO_3H$, $SO_2R^{7BB}$, $S(O)R^{7CC}$, $SR^{7DD}$, $SO_2NHR^{7EE}$, and $S(CH_2)_{1-4}C(O)OH$; and each of $R^{7K}$, $R^{7L}$, $R^{7M}$, $R^{7N}$, $R^{7O}$, $R^{7P}$, $R^{7Q}$, $R^{7R}$, $R^{7S}$, $R^{7T}$, $R^{7U}$, $R^{7V}$, $R^{7W}$, $R^{7X}$, $R^{7Y}$, $R^{7Z}$, $R^{7AA}$, $R^{7BB}$, $R^{7CC}$, $R^{7DD}$, and $R^{7EE}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl, and salts thereof. In one particular embodiment, each of $X^{7A}$ and $X^{7B}$ is, independently, selected from S, NH, and O; and $X^{7C}$ is, independently, selected from S, NH, $CH_2$, and O; and each of $R^{7A}$, $R^{7B}$, $R^{7C}$, $R^{7D}$, and $R^{7E}$, is, independently, selected from H, halide, nitro, CIA alkyl, $C_{2-4}$ alkenyl, $C_{2-4}$ alkynyl, $OR^{7K}$, $OC(O)R^{7L}$, $NR^{7M}R^{7N}$, $NHC(O)R^{7O}$, $NHC(S)R^{7P}$, $NHC(O)OR^{7Q}$, $NHC(S)OR^{7R}$, $NHC(O)NHR^{7S}$, $NHC(S)NHR^{7T}$, $NHC(O)SR^{7U}$, $NHC(S)SR^{7V}$, $NHS(O)_2R^{7W}$, $C(O)OR^{7X}$, $C(O)NHR^{7Y}$, $(CH_2)_{1-4}OH$, $C(O)R^{7Z}$, $CH_2R^{7AA}$, $SO_3H$, $SO_2R^{7BB}$, $S(O)R^{7CC}$, $SR^{7DD}$, $SO_2NHR^{7EE}$, and $S(CH_2)_{1-4}C(O)OH$; and each of $R^{7K}$, $R^{7L}$, $R^{7M}$, $R^{7N}$, $R^{7O}$, $R^{7P}$, $R^{7Q}$, $R^{7R}$, $R^{7S}$, $R^{7T}$, $R^{7U}$, $R^{7V}$, $R^{7W}$, $R^{7X}$, $R^{7Y}$, $R^{7Z}$, $R^{7AA}$, $R^{7BB}$, $R^{7CC}$, $R^{7DD}$, and $R^{7EE}$ is, independently, selected from H, $C_{1-4}$ alkyl; and $R^{7F}$ is, independently, selected from $OC(O)R^{7FF}$, $NHC(O)R^{7FF}$, $NHC(S)R^{7FF}$, $NHC(O)OR^{7FF}$, $NHC(S)OR^{7FF}$, $NHC(O)NHR^{7FF}$, $NHC(S)NHR^{7FF}$, $NHC(O)SR^{7FF}$, $NHC(S)SR^{7FF}$, $NHS(O)_2R^{7FF}$, $C(O)OR^{7FF}$, $C(O)NHR^{7FF}$, $C(O)R^{7FF}$, $SO_2R^{7FF}$, $S(O)R^{7FF}$, and $SO_2NHR^{7FF}$, where $R^{7FF}$ is selected from H and $C_{1-4}$ alkyl, and salts thereof.

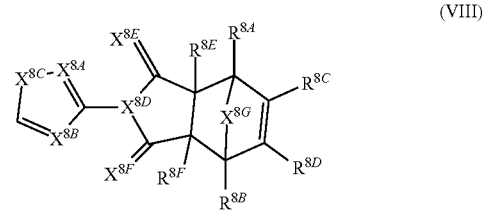

(VIII)

wherein $X^{8C}$ is, independently, selected from NH, $CH=CH$, or $N=CH$, and each of $X^{8A}$, $X^{8B}$, and $X^{8D}$ is, independently, selected from CH and N; and each of $X^{8E}$, $X^{8F}$, and $X^{8G}$ is, independently, selected from S, NH, $CH_2$, and O; and each of $R^{8A}$, $R^{8B}$, $R^{8C}$, $R^{8D}$, $R^{8E}$, and $R^{8F}$ is, independently, selected from H, $C_{1-4}$ alkyl, $C_{1-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl, and salts thereof. In one particular embodiment, $X^{8C}$ is, independently, selected from NH, $CH=CH$, or $N=CH$; and each of $X^{8A}$, $X^{8B}$, and $X^{8D}$ is, independently, selected from CH and N; and each of $X^{8E}$ and $X^{8F}$ is, independently, selected from S and O; $X^{8G}$ is $CH_2$; and each of $R^{8A}$, $R^{8B}$, $R^{8C}$, $R^{8D}$, $R^{8E}$, and $R^{8E}$ is, independently, selected from H and $C_{1-4}$ alkyl, and salts thereof.

Examples of compounds having formulas (I), (II), (III), (IV), (V), (VI), (VII), and (VIII) are described in U.S. Patent Application Publication No. 2010/0099726, which is incorporated by reference in its entirety.

In still further embodiments, a PKM2 inhibitor can be a compound that inhibits the formation of teterameric PKM2, which may reduce or prevent nuclear import of PKM2.

It will be appreciated that the other PKM2 inhibitors can be used in the methods described herein. These other PKM2 inhibitors can include known PKM2 inhibitors including, for example, shikonin analogues described in Li et al., Mol. Carcinog. 2014 May; 53(5): 403-412; Ning et al., Eur. J.

Med. Chem. 2017, Sep. 29, 138: 343-352; Ning et al., J. Enzyme Inhib. Med. Chem. 2018 December; 33(1) 126-129; and Kono et al., JCI Insight, 2019 Jun. 20; 4(12).

In other embodiments, the ADH inhibitor, AKR inhibitor, SCoR inhibitor, and/or PKM2 inhibitor can include an agent that reduces or inhibits ADH, AKR, SCoR, and/or PKM2 expression, such as ADH6 expression, AKR1A1, and/or PKM2 expression, in tissue or cells of a subject in need thereof. "Expression", means the overall flow of information from a gene to produce a gene product (typically a protein, optionally post-translationally modified or a functional/structural RNA).

In some embodiments, the agent can include an RNAi construct that inhibits or reduces expression of the ADH, AKR, SCoR, and/or PKM2 expression in a cell. RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner.

As used herein, the term "dsRNA" refers to siRNA molecules or other RNA molecules including a double stranded feature and that is able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response.

As used herein, the term "RNAi construct" is a generic term used throughout the specification to include small interfering RNAs (siRNAs), hairpin RNAs, and other RNA species, which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences.

The choice of promoter and other regulatory elements generally varies according to the intended host cell. In general, expression vectors of utility in recombinant DNA techniques are often in the form of "plasmids" which refer to circular double stranded DNA loops, which, in their vector form are not bound to the chromosome. In the present specification, "plasmid" and "vector" are used interchangeably as the plasmid is the most commonly used form of vector. However, the application describes other forms of expression vectors that serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, embodiments tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, a modified ribonucleotide can be introduced by in vitro enzymatic or organic synthesis.

Methods of chemically modifying RNA molecules can be adapted for modifying RNAi constructs (see for example, *Nucleic Acids Res,* 25:776-780; *J Mol Recog* 7:89-98; *Nucleic Acids Res* 23:2661-2668; Antisense *Nucleic Acid Drug Dev* 7:55-61). Merely to illustrate, the backbone of an RNAi construct can be modified with phosphorothioates, phosphoramidate, phosphodithioates, chimeric methylphosphonate-phosphodie-sters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount, which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules described herein can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (*Proc Natl Acad Sci USA*, 98:9742-9747; *EMBO J*, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, *Genes Dev*, 2002, 16:948-58; *Nature*, 2002, 418:38-9; RNA, 2002, 8:842-50; and *Proc Natl Acad Sci*, 2002, 99:6047-52. Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an example of a vector for bi-directional transcription of a transgene to yield both sense and antisense RNA transcripts of the same transgene in a eukaryotic cell. Accordingly, certain embodiments provide a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

In some embodiments, a lentiviral vector can be used for the long-term expression of a siRNA, such as a short-hairpin RNA (shRNA), to knockdown expression of the RPTP in a cancer cell. Although there have been some safety concerns about the use of lentiviral vectors for gene therapy, self-inactivating lentiviral vectors are considered good candidates for gene therapy as they readily transfect mammalian cells.

By way of example, short-hairpin RNA (shRNA) down regulation of the AKR1A1 expression can be created using OligoEngene software (OligoEngine, Seattle, Wash.) to identify sequences as targets of siRNA. The oligo sequences can be annealed and ligated into linearized pSUPER RNAi vector (OligoEngine, Seattle, Wash.) and transformed in *E coli* strain DH5a cells. After positive clones are selected, plasmid can be transfected into 293T cells by calcium precipitation. The viral supernatant collected containing shRNA can then be used to infect mammalian cells in order to down regulate the AKR1A1.

AKR1A1 siRNA, shRNA plasmids, and shRNA lentiviral particle gene silencers are commercially available from Santa Cruz Biotechnology under the product names sc-78566, sc-78566-SH, and sc-78566-V.

In another embodiment, the the ADH inhibitor, AKR inhibitor, SCoR inhibitor, and/or PKM2 inhibitor inhibitor can include antisense oligonucleotides. Antisense oligonucleotides are relatively short nucleic acids that are complementary (or antisense) to the coding strand (sense strand) of the mRNA encoding a particular protein. Although antisense oligonucleotides are typically RNA based, they can also be DNA based. Additionally, antisense oligonucleotides are often modified to increase their stability.

The binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their administration to a cell or tissue allows the degradation of the mRNA encoding a specific protein. Accordingly, antisense oligonucleotides decrease the expression and/or activity of a particular protein (e.g., AKR1A1).

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups, such as peptides (e.g., for targeting host cell receptors), or agents facilitating transport across the cell membrane (see, e.g., *Proc Natl Acad Sci* 86:6553-6556; *Proc Natl Acad Sci* 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents (See, e.g., *BioTechniques* 6:958-976) or intercalating agents. (See, e.g., *Pharm Res* 5:539-549). To this end, the oligonucleotide may be conjugated or coupled to another molecule.

Oligonucleotides described herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (*Nucl. Acids Res.* 16:3209), methylphosphonate oligonucleotides can be prepared by use of controlled pore glass polymer supports (*Proc Natl Acad Sci* 85:7448-7451).

The selection of an appropriate oligonucleotide can be performed by one of skill in the art. Given the nucleic acid sequence encoding a particular protein, one of skill in the art can design antisense oligonucleotides that bind to that protein, and test these oligonucleotides in an in vitro or in vivo system to confirm that they bind to and mediate the degradation of the mRNA encoding the particular protein. To design an antisense oligonucleotide that specifically binds to and mediates the degradation of a particular protein, it is important that the sequence recognized by the oligonucleotide is unique or substantially unique to that particular protein. For example, sequences that are frequently repeated across protein may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific or substantially specific for a particular protein.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense oligonucleotide sufficient to suppress translation on endogenous mRNAs in certain instances. Therefore, another approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells.

Expression of the sequence encoding the antisense RNA can be by a promoter known in the art to act in mammalian, preferably human cells. Such promoters can be inducible or constitutive. Such promoters include but are not limited to: the SV40 early promoter region (*Nature* 290:304-310), the promoter contained in the 3' long terminal repeat of Rous sarcoma vims (*Cell* 22:787-797), the herpes thymidine kinase promoter (*Proc Natl Acad Sci* 78:1441-1445), the regulatory sequences of the metallothionein gene (*Nature* 296:39-42), etc. A type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

In some embodiments, the ADH inhibitor, AKR inhibitor, SCoR inhibitor, and/or PKM2 inhibitor can be provided in pharmaceutical compositions with at least one pharmaceutically acceptable carrier. Suitable carriers are described in "Remington: The Science and Practice, Twentieth Edition," published by Lippincott Williams & Wilkins, which is incorporated herein by reference. Pharmaceutical compositions according to the invention may also comprise one or more non-inventive compound active agents.

The compositions comprising ADH inhibitor, AKR inhibitor, SCoR inhibitor, and/or PKM2 inhibitor can be utilized in any pharmaceutically acceptable dosage form, including, but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the ADH inhibitor, AKR inhibitor, SCoR inhibitor, and/or PKM2 inhibitor can be formulated: (a) for administration selected from the group consisting of oral, pulmonary, intravenous, intra-arterial, intrathecal, intra-articular, rectal, ophthalmic, colonic, parenteral, intracisternal, intravaginal, intraperitoneal, local, buccal, nasal, and topical administration; (b) into a dosage form selected from the group consisting of liquid dispersions, gels, aerosols, ointments, creams, tablets, sachets, and capsules; (c) into a dosage form selected from the group consisting of lyophilized formulations, dry powders, fast melt formulations, controlled release formulations, delayed release formulations, extended release formulations, pulsatile release formulations, and mixed immediate release and controlled release formulations; or (d) any combination thereof.

Solutions or suspensions used for parenteral, intradermal, or subcutaneous application can comprise one or more of the following components: (1) a sterile diluents, such as water for injection, saline solution, fixed oils, polyethylene glycols, glycerine, propylene glycol, or other synthetic solvents; (2) antibacterial agents, such as benzyl alcohol or methyl parabens; (3) antioxidants, such as ascorbic acid or sodium bisulfite; (4) chelating agents, such as ethylenediaminetetraacetic acid; (5) buffers, such as acetates, citrates, or phosphates; and (5) agents for the adjustment of tonicity, such as sodium chloride or dextrose. The pH can be adjusted with acids or bases, such as hydrochloric acid or sodium hydroxide. A parenteral preparation can be enclosed in ampoules, disposable syringes, or multiple dose vials made of glass or plastic.

Pharmaceutical compositions suitable for injectable use may comprise sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.), or phosphate buffered saline (PBS). In all cases, the composition must be sterile and should be fluid to the extent that easy syringability exists. The pharmaceutical composition should be stable under the conditions of manufacture and storage and should be preserved against the contaminating action of microorganisms such as bacteria and fungi.

The carrier can be a solvent or dispersion medium comprising, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent in the required amount in an appropriate solvent with one or a combination of ingredients enumerated above, as required, followed by filtered sterilization. Generally, dispersions are prepared by incorporating at least one compound of the invention into a sterile vehicle that contains a basic dispersion medium and any other required ingredients. In the case of sterile powders for the preparation of sterile injectable solutions, exemplary methods of preparation include vacuum drying and freeze-drying, both of which yield a powder of a compound of the invention plus any additional desired ingredient from a previously sterile-filtered solution thereof.

Oral compositions generally include an inert diluent or an edible carrier. They can be enclosed, for example, in gelatin capsules or compressed into tablets. For the purpose of oral therapeutic administration, the compound of the invention can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from pressured container or dispenser that contains a suitable propellant, e.g., a gas, such as carbon dioxide, a nebulized liquid, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In one embodiment, the ADH inhibitors, AKR inhibitors, SCoR inhibitors, and/or PKM2 inhibitors can be prepared with carriers that will protect against rapid elimination from the body. For example, a controlled release formulation can be used, including implants and microencapsulated delivery systems. Biodegradable, biocompatible polymers can be used, such as ethylene vinyl acetate, poly anhydrides, poly glycolic acid, collagen, poly orthoesters, and polylactic acid. Methods for preparation of such formulations will be apparent to those skilled in the art.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of the compounds described herein may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of the compound of the invention calculated to produce the desired therapeutic effect in association with the required pharmaceutical carrier. The specification for the dosage unit forms of the invention are dictated by and directly dependent on the unique characteristics of the compound of the invention and the particular therapeutic effect to be achieved, and the limitations inherent in the art of compounding such an active agent for the treatment of individuals.

Pharmaceutical compositions, which include the ADH inhibitors, AKR inhibitors, SCoR inhibitors, and/or PKM2 inhibitors, may be formulated into various dosage forms as discussed above and then administered through various routes including an oral, inhalational, transdermal, subcutaneous, intravenous or intramuscular route. The dosage can be a pharmaceutically or therapeutically effective amount.

Therapeutically effective dosage amounts of the ADH inhibitors, AKR inhibitors, SCoR inhibitors, and/or PKM2 inhibitors may be present in varying amounts in various embodiments. For example, in some embodiments, a therapeutically effective amount of the ADH inhibitors, AKR inhibitors, SCoR inhibitors, and/or PKM2 inhibitors may be an amount ranging from about 10-1000 mg (e.g., about 20 mg-1,000 mg, 30 mg-1.000 mg, 40 mg-1,000 mg, 50 mg-1,000 mg, 60 mg-1,000 mg, 70 mg-1,000 mg, 80 mg-1.000 mg, 90 mg-1,000 mg, about 10-900 mg, 10-800 mg, 10-700 mg, 10-600 mg, 10-500 mg, 100-1000 mg, 100-900 mg, 100-800 mg, 100-700 mg, 100-600 mg, 100-500 mg, 100-400 mg, 100-300 mg, 200-1000 mg, 200-900 mg, 200-800 mg, 200-700 mg, 200-600 mg, 200-500 mg, 200-400 mg, 300-1000 mg, 300-900 mg, 300-800 mg, 300-700 mg, 300-600 mg, 300-500 mg, 400 mg-1,000 mg, 500 mg-1,000 mg, 100 mg-900 mg, 200 mg-800 mg, 300 mg-700 mg, 400 mg-700 mg, and 500 mg-600 mg). In some embodiments, the ADH inhibitor, AKR inhibitor, SCoR inhibitor, and/or PKM2 inhibitor is present in an amount of or greater than about 10 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg. In some embodiments, the ADH inhibitor, AKR inhibitor, SCoR inhibitor, and/or PKM2 inhibitor is present in an amount of or less than about 1000 mg, 950 mg, 900 mg, 850 mg, 800 mg, 750 mg, 700 mg, 650 mg, 600 mg, 550 mg, 500 mg, 450 mg, 400 mg, 350 mg, 300 mg, 250 mg, 200 mg, 150 mg, or 100 mg.

In other embodiments, a therapeutically effective dosage amount may be, for example, about 0.001 mg/kg weight to 500 mg/kg weight, e.g., from about 0.001 mg/kg weight to 400 mg/kg weight, from about 0.001 mg/kg weight to 300 mg/kg weight, from about 0.001 mg/kg weight to 200 mg/kg weight, from about 0.001 mg/kg weight to 100 mg/kg weight, from about 0.001 mg/kg weight to 90 mg/kg weight, from about 0.001 mg/kg weight to 80 mg/kg weight, from about 0.001 mg/kg weight to 70 mg/kg weight, from about 0.001 mg/kg weight to 60 mg/kg weight, from about 0.001 mg/kg weight to 50 mg/kg weight, from about 0.001 mg/kg weight to 40 mg/kg weight, from about 0.001 mg/kg weight to 30 mg/kg weight, from about 0.001 mg/kg weight to 25 mg/kg weight, from about 0.001 mg/kg weight to 20 mg/kg weight, from about 0.001 mg/kg weight to 15 mg/kg weight, from about 0.001 mg/kg weight to 10 mg/kg weight.

In still other embodiments, a therapeutically effective dosage amount may be, for example, about 0.0001 mg/kg weight to 0.1 mg/kg weight, e.g. from about 0.0001 mg/kg weight to 0.09 mg/kg weight, from about 0.0001 mg/kg weight to 0.08 mg/kg weight, from about 0.0001 mg/kg weight to 0.07 mg/kg weight, from about 0.0001 mg/kg weight to 0.06 mg/kg weight, from about 0.0001 mg/kg weight to 0.05 mg/kg weight, from about 0.0001 mg/kg weight to about 0.04 mg/kg weight, from about 0.0001 mg/kg weight to 0.03 mg/kg weight, from about 0.0001 mg/kg weight to 0.02 mg/kg weight, from about 0.0001 mg/kg weight to 0.019 mg/kg weight, from about 0.0001 mg/kg weight to 0.018 mg/kg weight, from about 0.0001 mg/kg weight to 0.017 mg/kg weight, from about 0.0001 mg/kg weight to 0.016 mg/kg weight, from about 0.0001 mg/kg weight to 0.015 mg/kg weight, from about 0.0001 mg/kg weight to 0.014 mg/kg weight, from about 0.0001 mg/kg weight to 0.013 mg/kg weight, from about 0.0001 mg/kg weight to 0.012 mg/kg weight, from about 0.0001 mg/kg weight to 0.011 mg/kg weight, from about 0.0001 mg/kg weight to 0.01 mg/kg weight, from about 0.0001 mg/kg weight to 0.009 mg/kg weight, from about 0.0001 mg/kg weight to 0.008 mg/kg weight, from about 0.0001 mg/kg weight to 0.007 mg/kg weight, from about 0.0001 mg/kg weight to 0.006 mg/kg weight, from about 0.0001 mg/kg weight to 0.005 mg/kg weight, from about 0.0001 mg/kg weight to 0.004 mg/kg weight, from about 0.0001 mg/kg weight to 0.003 mg/kg weight, from about 0.0001 mg/kg weight to 0.002 mg/kg weight. In some embodiments, the therapeutically effective dose may be 0.0001 mg/kg weight, 0.0002 mg/kg weight, 0.0003 mg/kg weight, 0.0004 mg/kg weight, 0.0005 mg/kg weight, 0.0006 mg/kg weight, 0.0007 mg/kg weight, 0.0008 mg/kg weight, 0.0009 mg/kg weight, 0.001 mg/kg weight, 0.002 mg/kg weight, 0.003 mg/kg weight, 0.004 mg/kg weight, 0.005 mg/kg weight, 0.006 mg/kg weight, 0.007 mg/kg weight, 0.008 mg/kg weight, 0.009 mg/kg weight, 0.01 mg/kg weight, 0.02 mg/kg weight, 0.03 mg/kg weight, 0.04 mg/kg weight, 0.05 mg/kg weight, 0.06 mg/kg weight, 0.07 mg/kg weight, 0.08 mg/kg weight, 0.09 mg/kg weight, or 0.1 mg/kg weight. The effective dose for a particular individual can be varied (e.g., increased or decreased) over time, depending on the needs of the individual.

In some embodiments, a therapeutically effective dosage may be a dosage of 10 μg/kg/day, 50 μg/kg/day, 100 μg/kg/day, 250 μg/kg/day, 500 μg/kg/day, 1000 μg/kg/day or more. In various embodiments, the amount of the the ADH inhibitor, AKR inhibitor, SCoR inhibitor, and/or PKM2 inhibitor or pharmaceutical salt thereof is sufficient to provide a dosage to a patient of between 0.01 μg/kg and 10 μg/kg; 0.1 μg/kg and 5 μg/kg; 0.1 μg/kg and 1000 μg/kg; 0.1 μg/kg and 900 μg/kg; 0.1 μg/kg and 900 μg/kg; 0.1 μg/kg and 800 μg/kg; 0.1 μg/kg and 700 μg/kg; 0.1 μg/kg and 600 μg/kg; 0.1 μg/kg and 500 μg/kg; or 0.1 μg/kg and 400 μg/kg.

Various embodiments may include differing dosing regimen. In some embodiments, the ADH inhibitors, AKR inhibitors, SCoR inhibitors, and/or PKM2 inhibitors can be administered via continuous infusion. In some embodiments, the continuous infusion is intravenous. In other embodiments, the continuous infusion is subcutaneous. The dosing regimen for a single subject need not be at a fixed interval, but can be varied over time, depending on the needs of the subject.

In one aspect, a pharmaceutical composition comprising an effective amount of the ADH inhibitors, AKR inhibitors, SCoR inhibitors, and/or PKM2 inhibitors can be administered at least twice. In another aspect, a pharmaceutical composition is administered at least five times. In yet another aspect, a pharmaceutical composition is administered at least 10 times. One of ordinary skill in the art can determine how often to administer the composition based on the particular disease or disorder being treated or how the subject has responded to prior treatments. One of ordinary skill in the art can also determine when to administer a treatment relative to the time that an ischemic reperfusion injury event occurs, including before, after, or both.

In one embodiment, the subject is treated with the ADH inhibitors, AKR inhibitors, SCoR inhibitors, and/or PKM2 inhibitors prior to the ischemic reperfusion injury event. In one aspect, the subject can be treated starting at least several days before the event or as close to several minutes before the ischemic reperfusion injury event. For example, the ADH inhibitor, AKR inhibitor, SCoR inhibitor, and/or PKM2 inhibitor therapy can begin at about 2 hours, 8 hours, 24 hours, or 26 hours prior to ischemic reperfusion injury. One of ordinary skill in the art will appreciate that the ADH inhibitor, AKR inhibitor, SCoR inhibitor, and/or PKM2 inhibitor can be administered at varying times and not just at about 2, 8, 24, or 26 hours prior to ischemic reperfusion injury. In one aspect, the range of time for treating prior to the ischemic reperfusion injury event can be from about 1.0 minutes to about 72 hours. In another aspect, the range of time for treating prior to the ischemic reperfusion injury event can be from about 10 minutes to about 48 hours. In another aspect, the range of time for treating prior to the ischemic reperfusion injury event can be from about 30 minutes to about 24 hours.

In one embodiment, the subject is treated with the ADH inhibitor, AKR inhibitor, SCoR inhibitor, and/or PKM2 inhibitor after the IRI event or both before and after as described above. In one aspect, the subject can be treated starting immediately thereafter, such as several minutes after the ischemic reperfusion ischemic reperfusion injury event. For example, the ADH inhibitor, AKR inhibitor, SCoR inhibitor, and/or PKM2 inhibitor therapy can begin at about 30 minutes, 2 hours, 8 hours, 24 hours, or 48 hours after the ischemic reperfusion injury. One of ordinary skill in the art will appreciate that the ADH inhibitor, AKR inhibitor, SCoR inhibitor, and/or PKM2 inhibitor can be administered at varying times as well.

In some embodiments, the ADH inhibitors, AKR inhibitors, SCoR inhibitors, and/or PKM2 inhibitors, including pharmaceutical compositions comprising the the ADH inhibitors, AKR inhibitors, SCoR inhibitors, and/or PKM2 inhibitors, can be used in methods for preventing or treating (e.g., alleviating one or more symptoms of) medical conditions. The methods comprise administering a therapeutically effective amount of the ADH inhibitors, AKR inhibitors, SCoR inhibitors, and/or PKM2 inhibitors to a patient or subject in need thereof. The compositions can also be used for prophylactic therapy.

The subject can be any animal, domestic, livestock, or wild, including, but not limited to cats, dogs, horses, pigs, and cattle, and preferably human patients. As used herein, the terms patient and subject may be used interchangeably.

It will be appreciated that the amount, volume, concentration, and/or dosage of the therapeutic agent that is administered to any one animal or human depends on many factors, including the subject's size, body surface area, age, the particular composition to be administered, sex, time and route of administration, general health, and other drugs being administered concurrently. Specific variations of the above noted amounts, volumes, concentrations, and/or dosages of therapeutic agent can be readily be determined by one skilled in the art using the experimental methods described below.

In other embodiments, the ADH inhibitors, AKR inhibitors, SCoR inhibitors, and/or PKM2 or a pharmaceutically acceptable salt thereof, or a prodrug or metabolite thereof, can be administered in combination with an NO donor, including SNO-CoA, which is shown to have activity in regulating sterol biosynthesis and CoA metabolism. An NO donor donates nitric oxide or a related redox species and more generally provides nitric oxide bioactivity, that is activity which is identified with nitric oxide, e.g., vasorelaxation or stimulation or inhibition of a receptor protein, e.g., ras protein, adrenergic receptor, NFκB. NO donors including S-nitroso, O-nitroso, C-nitroso, and N-nitroso compounds and nitro derivatives thereof and metal NO complexes, but not excluding other NO bioactivity generating compounds, useful herein are described in "Methods in Nitric Oxide Research," Feelisch et al. eds., pages 71-115 (J. S., John Wiley & Sons, New York, 1996), which is incorporated herein by reference. NO donors which are C-nitroso compounds where nitroso is attached to a tertiary carbon which are useful herein include those described in U.S. Pat. No. 6,359,182 and in WO 02/34705. Examples of S-nitroso compounds, including S-nitrosothiols useful herein, include, for example, S-nitrosoglutathione, S-nitroso-N-acetylpenicillamine, S-nitroso-cysteine and ethyl ester thereof, S-nitroso cysteinyl glycine, S-nitroso-gamma-methyl-L-homocysteine, S-nitroso-L-homocysteine, S-nitroso-gamma-thio-L-leucine, S-nitroso-delta-thio-L-leucine, and S-nitrosoalbumin. Examples of other NO donors useful herein are sodium nitroprusside (nipride), ethyl nitrite, isosorbide, nitroglycerin, SIN 1 which is molsidomine, furoxamines, N-hydroxy(N-nitrosamine), and perfluorocarbons that have been saturated with NO or a hydrophobic NO donor. ADH inhibitors, AKR inhibitors, and/or SNO-CoAR inhibitors can also be combined with with R(+) enantiomer of amlodipine, a known NO releaser (Zhang at al., J. Cardiovasc. Pharm. 39: 208-214 (2002)).

Figure 16A:
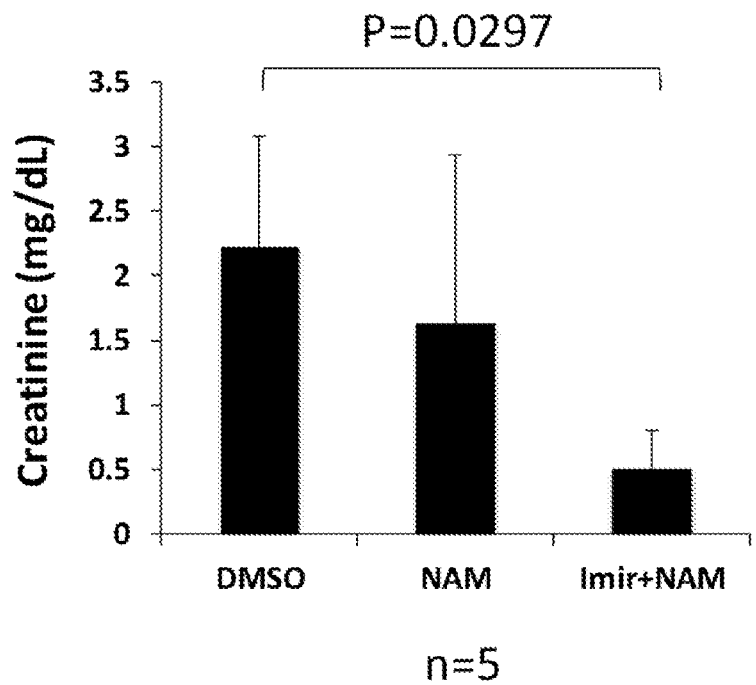
FIGS. 16(*a-b*) illustrate graphs showing the serum creatinine and blood urea nitrogen (BUN) in injury kidneys of mice.
Figure 16B:
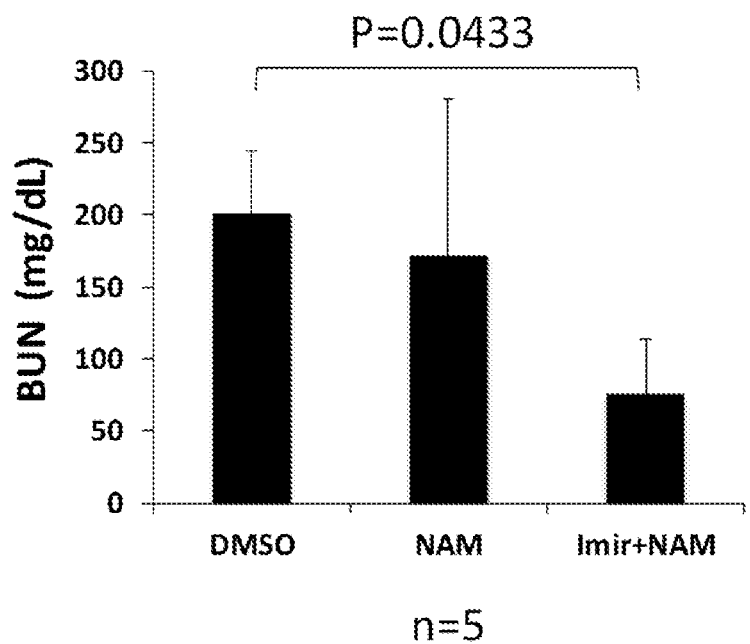

In some embodiments, the ADH inhibitors, AKR inhibitors, SCoR inhibitors, and/or PKM2 can be administered in combination with nicotinamide adenine dinucleotide (NAD$^+$) and/or a NAD$^+$ precursor. Advantageously, as shown in FIGS. 16(A-B), administration of a NAD$^+$ precursor, nicotinamide (NAM), in combination with an AKR inhibitor, imirestat, substantially reduced serum creatinine and blood urea nitrogen (BUN) in injury kidneys of mice compared to control and the administration of nicotinamide alone or imirestat alone (not shown).

In some embodiments, NAD activity may be increased by administration of NAD as well as by synthesizing NAD. NAD may be synthesized through three major pathways, the de novo pathway in which NAD is synthesized from tryptophan, the NAD salvage pathway in which NAD is generated by recycling degraded NAD products, such as nicotinamide, and the nicotinamide riboside kinase pathway in which nicotinamide riboside is converted to nicotinamide mononucleotide by nicotinamide riboside kinase. Thus, the NAD precursors may include one or more of an intermediate of a de novo pathway for synthesizing NAD, an intermediate of a NAD salvage pathway, and an intermediate of a nicotinamide riboside kinase pathway.

In some embodiments, where the NAD precursor includes an intermediate of a de novo pathway for synthesizing NAD, such intermediates may include, without limitation, tryptophan, nicotinic acid, nicotinic acid adenine dinucleotide, nicotinic acid mononucleotide, quinolinic acid, 3-hydroxyanthranilate, 3-hydroxykynurenine, kynurenine, N-formylkynurenine, or a pharmaceutically acceptable salt thereof.

In some embodiments, where the NAD precursor includes an intermediate of a nicotinamide riboside kinase pathway, such intermediates may include, without limitation, nicotinamide, nicotinamide mononucleotide, or a pharmaceutically acceptable salt thereof.

In some embodiments, where the NAD precursor includes an intermediate of a nicotinamide riboside kinase pathway, the intermediate may include, without limitation, nicotinamide riboside, nicotinic acid riboside, or a pharmaceutically acceptable salt thereof.

In some embodiments, the NAD precursor may be selected from the group consisting of tryptophan, nicotinic acid, nicotinic acid riboside, nicotinamide riboside (NR), nicotinamide, and NAD itself, and a pharmaceutically acceptable salt thereof.

In some embodiments, the methods may include administering an inhibitor of NAD consumption. The inhibitor of NAD consumption may include one or more of a poly adp-ribose polymerase (PARP) inhibitor, a CD38 inhibitor, and a pharmaceutically acceptable salt thereof. In some embodiments, a PARP inhibitor may include, but is not limited to, one or more of iodonitrocoumarin, 5-iodo-6-nitrocoumarin, 3,4-dihydro-5-methyl-isoquinolinone 4-amino-1,8-naphthalimide, 3-methoxybenzamide, 8-hydroxy-2-methyl-3-hydro-quinazolin-4-one, 3-(4-chlorophenyl)-quinoxaline-5-carboxamide, 2-(3'-methoxyphenyl)benzimidazole-4-carboxamide, benzamide, 3-aminobenzamide, 3-aminophtalhydrazide, and 1,5-dihydroxyisoquinoline, and the pharmaceutically acceptable salts thereof.

It will also be appreciated that certain selective ADH inhibitors, AKR inhibitors, SCoR inhibitors, and/or PKM2 inhibitors that inhibit some ADHs, AKRs, SCoRs, and/or PKM2 can be administered in combination with other selective ADH inhibitors, AKR inhibitors, SCoR inhibitors, and/or PKM inhibitors that inhibit other ADHs, AKRs, SCoRs, and PKMs. For example, a selective ADH6 inhibitor can be administered in combination with an ADH3 inihibitor.

In other embodiments, ADH inhibitors, AKR inhibitors, SCoR inhibitors, and/or PKM2 inhibitors can be administered in combination with an agent that imposes nitrosative or oxidative stress. Agents for selectively imposing nitrosative stress to inhibit proliferation of pathologically proliferating cells in combination therapy with ADH inhibitors, AKR inhibitors, SCoR inhibitors, and/or PKM2 inhibitors and dosages and routes of administration therefor include those disclosed in U.S. Pat. No. 6,057,367, which is incorporated herein. Supplemental agents for imposing oxidative stress (i.e., agents that increase GSSG (oxidized glutathione) over GSH (glutathione) ratio or NAD(P) over NAD(P)H ratio or increase thiobarbituric acid derivatives) in combination therapy with ADH inhibitors, AKR inhibitors, SCoR inhibitors, and/or PKM2 inhibitors include, for example, L-buthionine-S-sulfoximine (BSO), glutathione reductase inhibitors (e.g., BCNU), inhibitors or uncouplers of mitochondrial respiration, and drugs that increase reactive oxygen species (ROS), e.g., adriamycin, in standard dosages with standard routes of administration.

In some embodiments, the ADH inhibitors, AKR inhibitors, SCoR inhibitors, and/or PKM2 inhibitors may also be co-administered with a phosphodiesterase inhibitor (e.g., rolipram, cilomilast, roflumilast, VIAGRA (sildenifil citrate), CLALIS (tadalafil), LEVITRA (vardenifil), etc.), a β-agonist, a steroid, or a leukotriene antagonist (LTD-4). Those skilled in the art can readily determine the appropriate therapeutically effective amount depending on the disorder to be ameliorated.

The ADH inhibitors, AKR inhibitors, SCoR inhibitors, and/or PKM2 inhibitors described herein can be used to treat, prevent, or reduce the symptoms or severity of acute kidney injury in a subject (e.g., a human subject) in need thereof. The ADH inhibitors, AKR inhibitors, SCoR inhibitors, and/or PKM2 inhibitors are also useful in preventing the development of chronic kidney disease in a subject in need thereof. In certain embodiments, the ADH inhibitors, AKR inhibitors, SCoR inhibitors, and/or PKM2 inhibitors are useful in preventing the development of chronic kidney disease in a subject in need thereof following an insult that can cause or causes acute kidney injury. In addition, the ADH inhibitors, AKR inhibitors, SCoR inhibitors, and/or PKM2 inhibitors described herein can be used in methods for protecting a kidney from acute or chronic kidney injury in a subject in need thereof. Furthermore, the ADH inhibitors, AKR inhibitors, SCoR inhibitors, and/or PKM2 inhibitors described herein can be used in methods for treating patients with renal insufficiency or renal failure, attributable at least in part to use of a drug or chemical.

Acute kidney injury is commonly divided into two major categories based on the type of insult. The first category is ischemic acute kidney injury (alternatively referred to as kidney hypoperfusion) and the second category is nephrotoxic acute kidney injury. The former results from impaired blood flow (kidney hypoperfusion) and oxygen delivery to the kidney; whereas, the latter results from a toxic insult to the kidney. Both of these categories of insults can lead to a secondary condition called acute tubular necrosis (ATN).

The most common causes of ischemic acute kidney injury are intravascular volume depletion, reduced cardiac output, systemic vasodilatation, and renal vasoconstriction. Intravascular volume depletion can be caused by hemorrhage (e.g., following surgery, postpartum, or trauma); gastrointestinal loss (e.g., from diarrhea, vomiting, nasogastric loss); renal losses (e.g., caused by diuretics, osmotic diuresis, diabetes insipidus); skin and mucous membrane losses (e.g., burns, hyperthermia); nephrotic syndrome; cirrhosis; or capillary leak. Reduced cardiac output can be due to cardiogenic shock, pericardial disease (e.g. restrictive, constrictive, tamponade), congestive heart failure, valvular heart disease, pulmonary disease (e.g., pulmonary hypertension, pulmonary embolism), or sepsis. Systemic vasodilation can be the result of cirrhosis, anaphylaxis, or sepsis. Finally, renal vasoconstriction can be caused by early sepsis, hepatorenal syndrome, acute hypercalcemia, drug-related (e.g., norepinephrine, vasopressin, nonsteroidal anti-inflammatory drugs, angiotensin-converting enzyme inhibitors, calcineurin inhibitors), or use of a radiocontrast agent. The ADH inhibitors, AKR inhibitors, SCoR inhibitors, and/or PKM2 inhibitors described herein can be used to treat or reduce the symptoms or severity of acute kidney injury or any other kidney injury caused by any of the above-mentioned causes of ischemic acute kidney injury. In addition, the ADH inhibitors, AKR inhibitors, SCoR inhibitors, and/or PKM2 inhibitors thereof described herein can be used to prevent the development of acute kidney injury or any other kidney injury following exposure to the above-mentioned causes of ischemic acute kidney injury.

Nephrotoxic acute kidney injury is often associated with exposure to a nephrotoxin such as a nephrotoxic drug. Examples of nephrotoxic drugs include an antibiotic (e.g., aminoglycosides such as gentamicin), a chemotherapeutic agent (e.g., cis-platinum), a calcineurin inhibitor (e.g., tacrolimus, cyclosporine), cephalosporins such as cephaloridine, cyclosporin, pesticides (e.g., paraquat), environmental contaminants (e.g., trichloroethylene, dichloroacetylene), amphotericin B, puromcyin, aminonucleoside (PAN), a radiographic contrast agent (e.g., acetrizoate, diatrizoate, iodamide, ioglicate, iothalamate, ioxithalamate, metrizoate, metrizamide, iohexol, iopamidol, iopentol, iopromide, and ioversol), a nonsteroidal anti-inflammatory, an anti-retroviral, an immunosuppressant, an oncological drug, or an ACE inhibitor. A nephrotoxin can be, for example, a trauma injury, a crush injury, an illicit drug, analgesic abuse, a gunshot wound, or a heavy metal. The ADH inhibitors, AKR inhibitors, SCoR inhibitors, and/or PKM2 inhibitors described herein can be used to treat or reduce the symptoms or severity of acute kidney injury or any other kidney injury caused by any of the above-mentioned causes of nephrotoxic acute kidney injury. In addition, the ADH inhibitors, AKR inhibitors, SCoR inhibitors, and/or PKM2 inhibitors described herein can be used to prevent the development of acute kidney injury or any other kidney injury following exposure to the above-mentioned causes of nephrotoxic acute kidney injury.

In certain embodiments, the ADH inhibitors, AKR inhibitors, SCoR inhibitors, and/or PKM2 inhibitors described herein can be used to prevent the development of ATN following exposure to an insult such as ischemia or nephrotoxins/nephrotoxic drugs. In certain embodiments, the ADH inhibitors, AKR inhibitors, SCoR inhibitors, and/or PKM2 inhibitors described herein can be used to treat or reduce the symptoms or severity of ATN following ischemia or exposure to nephrotoxins/nephrotoxic drugs.

In certain embodiments, the ADH inhibitors, AKR inhibitors, SCoR inhibitors, and/or PKM2 inhibitors described herein can be used to prevent a drop in glomerular filtration following ischemia or exposure to nephrotoxins/nephrotoxic drugs. In some embodiments, the ADH inhibitors, AKR inhibitors, SCoR inhibitors, and/or PKM2 inhibitors can be used to prevent tubular epithelial injury and/or necrosis following ischemia or exposure to nephrotoxins/nephrotoxic drugs. In some embodiments, the ADH inhibitors, AKR inhibitors, SCoR inhibitors, and/or PKM2 inhibitors can be used to decrease the microvascular permeability, improve vascular tone, and/or reduce inflammation of endothelial cells. In other embodiments, the ADH inhibitors, AKR inhibitors, SCoR inhibitors, and/or PKM2 inhibitors described herein can be used to restore blood flow in the kidney following ischemia or exposure to nephrotoxins/nephrotoxic drugs. In further embodiments, the ADH inhibitors, AKR inhibitors, SCoR inhibitors, and/or PKM2 inhibitors described herein can be used to prevent chronic renal failure.

The ADH inhibitors, AKR inhibitors, SCoR inhibitors, and/or PKM2 inhibitors described herein can also be used to treat or prevent acute kidney injury resulting from surgery complicated by hypoperfusion. In certain specific embodiments, the surgery is one of cardiac surgery, major vascular surgery, major trauma, or surgery associated with treating a gunshot wound. In one embodiment, the cardiac surgery is coronary artery bypass grafting (CABG). In another embodiment, the cardiac surgery is valve surgery.

In some embodiments, the ADH inhibitors, AKR inhibitors, SCoR inhibitors, and/or PKM2 inhibitors described herein can be used to treat or prevent acute kidney injury following organ transplantation such as kidney transplantation or heart transplantation.

In some embodiments, the ADH inhibitors, AKR inhibitors, SCoR inhibitors, and/or PKM2 inhibitors described herein can be used to treat or prevent acute kidney injury following reduced effective arterial volume and kidney hypoperfusion.

In some embodiments, the ADH inhibitors, AKR inhibitors, SCoR inhibitors, and/or PKM2 inhibitors described herein can be used to treat or prevent acute kidney injury in a subject who is taking medication (e.g., an anticholinergic) that interferes with normal emptying of the bladder. In certain embodiments, the ADH inhibitors, AKR inhibitors, SCoR inhibitors, and/or PKM2 inhibitors described herein can be used to treat or prevent acute kidney injury in a subject who has an obstructed urinary catheter. In some embodiments, the ADH inhibitors, AKR inhibitors, SCoR inhibitors, and/or PKM2 inhibitors described herein can be used to treat or prevent acute kidney injury in a subject who is taking a drug that causes crystalluria. In some embodiments, the ADH inhibitors, AKR inhibitors, SCoR inhibitors, and/or PKM2 inhibitors described herein can be used to treat or prevent acute kidney injury in a subject who is taking a drug that causes or leads to myoglobinuria. In some embodiments, the ADH inhibitors, AKR inhibitors, SCoR inhibitors, and/or PKM2 inhibitors described herein can be used to treat or prevent acute kidney injury in a subject who is taking a drug that causes or leads to cystitis.

In some embodiments, the ADH inhibitors, AKR inhibitors, SCoR inhibitors, and/or PKM2 inhibitors described herein can be used to treat or prevent acute kidney injury in a subject who has benign prostatic hypertrophy or prostate cancer.

In some embodiments, the ADH inhibitors, AKR inhibitors, SCoR inhibitors, and/or PKM2 inhibitors described herein can be used to treat or prevent acute kidney injury in a subject who has a kidney stone.

In some embodiments, the ADH inhibitors, AKR inhibitors, SCoR inhibitors, and/or PKM2 inhibitors described herein can be used to treat or prevent acute kidney injury in a subject who has an abdominal malignancy (e.g., ovarian cancer, colorectal cancer).

In certain embodiments, the ADH inhibitors, AKR inhibitors, SCoR inhibitors, and/or PKM2 inhibitors described herein can be used to treat or prevent acute kidney injury, wherein sepsis does not cause or result in the acute kidney injury.

Acute kidney injury typically occurs within hours to days following the original insult (e.g., ischemia or nephrotoxin insult). Thus, ADH inhibitors, AKR inhibitors, SCoR inhibitors, and/or PKM2 inhibitors described herein can be administered before the insult, or within an hour to 30 days (e.g., 0.5 hours, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 8 days, 9 days, 10 days, 11 days, 12 days, 13 days, 15 days, 20 days, 25 days, 28 days, or 30 days) after the insult (e.g., a surgery or nephrotoxin insult described herein).

A subject can be determined to have, or have the risk of developing, acute kidney injury based on, e.g., the Risk Injury Failure Loss ESRD (RIFLE) criteria or the Acute Kidney Injury Network criteria (Bagshaw et al., Nephrol. Dial. Transplant., 23 (5): 1569-1574 (2008); Lopes et al., Clin. Kidney J., 6(1):8-14 (2013)).

In certain embodiments, the methods of this disclosure involve determining measuring the levels of one or more of: serum, plasma or urine creatinine or blood urea nitrogen (BUN); measuring the levels of serum or urine neutrophil gelatinase-associated lipocalin (NGAL), serum or urine interleukin-18 (IL-18), serum or urine cystatin C, or urine KIM-1, compared to a healthy control subject, to assess whether the subject has, or has a risk of developing, acute kidney injury.

The efficacy of the ADH inhibitors, AKR inhibitors, SCoR inhibitors, and/or PKM2 inhibitors can be assessed in various animal models. Animal models for acute kidney injury include those disclosed in e.g., Heyman et al., Contrin. Nephrol., 169:286-296 (2011); Heyman et al., Exp. Opin. Drug Disc., 4(6): 629-641 (2009); Morishita et al., Ren. Fail., 33(10):1013-1018 (2011); Wei Q et al., Am. J. Physiol. Renal Physiol., 303(11):F1487-94 (2012).

The efficacy of treatments may be measured by a number of available diagnostic tools, including physical examination, blood tests, measurements of blood systemic and capillary pressure, proteinuria (e.g., albuminuria), microscopic and macroscopic hematuria, assessing serum creatinine levels, assessment of the glomerular filtration rate, histological evaluation of renal biopsy, urinary albumin creatinine ratio, albumin excretion rate, creatinine clearance rate, 24-hour urinary protein secretion, and renal imaging (e.g., MRI, ultrasound).

In other embodiments, the amount of the ADH inhibitors, AKR inhibitors, SCoR inhibitors, and/or PKM2 inhibitors administered to the subject can be an amount effective to induce renal vasodilatation, enhance resistance to hypoxia, improve renal hemodynamics, decrease renal oxidative stress, reduce renal inflammation, and preserve renal function.

Because the methods of the invention are useful for treating acute kidney injury and ischemic reperfusion injury, the methods further include treating other diseases and disorders associated with ischemic reperfusion injury and tissue injury.

Example

In this example, we show that the SNO-CoA/SCoR system is highly expressed in renal proximal tubules where it transduces the activity of eNOS in reprogramming of intermediary metabolism, thereby protecting kidneys from acute kidney injury (AKI). Specifically, SCoR deletion in mice ($SCoR^{-/-}$) increased protein S-nitrosylation, protected against AKI and improved survival, whereas renoprotection was lost in $eNOS^{-/-}/SCoR^{-/-}$ mice. Metabolic profiling coupled with unbiased mass spectrometry-based SNO-protein identification revealed that protection by the SNO-CoA/SCoR system is mediated by inhibitory S-nitrosylation of pyruvate kinase M2 (PKM2) through a novel locus of regulation, thereby coordinating fuel utilization (through glycolysis) with survival signaling (through the pentose phosphate shunt) to alleviate oxidative stress. Targeted deletion of PKM2 from mouse proximal tubules recapitulated precisely the protective and mechanistic effects of S-nitrosylation in $SCoR^{-/-}$ mice, whereas Cys-mutant PKM2 refractory to S-nitrosylation negated SNO-CoA bioactivity.

Methods

Mice

Figure 15A:
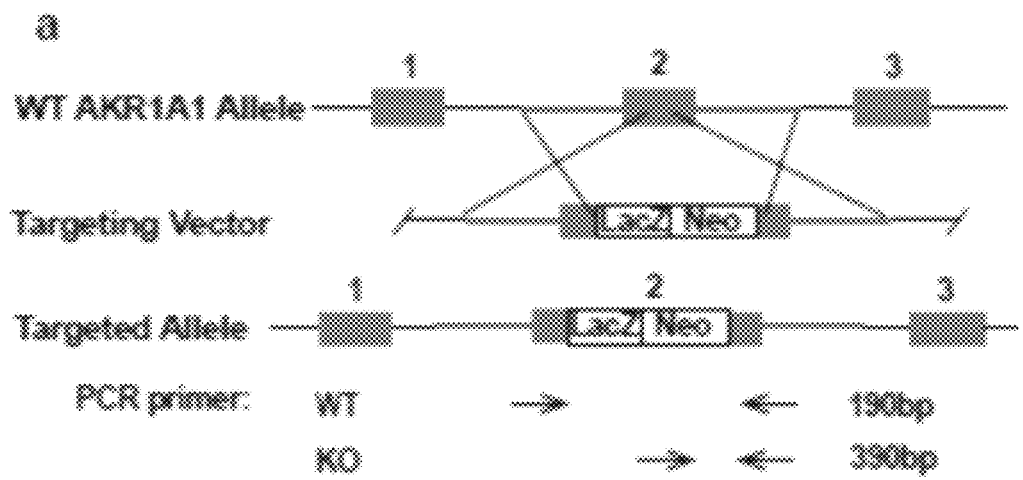
FIGS. 15(*a-c*) illustrate (a) Schema illustrating generation of SCoR$^{-/-}$ mice. (h) PCR amplification of the SCoR gene with genomic DNA isolated from the tails of SCoR (WT), heterozygous SCoR$^{+/-}$ and homozygous SCoR$^{-/-}$ mice. (c) Mortality of SCoR$^{+/+}$, SCoR$^{-/-}$, SCoR$^{-/-}$eNOS$^{-/-}$ and eNOS$^{-/-}$ mice in 24 hour after AKI.
Figure 15B:
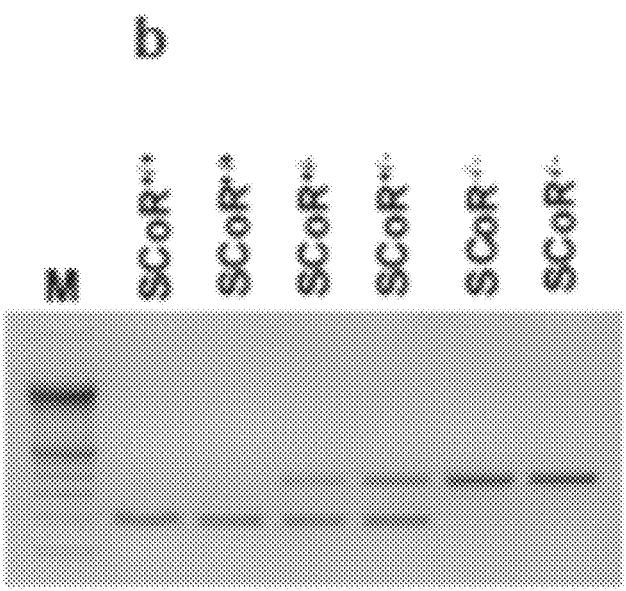
Figure 15C:
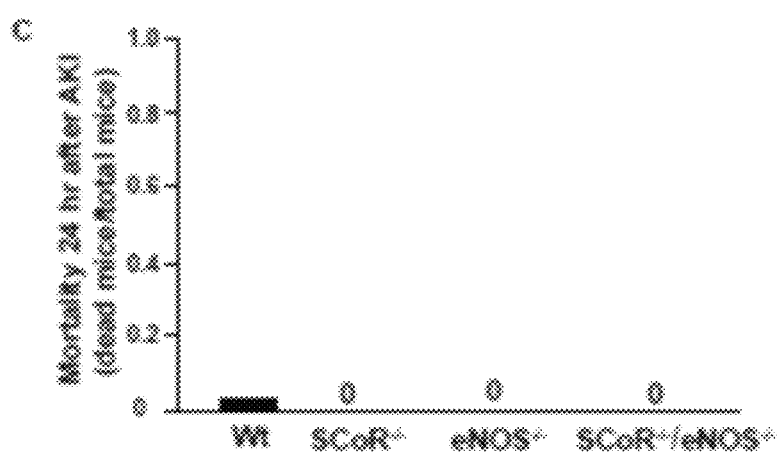

Mouse studies were approved by the Case Western Reserve University Institutional Care and Use Committee (IACUC). Housing and procedures complied with the Guide for the Care and Use of Laboratory Animals and the American Veterinary Medical Association guidelines on euthanasia. SCoR$^{+/-}$ mice were made by Deltagen, Inc. Briefly, to knockout SCoR in ES cells, the SCoR$^{+/-}$ allele was first created by insertion of a LacZ-Neo cassette in place of exon 2 of the SCoR gene, disrupting in-frame translation of SCoR (FIGS. 15a & b). F1 mice were generated by breeding chimeric male mice with C57BL/6 females. F2 homozygous mutant mice were produced by intercrossing F1 heterozygous males and females. Wild-type littermates produced by crossing SCoR$^{+/-}$ and SCoR$^{+/-}$ were used as breeding pairs to generate control mice (SCoR$^{+/+}$). To generate SCoR and eNOS double knockout mice (SCoR$^{-/-}$/eNOS$^{-/-}$), male SCoR$^{-/-}$ mice were crossed with female eNOS$^{-/-}$ mice, obtained from Jackson Laboratory. To generate renal tubular epithelial cell-specific PKM2-knockout mice (PKM2$_{fl/fl}$; KSP-Cre or PKM2$^{-/-}$), conditional PKM2-knockout mice (PKM2$_{fl/fl}$) were crossed with KSP-Cre mice (both obtained from Jackson Laboratory). Wild-type littermates (PKM2$^{+/+}$; KSP-Cre) produced by crossing PKM2$_{fl/+}$; KSP-Cre and PKM2$_{fl/+}$; KSP-Cre were used as breeding pairs to generate control mice. PKM2$_{fl/fl}$ mice possess loxP sites flanking exon 10 of the PKM gene, which when deleted forces PKM transcripts to splice as PKM1. In KSP-Cre mice, the cadherin 16 promoter drives Cre to specifically express in epithelial cells of renal tubules.

Acute Kidney Injury (AKI)

AKI surgery was carried out as described herein. Mice of similar age (9-11 weeks) and body weight (male: 25-28 g; female: 22-25 g) were used for surgery. The mice were anesthetized with isoflurane (1-3%) in oxygen and then anesthesia was maintained with isoflurane (0.75-2.0%) and adjusted as needed. The fur in the surgical area was removed with clippers and the skin sterilized with 3 times alternating washes of betadine (chlorhexidine) and alcohol. The mouse was placed on a thermostatic station during surgery. The skin and muscle were cut open along the back to expose both right and left kidneys. Gentle blunt dissection was performed through muscular layers to reveal the kidney and a Q-tip was used to mobilize and exteriorize the kidney. A 5-0 silk suture was used to clamp the pedicle to block the blood flow to the kidney to induce renal ischemia for 23 min in male mice or 50 min in female mice, then the sutures released to allow reperfusion. The identical steps were performed on the contra-lateral side. A silk suture was used to close the muscle layer of the incision followed by the closure of the skin wound with vicryl. Immediately after the wound closure, 10-20 ml/kg sterile saline was given intraperitoneally to each mouse. The animal was then kept on a heating pad until it gained full consciousness before being returned to home cage. Mice subjected to surgery without clamping the pedicle were used as sham control. Mortality in 24 hour after AKI for WT, SCoR$^{-/-}$, SCoR$^{-/-}$/eNOS$^{-/-}$ and eNOS$^{-/-}$ mice is shown in Supplementary FIG. 1c. Seram creatinine and BUN were determined after 24 hrs of reperfusion upon removal of the kidney (when larger volumes of blood can be collected). Seram creatinine and BUN were measured at University Hospital's Clinical Laboratories.

For the LPS-induced AKI model, LPS (O111:B4, sigma) in saline (0.9%) was injected intraperitoneally to each mouse (10 mg/kg). Immediately after the injection of LPS, 10-20 ml/kg sterile saline was given intraperitoneally to each mouse. Serum creatinine and BUN were determined after 16 hrs.

SNO-RAC

SNO-RAC was carried out as described herein. Mouse kidneys were mechanically homogenized in lysis buffer (1 mg/5 µl lysis buffer) containing 100 mM Hepes/1 mM EDTA/100 µM neocuproine (HEN), 50 mM NaCl, 0.1% (vol/vol) Nonidet P-40, the thiol-blocking agent 0.2% S-methylmethanethiosulfonate (MMTS), 1 mM PMSF and protease inhibitors (Roche). After centrifugation (20,000 g, 4° C., 20 min, ×2), SDS and MMTS were added to the supernatants to 2.5% and 0.2% respectively, and incubated at 50° C. for 20 min. Proteins were precipitated with −20° C. acetone, and re-dissolved in 1 mL of HEN/1% SDS. Precipitation of proteins were repeated with −20° C. acetone, and the final pellets were resuspended in HEN/1% SDS and protein concentrations determined using the Bicinchoninic Acid (BCA) method. Total lysates (2 mg) were incubated with freshly prepared 50 mM ascorbate and 50 µl thiopropyl-Sephareose (50% slurry) and rotated end-over-end in the dark for 4 h. The bound SNO proteins were sequentially washed with HEN/1% SDS and 10% HEN/0.1% SDS; SNO proteins were then eluted with 10% HEN/1% SDS/10% β-meracaptoethanol and analyzed by SDS/PAGE and immunoblotting.

iTRAQ-Coupled SNO-RAC iTRAQ-Coupled SNO-RAC was carried out as described herein. Extracts of kidney were prepared, and SNO-RAC (4 mg of protein per sample) was carried out as described above. SDS/PAGE gels were Coomassie-stained, and lanes were separated into eight segments top-to-bottom and collected to two 1.5 ml tubes. 500 µl of 50% Acetonitrile (ACN)/50% 100 mM ammonium bicarbonate were used to wash gel bands for more than 5 hours while vortexing. After removal of washing buffer, 400 µl of 100% acetonitrile was added to gel pieces and vortexed for 10 min. After removal of ACN, gel pieces were dried in a speed vacuum dryer for 10 mins. 200 µl of 10 mM dithiothreitol (DTT) were added to dry gel pieces and vortexed for 45 mins. 200 µl of 55 mM iodoacetamide (IAA) were added to the gel pieces after removal of DTT buffer, incubating for 45 min at dark. After removal of IAA buffer, 400 µl of 1×iTRAQ dissolution solution and 400 µl ACN were used to wash the gel pieces alternatively for two times. Gel pieces were dried for 10 min in a speed vacuum dryer. 500 ng trypsin in 150 µl 1×iTRAQ buffer were added to dried gel pieces on ice for 30 mins, and then incubated overnight at 37° C. Supernatant from the digested protein solution was transferred to a 1.5 ml tube using gel-loading tips. 200 µl extraction buffer of 60% ACN/5% formic acid were added to gel pieces, vortexed for 30 min, and sonicated for 15 min. The supernatant containing peptide extracts was transferred to 1.5 ml tube, and extractions were repeated two more times. The final digested solution was dried completely. iTRAQ labeling was performed according to the instructions of iTRAQ® Reagents—4plex Applications Kit. Briefly, 30 µl of iTRAQ dissolution buffer (10×) was added to each sample tube (pH>7), and then iTraq labeling reagents (114, 115, 116, 117) to separate sample tubes: one reagent to one sample tube. Labeling reactions were vortexed for more than 5 hours at room temperature to ensure complete labeling efficiency. The four labeled samples were mixed together and dried. 160 µl of 5% ACN containing 0.5% TFA was added to the mixed labeled sample and cleaned using C18 ziptips. Briefly, C18 tips were wetted 5 times by 20 µl of 50% ACN each time, equilibrated by 100 µl of 5% ACN containing 0.5% TFA. Samples were then loaded to the tip by drawing and expelling 50 cycles to ensure complete binding. The tips were then washed by 20 µl of 5% ACN containing 0.5% TFA 10 times. Peptides were eluted from tips by 20 µl of 60% ACN containing 0.1% Formic Acid three times, eluates combined, and dried for LC-MS/MS Analysis.

Immunoprecipitation

15 µg of SCoR polyclonal antibody (Proteintech) was incubated with 50 µl Protein G Sepharose (GE) (1:1 slurry) at 4° C. overnight. After washing with NETN buffer [150 mM NaCl, 20 mM Tris-Cl (pH 8.0), 0.5 mM EDTA, 0.5% (v/v) Nonidet P-40 (NP-40), 1 mM PMSF and protease inhibitors cocktail)] three times, SCoR antibody bound to Protein G Sepharose was ready for immunoprecipitation. Mouse kidneys were mechanically homogenized in EBC lysis buffer [120 mM NaCl, 20 mM Tris-Cl (pH 8.0), 0.5 mM EDT, 0.5% (v/v) NP-40, 1 mM PMSF and protease inhibitors cocktail (1 mg tissue/5 µl lysis buffer)]. After centrifugation (20,000 g, 4° C., 20 min, ×2), 2 ml (2 mg/ml) supernatant was pre-cleared by incubation with 50 µl Protein G Sepharose (1:1 slurry) for 1 hour at 4° C. After spin down at 1000 g for 1 min, the supernatant was transferred into new tubes and incubated with 50 µl anti SCoR antibody-Protein G Sepharose (1:1 slurry) for 5 hours at 4° C. Beads were washed by NETN buffer and proteins were eluted with 50 µl 0.1 M glycine (pH 2.5) for 10 min at room temperature with shaking. Following centrifugation at 1000 g for 2 min, the elution was neutralized by the addition of 5 µl Tris-HCl (1.0 M), pH 8.0. Proteins in elution were identified by LC-MS/MS Analysis. Coimmunoprecipitation (co-IP) was carried out in HEK cells overexpressing V5-SCoR and Myc-PKM2, by co-transfection using Lipofectamine 2000. Cells were collected and lysed in EBC lysis buffer. Anti-Myc affinity gel (Sigma) was used for Co-IP.

LC-MS/MS Analysis

Digested peptides were separated by a UPLC (Waters, Milford, Mass.) with a Nano-ACQUITY UPLC BEH300 C18 column. Separated peptides were continuously injected into an Orbitrap Elite hybrid mass spectrometer (Thermo Finnigan, San Jose, Calif.) by a nanospray emitter (10 µm, New Objective). A linear gradient using mobile phase A (0.1% formic acid in water) and B (100% acetonitrile) was used at a flow rate of 0.3 µl/min, starting with 1% mobile phase B and increasing to 40% B at 65 min for protein interaction identification, or increasing to 40% B at 130 min for iTRAQ experiments, then increasing to 90% within 2 min and holding for 10 min to clean the column. All mass spectrometry data were acquired in a positive ion mode. For protein interaction identification, a full MS scan (m/z 350-1800) at resolution of 120,000 was conducted, twenty MS2 scans (m/z 350-1800) were selected from twenty most intense peptide peaks of full MS scans. CID cleavage mode was performed at normalized collision energy of 35%. For iTRAQ experiments, a full MS scan (m/z 300-1800) at resolution of 120,000 was conducted, ten MS2 scans (m/z 100-1600) were activated from five most intense peptide peaks of full MS scans. CID and HCD cleavage modes were performed alternatively of the same peptides selected from full MS scans. MS2 resolution of HCD is 15,000. Bioinformatic software MassMatrix was used to search MS data against a database composed of sequences of mouse proteins from Uniprot and their reversed sequences as a decoy database. Modifications such as oxidation of methionine, labeling of cysteine (IA modifications) were selected as variable modifications in searching. For iTRAQ labeling searching, MS tag of N terminus, Lys and/or Tyr were selected as variable modification to test labeling efficiency and fixed modification for iTRAQ quantitation analysis. Trypsin was selected as the in-silico enzyme to cleave proteins after Lys and Arg. Precursor ion searching was within 10 ppm mass accuracy and product ions within 0.8 Da for CID cleavage mode and 0.02 Da for HCD cleavage mode. 95% confidence interval was required for protein identification.

Cloning, Expression, and Purification of Recombinant PKM2

The mammalian cell expression plasmid pCMV-PKM2 was obtained from Origene. Mammalian cell expression plasmid pcDNA-SCoR was constructed by PCR-cloning. pCMV-PKM2 cysteine mutants were generated by QuikChange II Site-Directed Mutagenesis Kit (Agilent). For purification of recombinant PKM2, cDNA encoding PKM2-WT or PKM2-C423A/424A were cloned into pET21b (Novagen) to introduce a C-terminal 6×His tag on the expressed protein. The recombinant PKM2 proteins were purified from BL21-CodonPlus Competent E. coli Cells (Agilent). Overnight E. coli cultures were sub-cultured into 1 L of LB medium at 5%. At OD600 of 0.5, cultures were induced with 100 mM IPTG and grown for a further 4 hr at 28° C. Cultures were centrifuged at 4000 g for 10 min to harvest the cells. Cell pellets from 1 L cultures were lysed in 10 mL of 1×PBS buffer containing 1 mM PMSF and protease-inhibitor cocktail by sonication. After centrifugation at 14500 g for 20 min, the supernatant was collected. The lysate was diluted in 30 ml 1×PBS buffer containing 1 mM PMSF and protease-inhibitor cocktail and incubated with 1 mL of Ni-NTA agarose at 4° C. for 1 hr with rotation. The slurry was then poured into empty PD-10 columns (GE Healthcare). The beads were washed with 100 mL of 50 mM NaH2PO4, 300 mM NaCl buffer containing 20 mM imidazole. Elution was done in 2 mL of 50 mM NaH2PO4, 300 mM NaCl buffer with 250 mM imidazole. Buffer was exchanged with modified Roeder D [(20 mM HEPES (pH 7.9), 20% (v/v) glycerol, 0.1 M KCL, 0.2 mM EDTA)] through Microcon centrifugal filter device (Millipore).

Cell Culture, siRNA and Related Treatments

HEK cell transfection was described herein. siRNA-mediated protein depletion was used in HEK cells. Two custom PKM2 siRNAs that target the 3' UTR of PKM2 were obtained from Dharmacon. siRNA oligonucleotides (60 pmol/10 cm plate) were transfected into HEK cells using Lipofectamine RNAiMAX (Invitrogen) according to the manufacturer's protocol. After 24 hours, 5 µg pCMV-control, pCMV-PKM2-WT or pCMV-PKM2-C423A/424A were co-transfected with siRNA oligonucleotides (60 pmol/10 cm plate) into HEK cells using Lipofectamine 2000. After 24 hrs, cells were treated with 500 µM DETA-NO for 20 hr. Cells were then collected for assay.

Pyruvate, GHB, PEP, 6PG, ATP, ADP and Serine Measurement

The amount of pyruvate was measured using Pyruvate Assay Kit (Sigma). Kidneys harvested from $SCoR^{+/+}$, $SCoR^{-/-}$, $PKM2^{+/+}$ or $PKM2^{-/-}$ mice (sham operation or AKI) were mechanically homogenized in Pyruvate Assay Buffer (1 mg/5 µl buffer). After extracts were clarified by centrifugation (20,000 g, 4° C., 20 min, ×2), supernatant was used for assay. GHB in the serum of $SCoR^{+/+}$ and $SCoR^{-/-}$ mice was measured following the GHB enzymatic assay kit from BUHLMANN. For measuring PEP, 6PG, ATP, ADP and serine in HEK cells, 1×106 cells were lysed in corresponding buffer. The amount of PEP, 6PG, ATP, ADP and serine were respectively measured using PEP Colorimetric/Fluorometric Assay Kit (Sigma), 6 phosphogluconate Assay kit (abeam), ATP Colorimetric/Fluorometric Assay Kit (Sigma), ADP Colorimetric/Fluorometric Assay Kit (Sigma) and DL-Serine Assay kit (Fluorometric) (Biovision).

Assay of NADPH-Dependent SNO-CoA Reductase Activity in Mouse

Kidneys harvested from $SCoR^{+/+}$, $SCoR^{-/-}$ and $SCoR^{-/-}/eNOS^{-/-}$ mice were mechanically homogenized in lysis buffer [50 mM phosphate buffer, pH 7.0, 150 mM NaCl, 0.1 mM EDTA, 0.1 mM DTPA, 1 mM PMSF, and protease inhibitor mixture (Roche)].

Extracts were clarified by centrifugation (20,000 g, 4° C., 20 min, ×2), and protein concentration was determined by bicinchoninic acid assay. The NADPH-dependent SNO-CoA reductase activity was determined spectrophotometrically as described previously. Briefly, the assays were performed in 50 mM phosphate buffer (pH 7.0; containing 0.1 mM EDTA and DTPA) with 0.2 mM SNO-CoA and 0.1 mM NADPH. Reactions were initiated by the addition of lysate and allowed to proceed for 1 min. All assays were performed in triplicate.

Photolysis-Chemiluminescence

Kidneys harvested from $SCoR^{+/+}$ and $SCoR^{-/-}$ mice were mechanically homogenized in lysis buffer [50 mM phosphate buffer, pH 7.0, 150 mM NaCl, 0.1 mM EDTA, 0.1 mM DTPA, 1 mM PMSF, and protease inhibitor mixture (Roche)]. Extracts were clarified by centrifugation (20,000 g, 4° C., 20 min, ×2), and protein concentration was determined by bicinchoninic acid assay. Measurements of XNO/SNO (where XNO is predominantly metal-NO (MNO)) in lysates were done using photolysis/chemiluminescence essentially as described. Briefly, nitric oxide (NO) released from MNO/SNO by UV-photolysis is detected by chemiluminescence generated by the reaction of NO with ozone. Pre-treatment of samples with $HgCl_2$ (1 mM) ($Hg^{2+}$-coupled photolysis/chemiluminescence) removes SNO specifically and allows differentiation between SNO and other photolyzable NO species (predominantly MNO).

Histological Analysis

Kidney samples were fixed with 4% PFA over 24 h, dehydrated and embedded into paraffin blocks. Formalin-fixed, paraffin-embedded blocks were sectioned and stained with Hematoxylin and eosin stain (H&E). Paraffin-embedded renal tissues were serially sectioned. At least five consecutive longitudinal sections were stained with H&E. For immunohistochemistry staining, paraffin sections were dewaxed and rehydrated. Antigen retrieval was performed by boiling sections in 0.01 M sodium citrate buffer (pH 6.0) for 20 min, then sections were washed three times with PBS. Antibody of anti-SCoR (1:100) or anti-PKM2 was dropped onto sections and incubated at 4° C. overnight. After washing with PBS, secondary antibody of HRP-associated goat anti-rabbit was dropped and incubated at room temperature for 1 hour. Diaminobenzidine (DAB) was used for coloration. More than ten microscopic fields obtained from each animal were selected for quantitative analysis. Renal histopathologic alterations were evaluated as described previously. Changes were graded on a 0 to 2 scale.

Electron Microscopy

Mice were perfused transcardially with quarter strength Karnovsky's fixative solution at a flow rate of 10 mL/min for 10 minutes. Small pieces of the kidney tissues were immersed in triple aldehyde-DMSO. After rinsing in 0.1 M phosphate buffer (pH 7.3), they were post-fixed in ferrocyanide-reduced osmium tetroxide. Another water rinse was followed by an overnight soak in acidified uranyl acetate. After again rinsing in distilled water, the tissue blocks were dehydrated in ascending concentrations of ethanol, passed through propylene oxide, and embedded in Poly/Bed resin. Thin sections were sequentially stained with acidified uranyl acetate followed by a modification of Sato's triple lead stain. These sections were examined in a FEI Tecnai Spirit (T12) transmission electron microscope with a Gatan US4000 4 k×4 k CCD.

PKM Activity

PKM activity was measured based on generation of pyruvate, which was oxidized by pyruvate oxidase to produce color (k=570 nm). To measure PKM2 activity in vitro, 250 ng recombinant PKM2-WT and PKM2-C423A/424A proteins were pre-incubated with substrate 2 µl fructose-1,6-bisphosphate (FBP)(250 µM) in 2 ml dialysis buffer [20 mM Tris-HCL (pH 7.9), 20% (v/v) glycerol, 0.1 M KCL, 0.2 mM EDTA], followed by dialysis to remove the free FBP in 2 L dialysis buffer. After 10 ng PKM2-FBP complex was treated with 200-300 µM SNO-CoA for 10 min at room temperature, the activity of PKM2 was measured. To measure PKM2 activity in kidney, kidneys were mechanically homogenized in lysis buffer [50 mM phosphate buffer, pH 7.0, 150 mM NaCl, 0.1 mM EDTA, 0.1 mM DTPA, 1 mM PMSF, and protease inhibitor mixture (Roche)]. Extracts were clarified by centrifugation (20,000 g, 4° C., 20 min, ×2), and protein concentration was determined by bicinchoninic acid assay. 10 µl (0.1 µg/µl) lysate was used to measure PKM2 activity. Assay of PKM2 activity was followed the protocol of Pyruvate Kinase Activity Colorimetric/Fluorometric Assay Kit from Biovison In.

PKM2 Dimer and Tetramer Formation

Assay of PKM2 dimer and tetramer in vitro follows previous descriptions. In brief, after 40 ng PKM2-FBP complex was treated with 200-300 µM SNO-CoA for 10 min at room temperature, 5 µl fresh glutaraldehyde (50%) was added to a reaction mixture containing 100 mM HEPES (pH 7.5) for 5 min at 37° C. The cross-linking reaction was terminated by addition of 5 µl 1M Tris-HCL (PH 8.0). Assay of PKM2 dimer and tetramer in situ was carried out as described previously. DSS (disuccinimidyl suberate; Thermo Scientific) (final 500 µM) was added to cells for 30 min at room temperature to cross-link proteins. Cells were lysed in RIPA Buffer and protein concentration was determined by bicinchoninic acid assay. Equal amounts of protein were separated by 4-15% Criterion™ Precast Midi Protein Gel and monomer, dimer and tetramer forms of PKM2 were detected with PKM2 antibody.

GSSG/GSH and NADPH/NADP+

GSSG/GSH ratio was assayed using the GSH/GSSG-Glo™ Assay kit from Promega. Mouse kidney samples (20 mg) were mechanically homogenized in 100 µl total Glutathione Lysis Reagent for total glutathione measurement or 100 µl Oxidized Glutathione Lysis Reagent for GSSG measurement. Extracts were clarified by centrifugation (20,000 g, 4° C., 20 min, ×2) and 50 µl supernatant was transferred to the plate reader. 50 µl Luciferin Generation Reagent was added to all wells, and assays were mixed and incubated for 30 minutes. 100 µl Luciferin Detection Reagent was added to wells followed by mixing. After 15 minutes of incubation, luminescence was measured using a luminometer. NADPH/NADP+ assay was done with NADP/NADPH-Glo™ Assay kit from Promega. Mouse kidney samples (20 mg) were mechanically homogenized in 100 µl of base solution [50 µl 1×PBS, 0.2 M NaOH, 1% DTAB (dodecyltrimethylammonium bromide)] for NADPH measurement or acid solution (50 µl 1×PBS, 0.2N HCl, 1% DTAB) for NADP+ measurement. Extracts were clarified by centrifugation (20,000 g, 4° C., 10 min) and 50 µl supernatant was transferred to the plate reader. After incubating samples for 15 minutes at 60° C., 50

μl of 0.25 M Trizma® base (Sigma) was added to acid-treated cells to neutralize the acid or 50 μl of HCl/Trizma® solution (0.4 M HCl and 0.5 M Trizma® base) was added to base-treated samples. 100 μl NADP/NADPH-Glo™ Detection Reagent was added to each well. After incubating for 30-60 minutes at room temperature, luminescence was measured using a luminometer.

Lipid Peroxidation

Mouse kidney samples (25 mg) were mechanically homogenized in 250 μl of RIPA Buffer (Invitrogen) containing protease inhibitors and 4 μl 2% (w/v) of the lipid antioxidant BHA. After centrifuging the extract at 160 g for 10 minutes at 4° C., the supernatant was used for analysis. For cells, $2 \times 10^7$ cells in 1 ml PBS were sonicated on ice for 10 second and the whole homogenate was used in assays. 100 μl of homogenate or 100 μl standard (malondialdehyde) was combined with 10 μl of TCA-TBA-HCl reagent [0.5% (w/v) TBA in 20% (w/v) TCA and 0.33 N HCl] and mixed thoroughly. 1.5 μl 2% (w/v) of the lipid antioxidant BHA was added to prevent lipid peroxidation during the assay. The solution was heated for 15 min in a boiling water bath. After cooling, the flocculent precipitate was removed by centrifugation at 1000 g for 10 min. 150 μl sample or standard (in duplicate) was loaded to the plate reader. The absorbance of the supernatant was measured at 532 nm against a blank that contained reagents minus homogenate. Levels of TB ARS [malondialdehyde (MDA) equivalent] were determined with a MDA standard curve.

Metabolomics

Metabolic assays were carried out as described previously. For metabolomic measurements, snap frozen kidneys were cut to equal weights (20 mg per specimen) and mechanically homogenized into four volumes of ice-cold water. In brief, sugars, sugar phosphates, organic acids, bile acids, nucleotides and other anionic polar metabolites were measured in 30 μL of tissue homogenate using hydrophilic interaction liquid chromatography and multiple reaction monitoring in the negative ion mode on a 5500 QTRAP MS (SCIEX). Amino acids, amines, acylcarnitines, nucleotides, and other cationic polar metabolites were measured in 10 μl of tissue homogenate using hydrophilic interaction liquid chromatography coupled with nontargeted, positive ion mode MS analysis on an Exactive Plus Orbitrap MS (Thermo Scientific).

Statistics

Statistics were analyzed using Minitab express. Any outliers in data were identified and excluded by Boxplot function in Minitab express. Comparisons between continuous characteristics of subject groups were analyzed with two-tailed Student's t-test. For comparisons among more than two groups, one-way ANOVA with Tukey post hoc was used. Survival was analyzed by Kaplan-Meier estimation using the SAS program. Overlapping of S-nitrosylated proteins among three independent SNO-RAC-coupled quantitative iTRAQ MS and interactions between the nitrosoproteome and SCoR interactome were analyzed using the SAS program. Sample size determination was guided by power calculations and prior experience. Mice were randomized to experimental intervention versus control. Results are presented as mean±SD. * Represents $P<0.05$, $P<0.01$, *$P<0.001$, and ****$P<0.0001$.

Results

Figure 5A:
FIGS. 5(a-g) illustrate immunoblots and images showing enzymatic mechanism by which the SNO-CoA/SCoR system regulates protein Snitrosylation. (a) Equilibrium between SNO-CoA and S-nitrosylated proteins. (b) SCoR mediates protein denitrosylation. (c) Ratio of SCoR to total protein in bovine kidney. (d-e) Expression of iNOS, nNOS, eNOS and phosphorylation of eNOS at S1177 in sham vs. injured kidneys of WT mice. (f) Expression of eNOS is normalized with GAPDH in (d) (n=9 per group). (g) Phosphorylation of eNOS at S1177 is normalized with total eNOS as in (e) (n=9 per group). Results in Two-tailed Student's t-test was used to detect significance. **P<0.01.
Figure 5B:
Figure 5C:
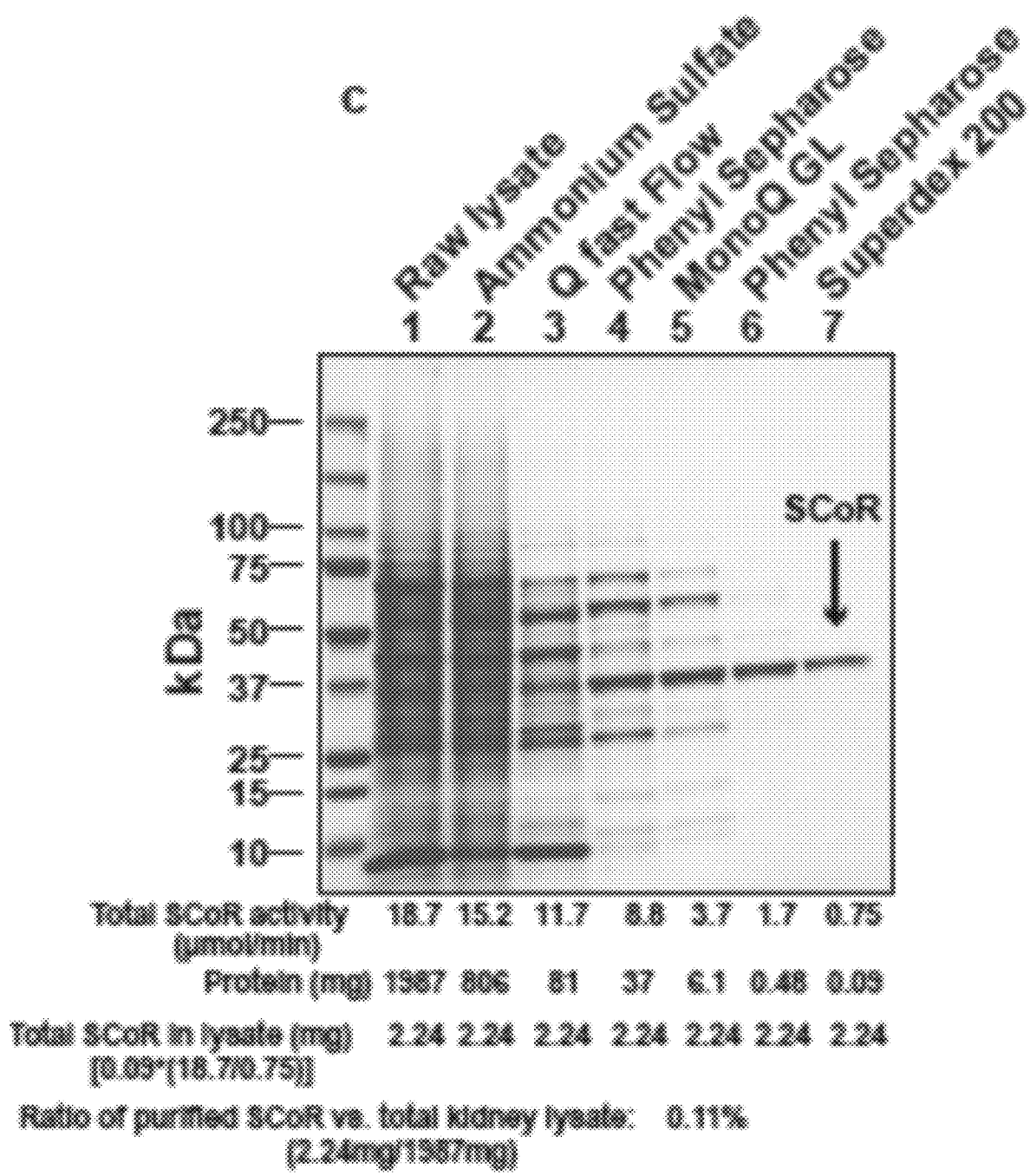
Figure 5D:
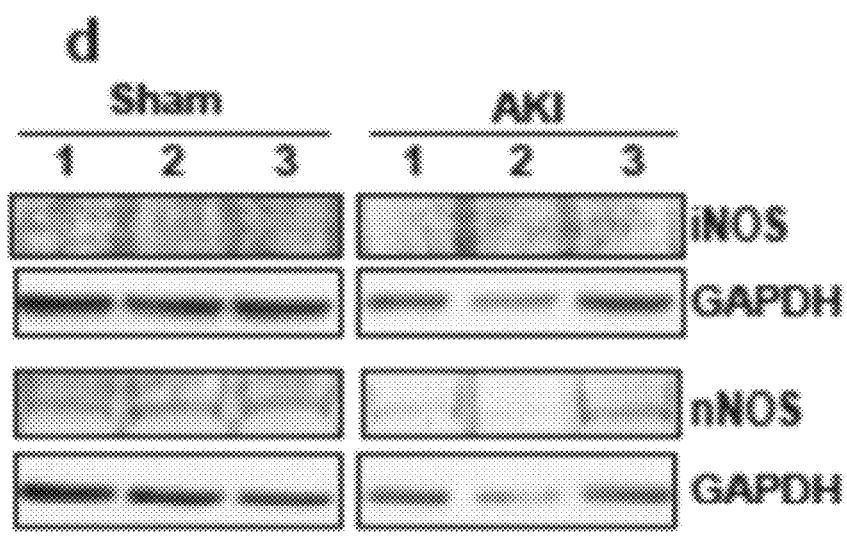
Figure 5E:
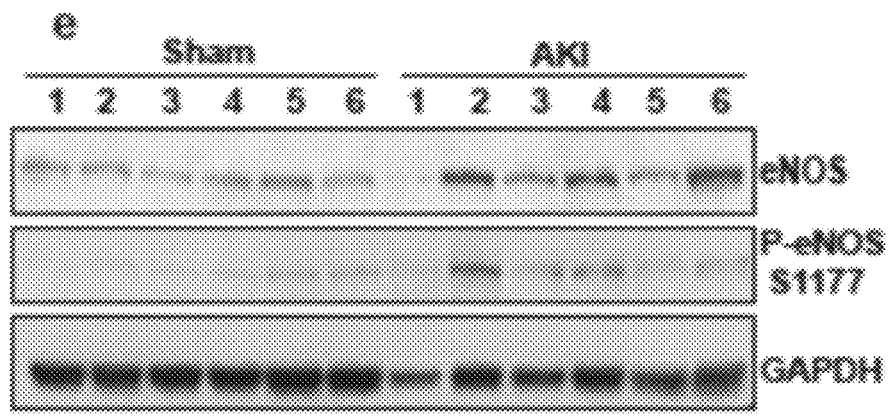
Figure 5F:
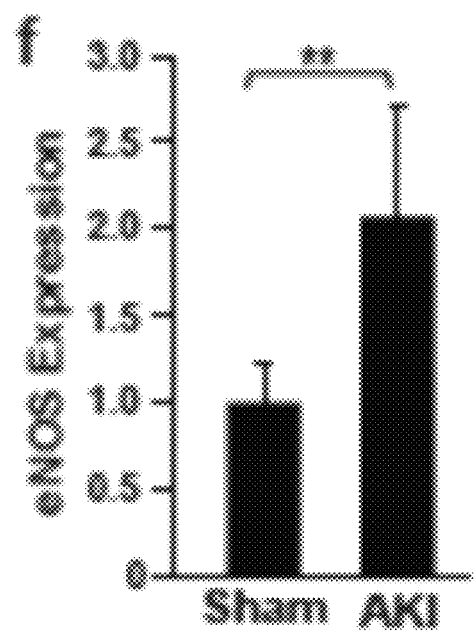
Figure 5G:
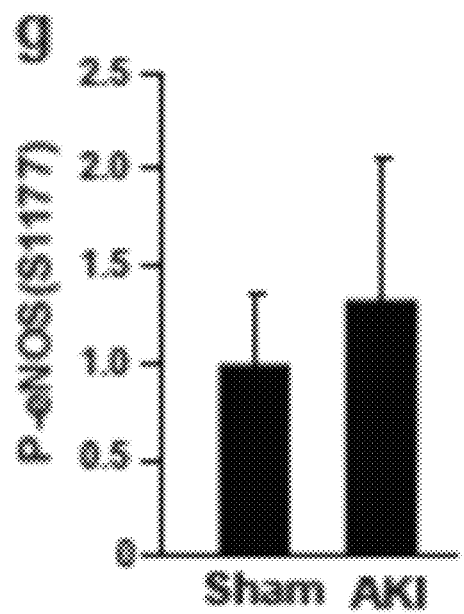

Denitrosylases of the SCoR class mediate CoA-dependent denitrosylation of proteins (FIGS. 1a and b), but their role in mammals is unknown. We found that SCoR (aka AKR1A1, formally an aldoketoreductase of unknown function) is expressed in most tissues, and most abundantly in kidney proximal tubules (FIGS. 1a and b). Notably, SCoR constitutes as much as 0.1% of protein in bovine kidney (ratio of purified SCoR vs. total bovine kidney lysate) (FIG. 5c). eNOS is also expressed highly in kidney proximal tubule epithelial cells, and its expression is induced by acute kidney injury (AKI), whereas nNOS and iNOS are barely detectable (FIGS. 5d-f). Therefore, to investigate the physiological role of the SNO-CoA/SCoR system, we created SCoR-knockout mice (SCoR$^{-/-}$), as well as SCoR/eNOS double-knockout mice (SCoR$^{-/-}$/eNOS$^{-/-}$) (FIG. 1c). SNO-CoA metabolizing activity was dramatically reduced in the kidneys of both SCoR$^{-/-}$ and SCoR$^{-/-}$/eNOS$^{-/-}$ mice (FIG. 1d).

Figure 6A:
FIGS. 6(a-t) illustrate: (a-b) Expression of SCoR after acute kidney injury. Expression of SCoR is normalized with GAPDH in (b). (c) NADPH-dependent SNO-CoA metabolizing activity was measured in kidney extracts from sham or AKI WT mice (n=8 per group). Two-tailed Student's t-test was used to detect significance. **P<0.01. (d) Serum creatinine and blood urea nitrogen (BUN) in sham-treated kidneys of SCoR$^{+/+}$, SCoR$^{-/-}$, SCoR$^{-/-}$/eNOS$^{-/-}$ and eNOS$^{-/-}$ mice (n=10 per group). (e) H&E stain for sham-treated kidneys of SCoR$^{+/+}$, SCoR$^{-/-}$ and SCoR$^{-/-}$/eNOS$^{-/-}$ mice. (t) Separate pathological scores of tubular lysis, loss of brush border and sloughed debris in the tubular lumen (n=5 mice per group).
Figure 6B:
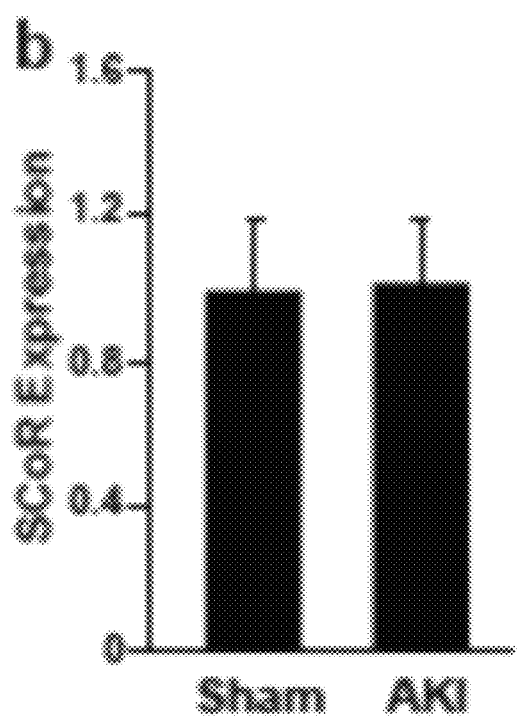
Figure 6C:
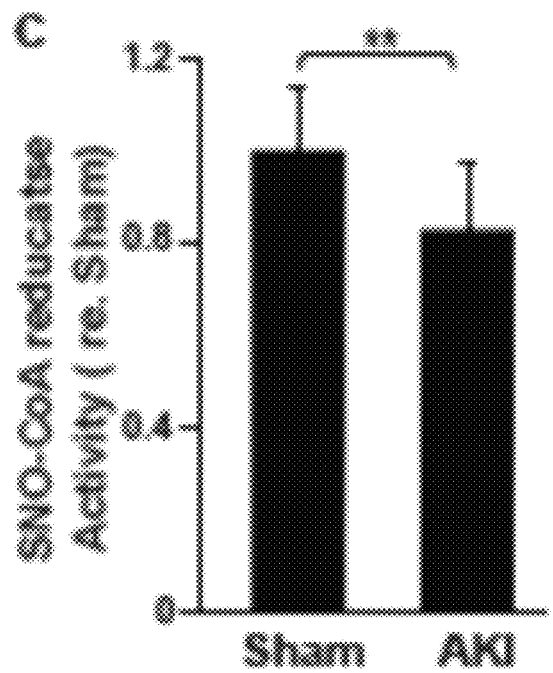
Figure 6D:
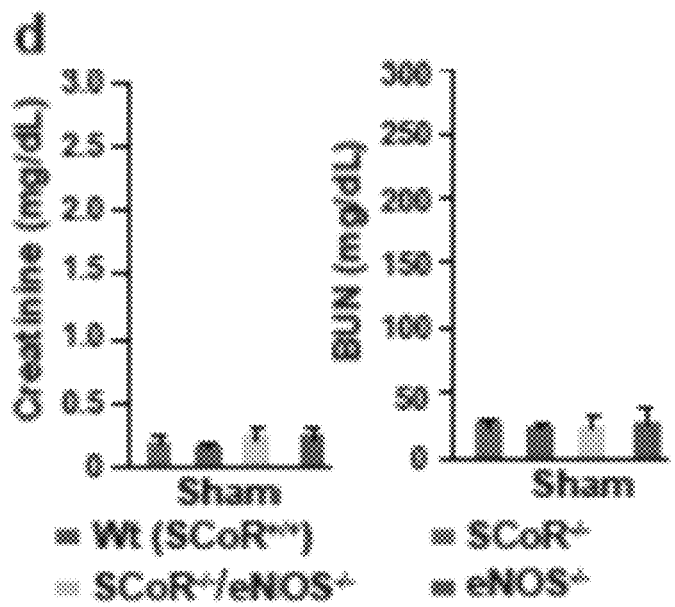
Figure 6E:
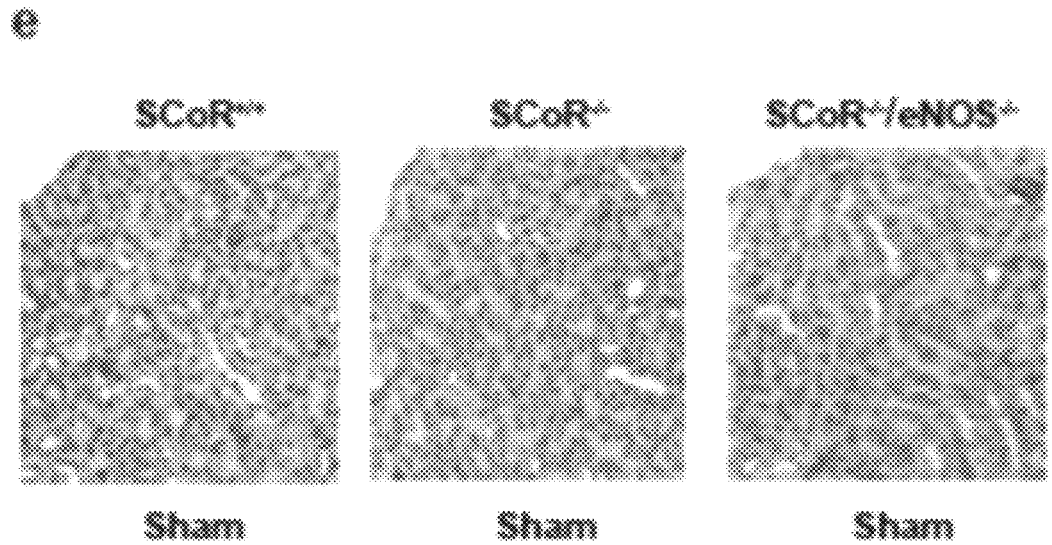
Figure 6F:
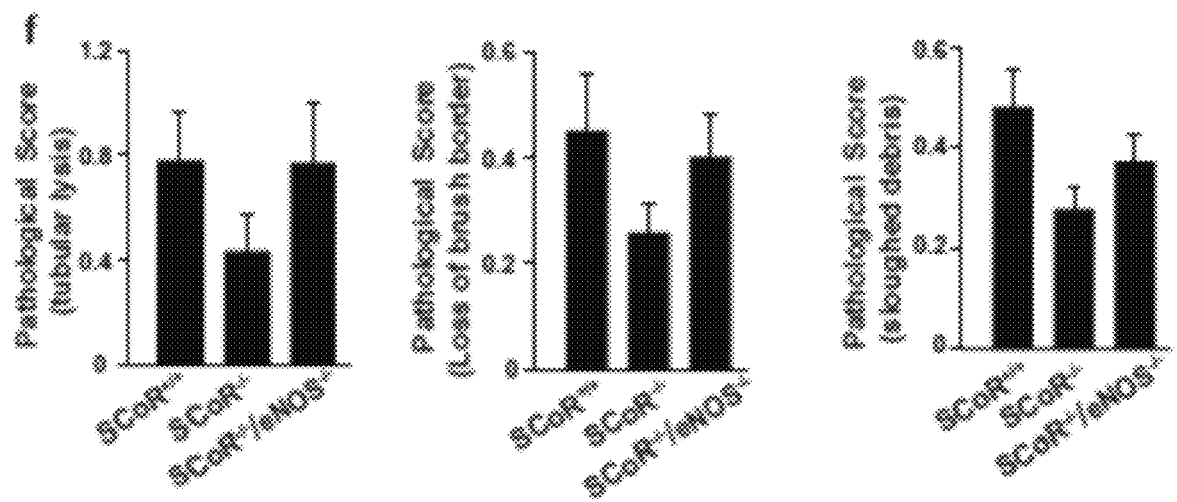
Figure 7A:
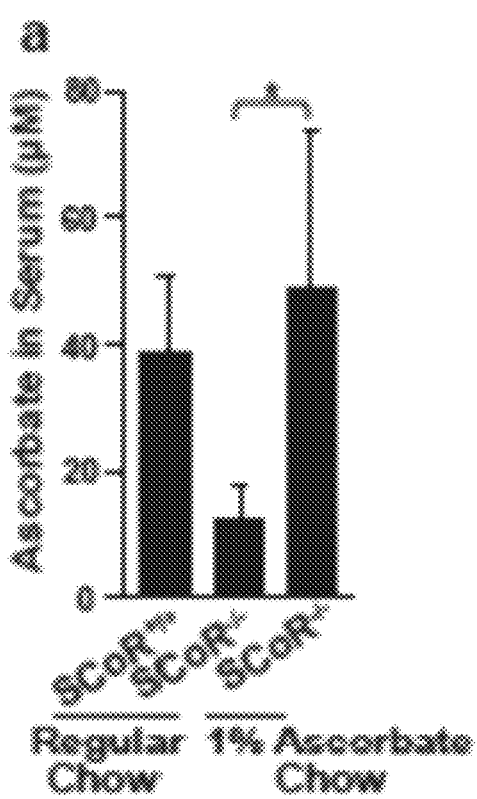
FIGS. 7(a-l) illustrate: (a) Serum ascorbate in SCoR vs. SCoR$^{-/-}$ mice fed with chow containing 1% ascorbic acid for six weeks (n=5 per group). (b-c) Serum creatinine and BUN in injured kidneys of SCoR"" vs. SCoR$^{-/-}$ mice fed with chow containing 1% ascorbic acid for six weeks (n=5 per group). (e-e) Serum creatinine and BUN in sham or injured kidneys of female SCoR$^{+/+}$ vs. female SCoR$^{-/-}$ mice (n>15 mice per group). (f-g) Serum creatinine and BUN in saline-treated or LPS-treated male SCoR$^{+/+}$ vs. SCoR$^{-/-}$ mice (n=5 per group for saline; n=11 per group for LPS). (h-l) Serum creatinine and BUN in saline-treated or LPS-treated female SCoR$^{+/+}$ vs. SCoR$^{-/-}$ mice (n=5 per group for saline; n≥12 per group for LPS). Endogenous S-nitrosylation of PKM2 in saline-treated or LPS-treated male SCoR$^{+/+}$ and SCoR$^{-/-}$ mice. Data are representative of three mice per genotype. Without ascorbate (−Ascorb) is control for SNO. Quantification of SNO-PKM2. SNO is normalized to PKM2 (input)(n=3 per group). Activity of endogenous pyruvate kinase in saline- or LPS-treated kidneys of SCoR$^{-/-}$ and SCoR$^{-/-}$ (n=5 per group). Results are presented as mean±SD. One-way ANOVA with Tukey post hoc was used to detect significance in FIGS. 7D, 7E and 7F-I. Two-tailed Student's t-test was used to detect significance in Extended Data FIGS. 3a-c, 3k and 3l. * P<0.05, P<0.01, 0.001, and **P<0.0001.
Figure 7B:
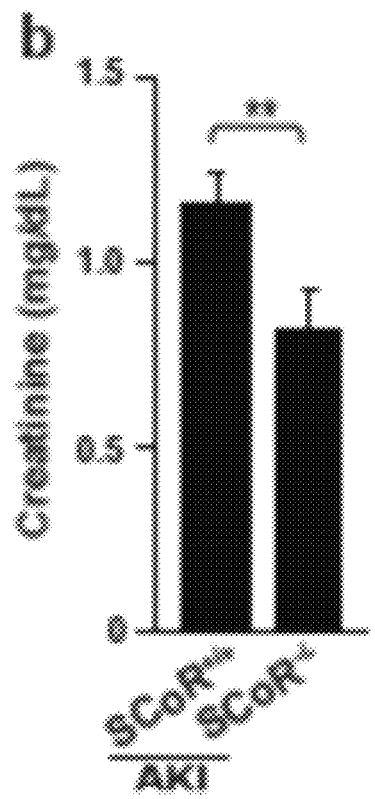
Figure 7C:
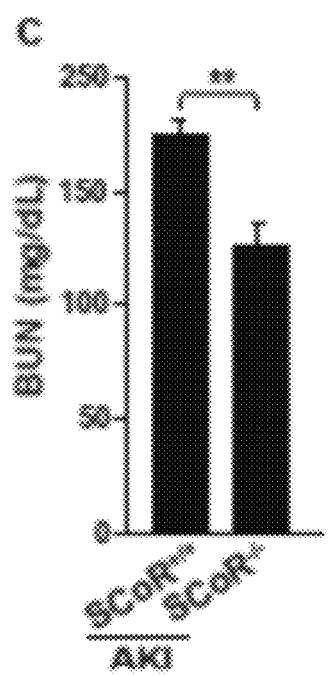

We subjected WT and SCoR$^{-/-}$ strains to ischemia-reperfusion (I/R) induced AKI (see Methods). Interestingly, SNO-CoA metabolizing activity was inhibited after AKI in WT animals (FIGS. 6a-c). Serum creatinine and blood urea nitrogen (BUN), indicators of kidney dysfunction, were significantly lower in SCoR$^{-/-}$ mice than in WT mice (SCoR$^{+/+}$) (FIGS. 1e & f). Renoprotection in SCoR$^{-/-}$ mice was lost in SCoR$^{-/-}$/eNOS$^{-/-}$ mice, indicating that protection by SCoR inhibition is dependent on NO. Conversely, eNOS$^{-/-}$ mice were more susceptible to injury than WT, and deletion of SCoR (SCoR$^{-/-}$/eNOS$^{-/-}$) counteracted their vulnerability (FIGS. 1e & f) (FIG. 6d), indicating that protection by eNOS is identified with SNO-CoA. Tubular injury was attenuated in SCoR$^{-/-}$ mice compared with either SCoR$^{+/+}$ or SCoR$^{-/-}$/eNOS$^{-/-}$ mice (FIGS. 1g & h) (FIGS. 6e & f). Since SCoR$^{-/-}$ mice have an ascorbate deficiency, chow diet was supplemented with 1% ascorbate, which normalized ascorbate levels, but had no effect on the AKI phenotype (FIGS. 7a-c). Collectively, our data support the novel perspective that protection against AKI by eNOS-derived NO is identified with SNO-CoA bioactivity and governed by SCoR.

Figure 7D:
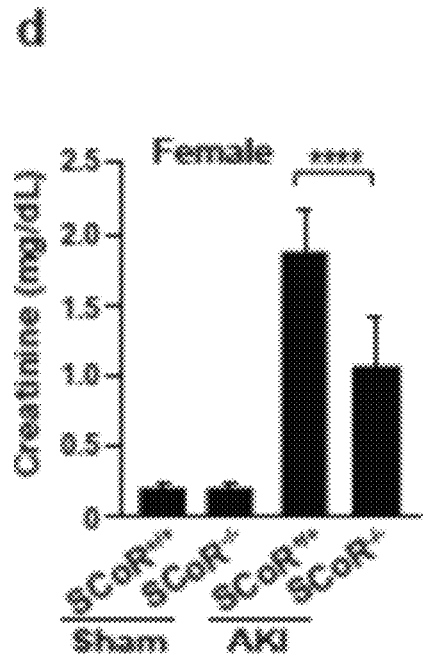

We next assessed survival following I/R-induced AKI, examined effects of gender and explored a second model of AKI. Knockout of SCoR improved survival by Kaplan-Meier estimation (FIG. 1i). Further, female SCoR$^{-/-}$ mice exhibited the same protective phenotype as males (FIGS. 7d & e), and both male and female SCoR$^{-/-}$ mice were protected against lipopolysaccharide (LPS)-induced AKI (FIGS. 3f-i). We also found that endogenous SNOs (SNO-proteins) were significantly higher in injured kidneys of SCoR$^{-/-}$ vs. SCoR$^{+/+}$ mice (FIG. 1j), whereas iron nitrosyl levels (a measure of NO production) were unchanged. These data suggest that protein S-nitrosylation by SNO-CoA protects against AKI.

Figure 2A:
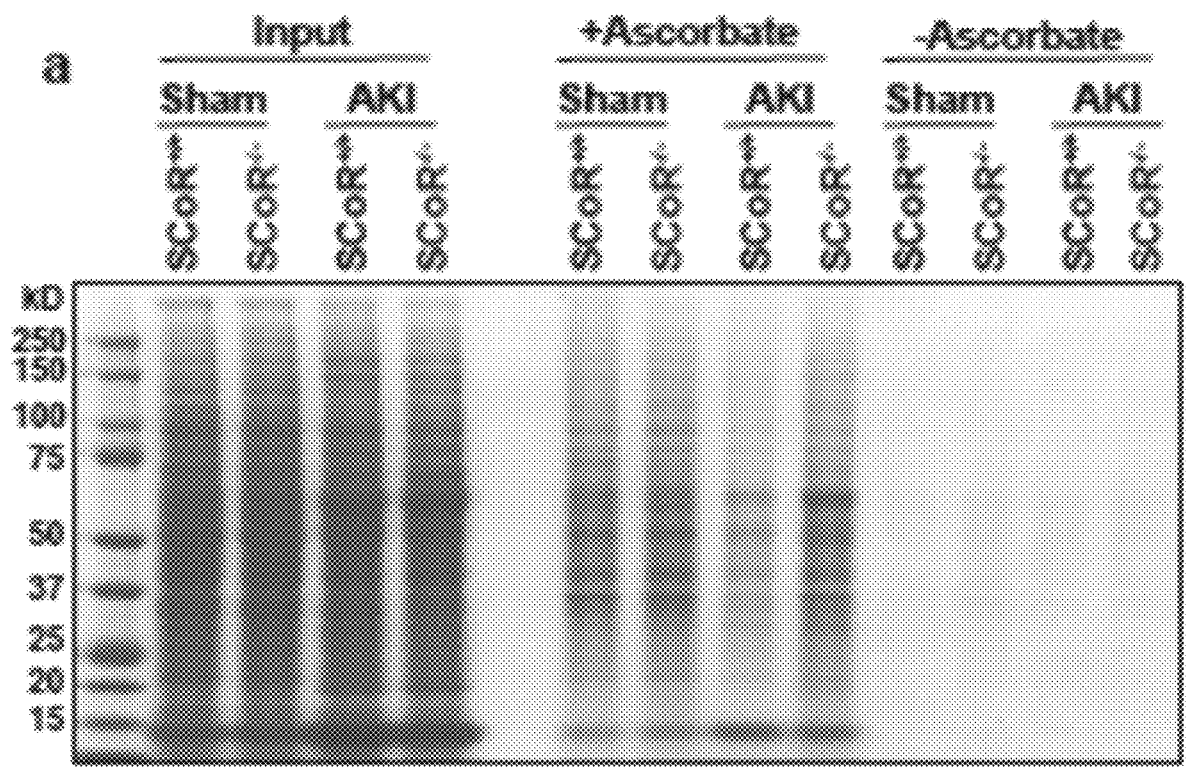
FIGS. 2(a-k) illustrate plots, schematics, and images showing S-nitrosylation of PKM2 is a major locus of regulation by the SNO-CoA/SCoR system. (a) S-nitrosylated proteins (+Ascorbate) in the kidneys of SCoR$^{+/+}$ and SCoR$^{+/+}$ mice subjected to either sham operation or I/R (–Ascorbate=negative control). (b) S-nitrosylated proteins enriched more than 1.4 fold in injured kidneys from SCoR$^{-/-}$ versus SCoR$^{+/+}$ mice (three independent experiments; SNO-RAC). (c) Proteins found in both the nitrosoproteome and SCoR interactome. (d) Shared targets identified in c. (e-j) Glycolytic intermediates glucose 6-P (G6P), fructose 6-P (F6P), dihydroxyacetone phosphate (DHAP), glyceraldehyde 3-P (G3P), 2-phosphoglycerate (2PG), phosphoenolpyruvate (PEP), pyruvate and lactate in sham-treated or I/R-injured kidneys of SCoR$^{+/+}$ vs. SCoR$^{-/-}$ mice (n=11 per group). (k) Glycolytic pathway. Intermediates in orange are increased; intermediates in blue are unchanged; intermediates in green were not identified by metabolomics. Results are presented as mean±SD. One-way ANOVA with Tukey post hoc was used to detect significance in FIG. 1e-j. *P<0.001, and **P<0.0001.
Figure 2B:
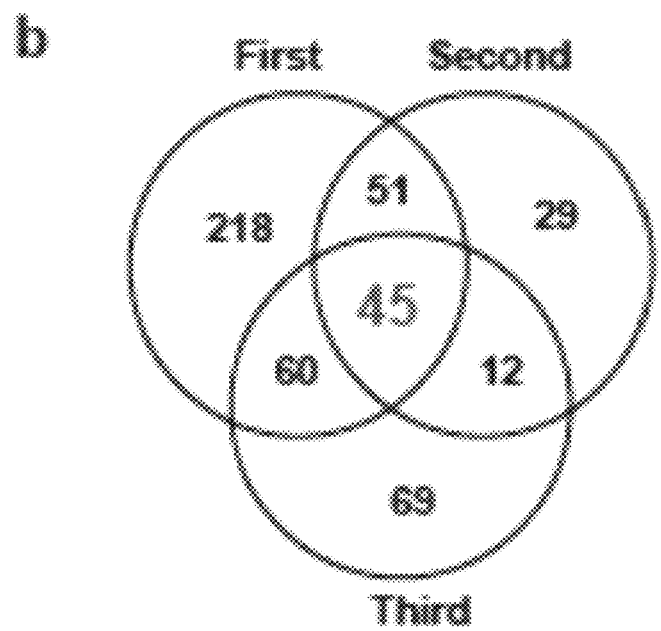
Figure 2E:
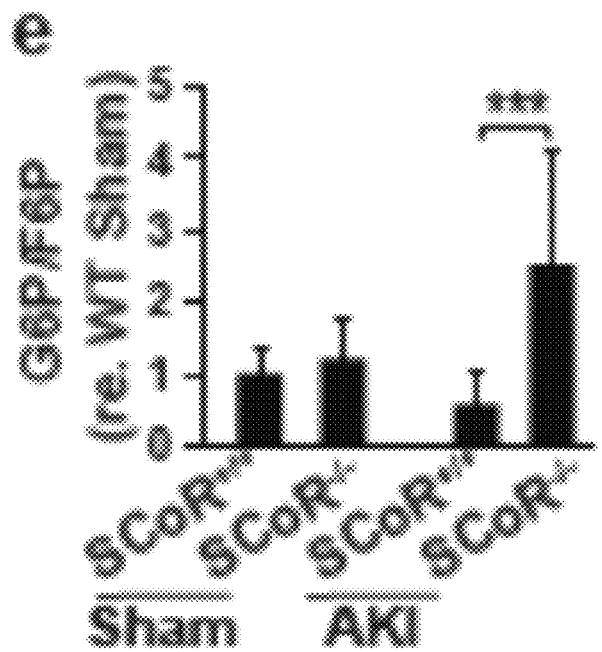
Figure 2F:
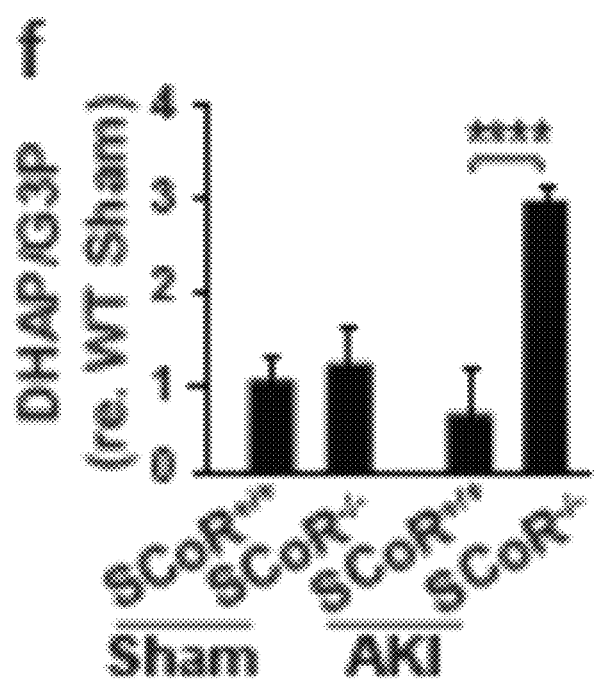
Figure 2G:
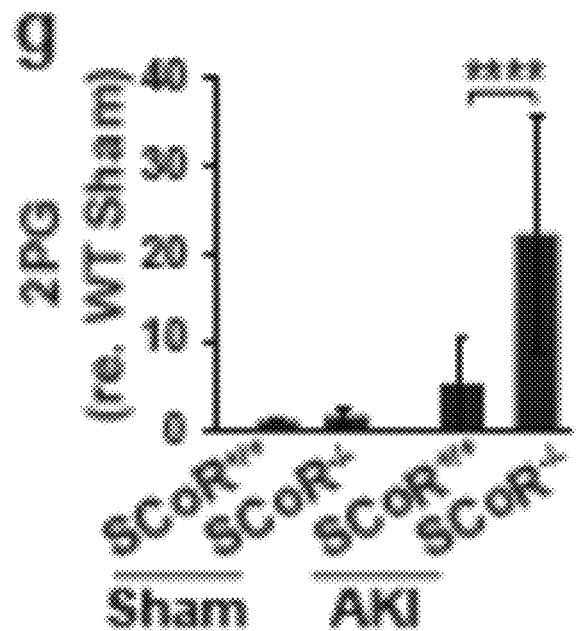
Figure 2H:
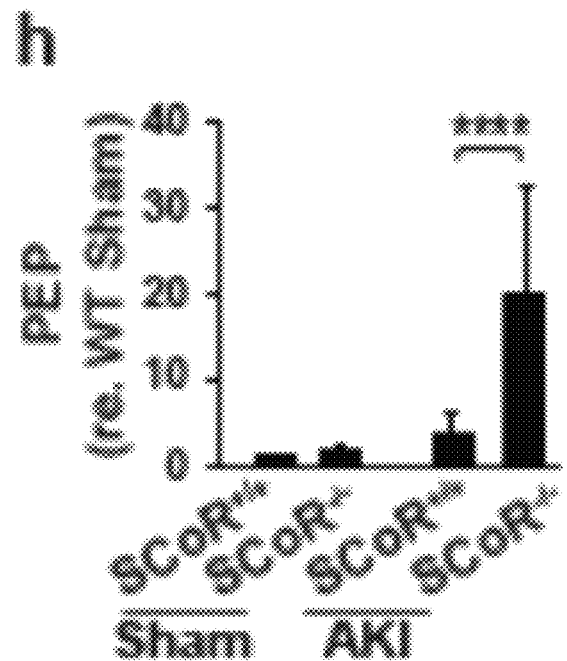
Figure 2I:
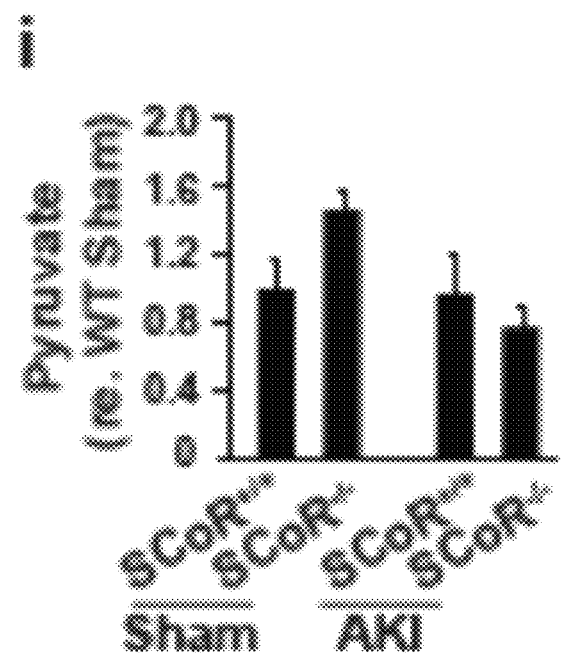
Figure 2J:
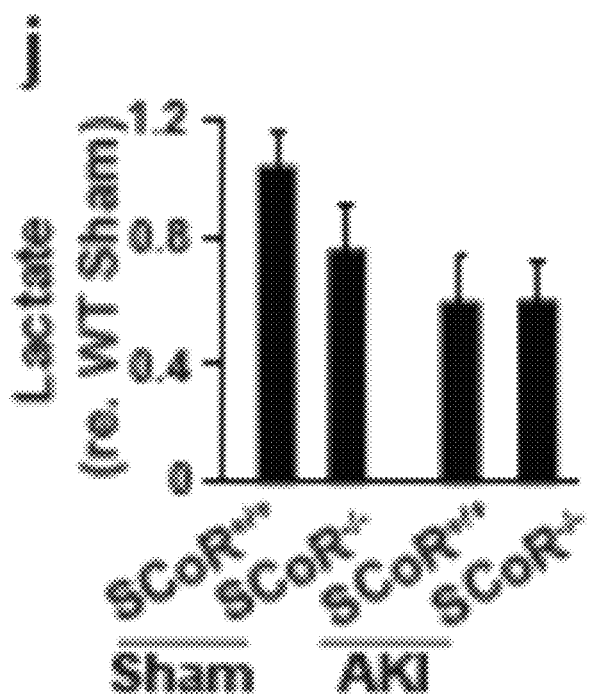

Protein S-nitrosylation typically operates within multi-protein macro-complexes, where SCoR may interact directly with SNO targets. Because CoA is central to metabolism and most targets of SCoR in yeast are metabolic enzymes, we assumed the same might hold true in mammals. Alterations in metabolism after AKI may play a protective role. Therefore, to identify the protein targets of S-nitrosylation that mediate protection by the SNO-CoA/SCoR system, we combined three unbiased proteomic and metabolomic screening approaches. First, resin-assisted capture of SNO-proteins (SNO-RAC) was coupled with quantitative iTRAQ mass spectrometry (MS) for SNO-protein identification. SNO-protein levels from injured SCoR$^{-/-}$ kidneys were elevated versus SCoR$^{+/+}$ (FIG. 2a) and 45 SNO-proteins were detected as enriched ≥1.4 fold in three independent experiments (FIG. 2b). Second, we isolated the SCoR interactome from mouse kidney extracts by immunoprecipitation, identifying 37 proteins. Notably, seven of these proteins overlapped with the nitrosoproteome (SNO-ome) identified by SNO-RAC, including the prominent metabolic enzyme pyruvate kinase M2 (PKM2) (FIGS. 2c, d). Third, we performed metabolic profiling following AKI (vs. sham) in $SCoR^{-/-}$ vs. $SCoR^{+/+}$ mice. Multiple glycolytic intermediates, including glucose-6-P, fructose-6-P, DHAP, glyceraldehyde-3-P, 2-phosphoglycerate and phosphoenolpyruvate (PEP), accumulated in injured kidneys of $SCoR^{-/-}$ mice, whereas downstream intermediates, pyruvate and lactate, did not accumulate (FIGS. 2e-k). These data suggest a block at the last step in glycolysis-between PEP and pyruvate-which is catalyzed by PKM2 (FIG. 2k) (note: declines in pyruvate are likely prevented via multiple routes, including degradation of amino acids, conversion of lactate to pyruvate, and oxidative decarboxylation of L-malate). Thus, PKM2 is identified as: i. a SNO-CoA-regulated SNO-protein, ii., a component of the SCoR interactome and iii., a site of metabolic regulation by the SNO-CoA/SCoR system. Our results point to inhibitory S-nitrosylation of PKM2 in injured kidneys of $SCoR^{-/-}$ mice.

Figure 3A:
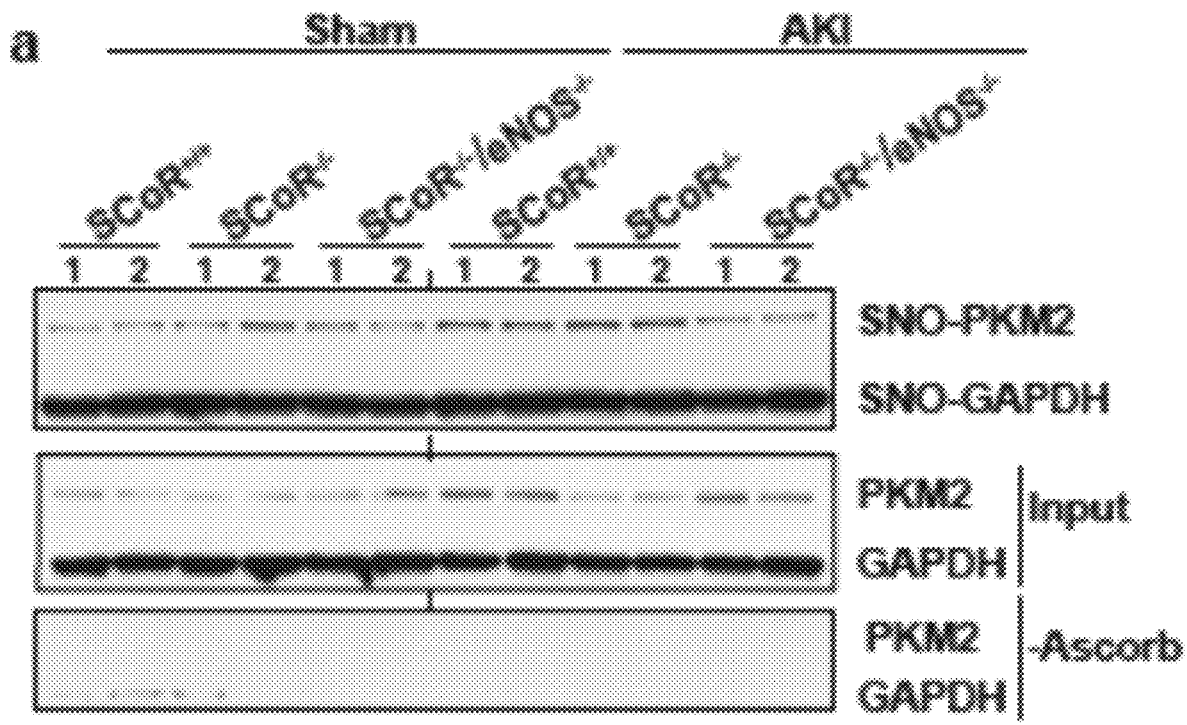
FIGS. 3(a-i) illustrate immunoblots and tables showing S-nitrosylation of renal PKM2 inhibits its activity by blocking tetramer formation. (a) Endogenous S-nitrosylation of PKM2 in sham or injured kidneys of SCoR$^{+/+}$, SCoR$^{-/-}$ and SCoR$^{-/-}$/eNOS$^{-/-}$ mice. Data are representative of two mice per genotype. Without ascorbate (–Ascorb) is control for SNO. SNO-GADPH and GAPDH (input) are used as internal controls. Injury induced by I/R. (b) Quantification of SNO-PKM2. SNO is normalized to PKM2 (input) (n=6 per group). Activity of endogenous pyruvate kinase (PK) in sham or injured kidneys of SCoR$^{+/+}$, SCoR$^{-/-}$ and SCoR$^{-/-}$/eNOS$^{-/-}$ mice (n=6 per group). (c) Activity of recombinant PKM2 proteins after SNO-CoA treatment (n=3). FBP=Fructose 1,6 biphosphate (PKM2 activator). (e) SNO in PKM2 cysteine mutants in HEK cells (n=5). (f) Activity of recombinant PKM2-WT and PKM2-C423/424A after SNO-CoA treatment (n=3). (g) Dimer and tetramer distribution of recombinant PKM2-WT and PKM2-C423/424A after SNO-CoA treatment in vitro (n=3). (h) Glycolytic intermediate accumulation (PEP) in Myc-PKM2-WT and Myc-PKM2-C423/424A expressing HEK cells after 500 μM DETANO(NO) treatment (n=4). Results are presented as mean±SD. One-way ANOVA with Tukey post hoc was used to detect significance in FIGS. 3b-e and 3g. Two-tailed Student's t-test was used to detect in FIGS. 3f and 3h P<0.01, *P<0.001.
Figure 3B:
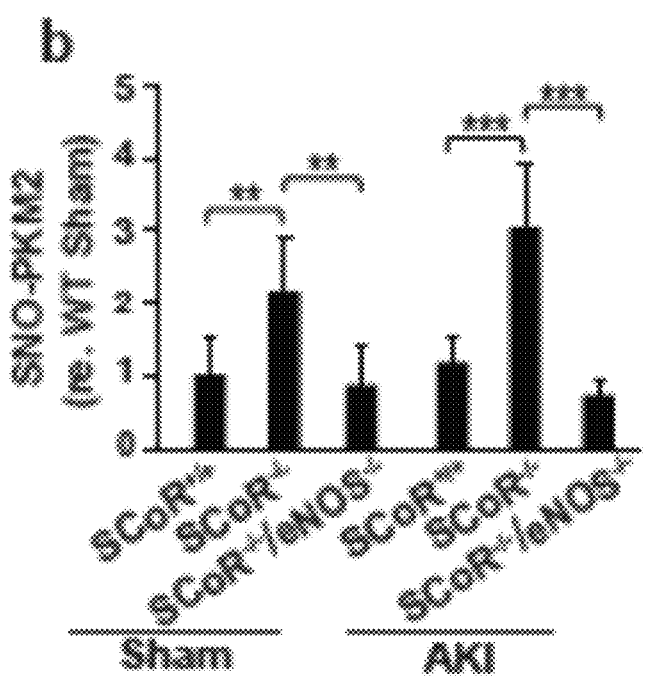
Figure 3C:
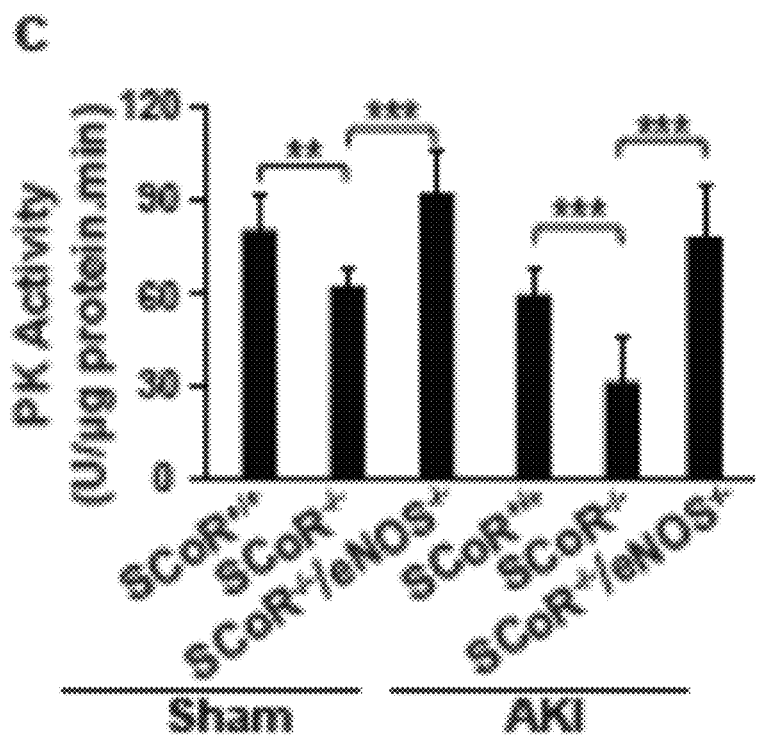
Figure 3D:
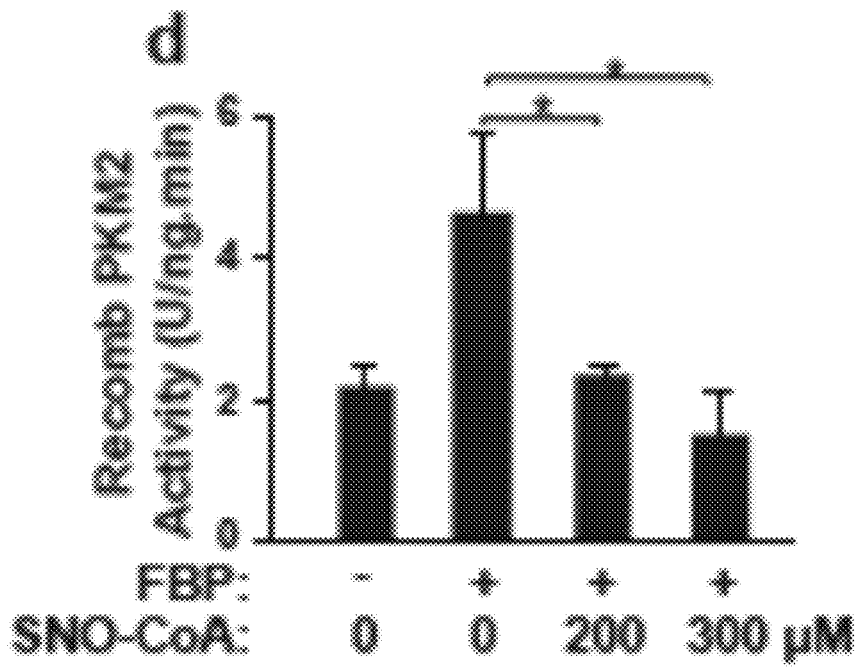
Figure 7E:
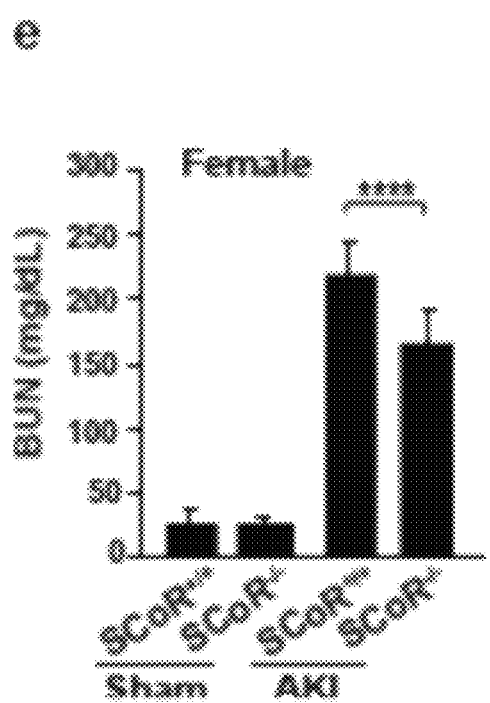
Figure 7F:
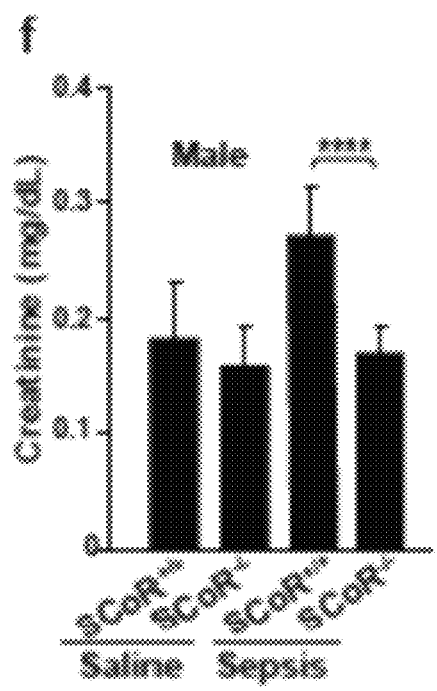
Figure 7G:
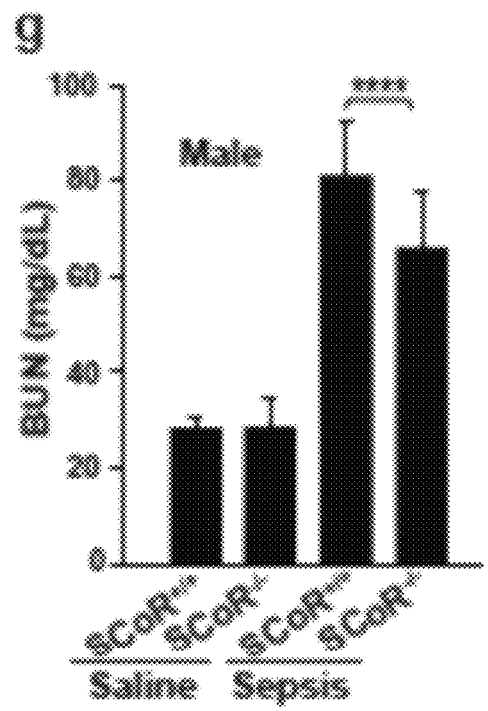
Figure 7H:
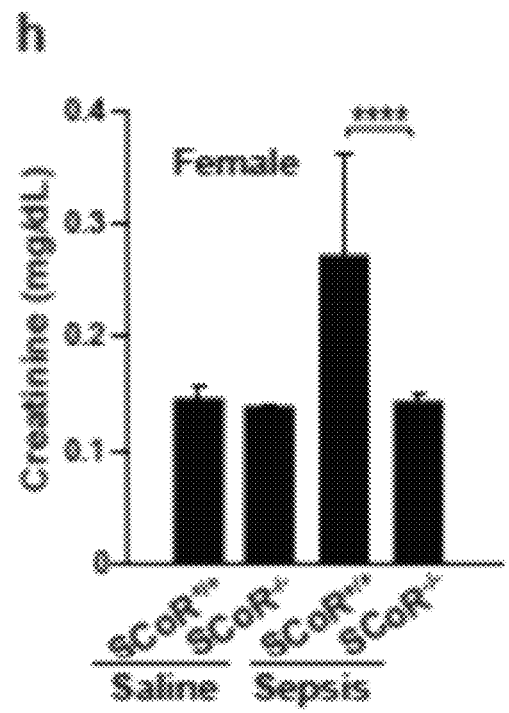
Figure 7I:
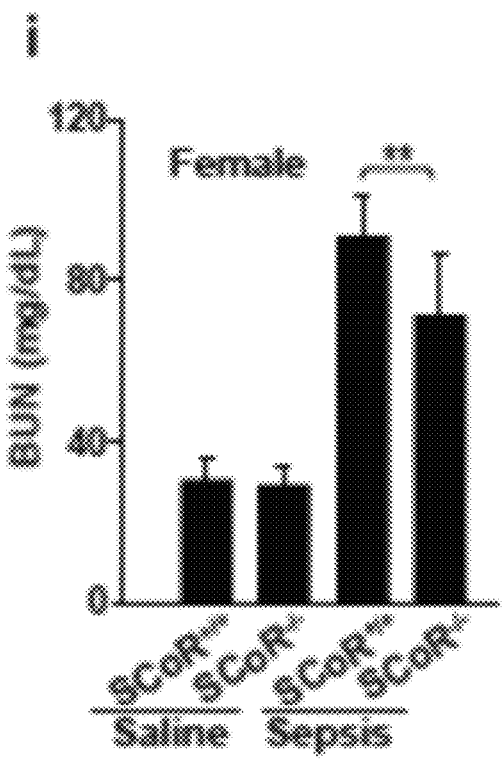
Figure 7J:
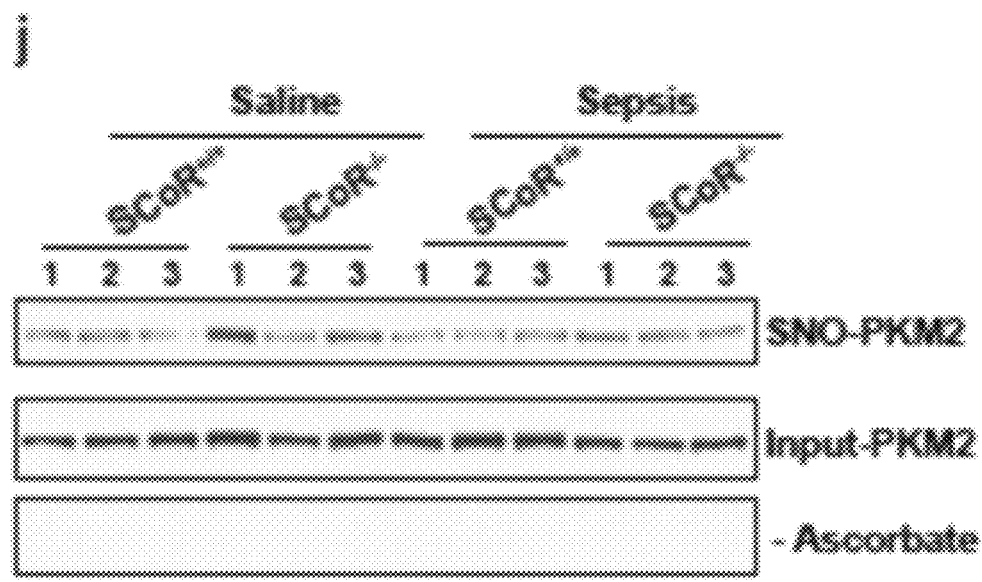
Figure 8B:
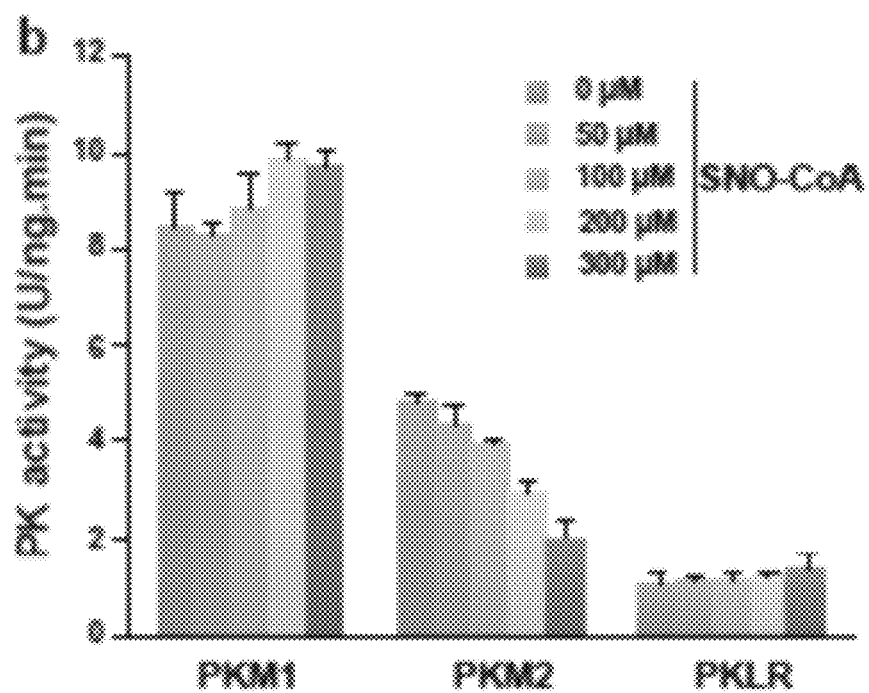
FIGS. 8(a-d) illustrate: (a) Interaction between SCoR and PKM2. Myc-PKM2 and V5-SCoR are co-overexpressed in HEK cells. IP with anti-rabbit Myc antibody; IB with V5 antibody. (b) Activity of recombinant PKM2, PKM1 and PKLR proteins after SNO-CoA treatment (n=3). (c) Expression of PKM2, PKM1 and PKLR in the kidney of SCoR$^{+/+}$ and SCoR$^{-/-}$ mice after 24-hours of AKI. (d) Quantification of expression of PKM2, PKM1 and PKLR in (c)(n=3). Result is presented as mean±SD. Two-tailed Student's t-test was used to detect significance. *P<0.05.
Figure 8C:
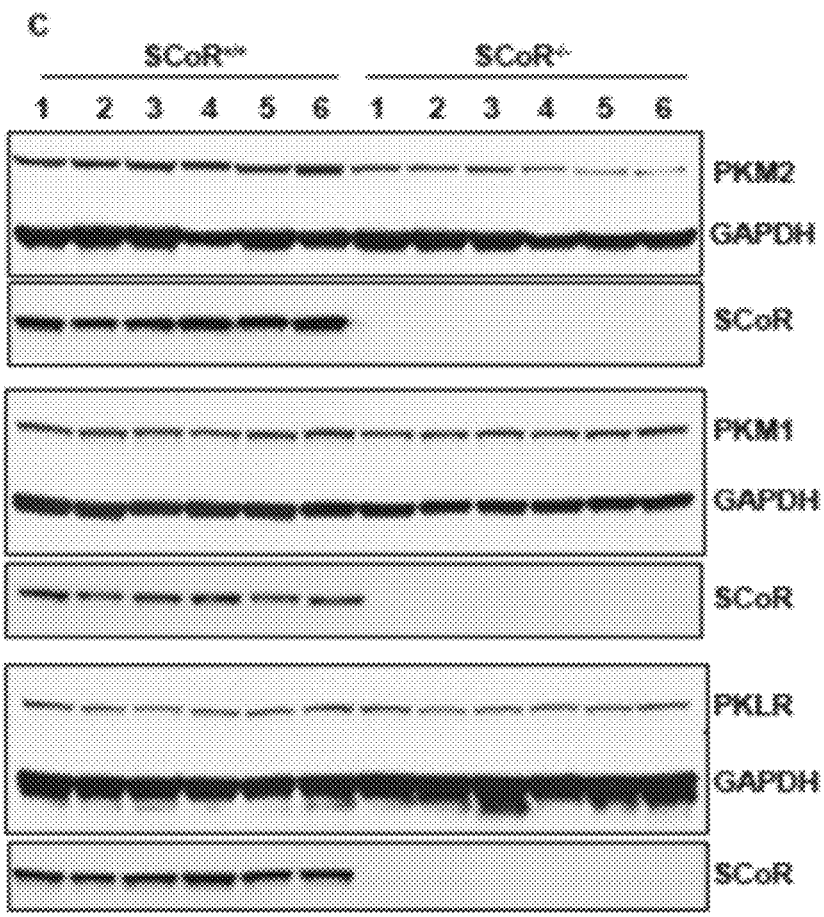
Figure 8D:
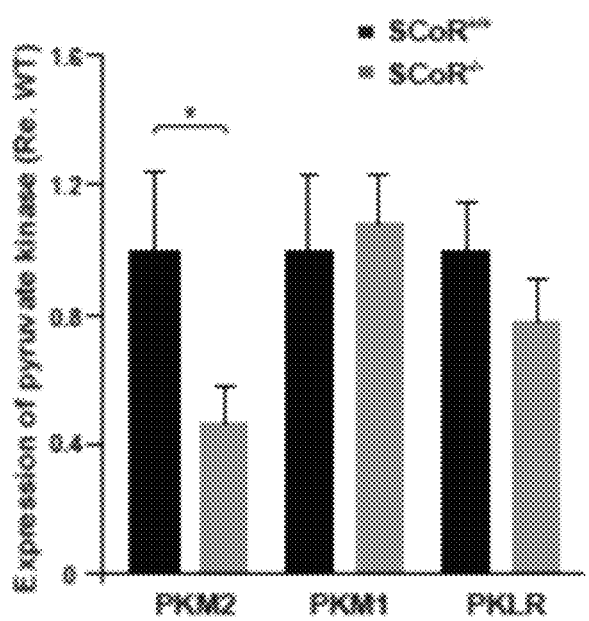

To verify the regulation of PKM2 by SCoR, we measured S-nitrosylated PKM2 (SNO-PKM2) levels and activity following PR-induced AKI. Amounts of SNO-PKM2 were higher in $SCoR^{-/-}$ vs. $SCoR^{+/+}$ kidneys and increases in SNO-PKM2 were associated with lower PKM2 activity (FIGS. 3a-c); both increases in SNO-PKM2 and decreases in PKM2 activity were eNOS-dependent (FIGS. 3a-c). Increased SNO-PKM2 and decreased PKM2 activity in $SCoR^{-/-}$ mice were also correlated with protection in sepsis-induced AKI (FIGS. 7j-l). As further validation, we showed that PKM2 interacted with SCoR in HEK cells (FIG. 8a), as it does in native kidneys, and that recombinant PKM2, but not other PK isoforms (PKM1 or PKLR), was directly inhibited by SNO-CoA (FIG. 3d) (FIG. 8d). Our data indicate that PKM2 activity following AKI is governed by SCoR-regulated S-nitrosylation.

Figure 3E:
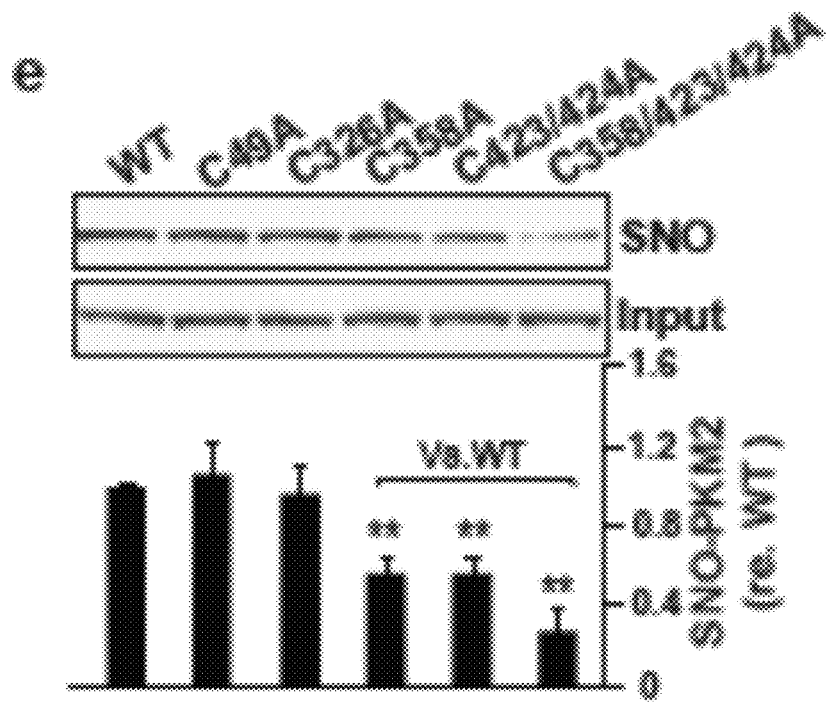
Figure 3F:
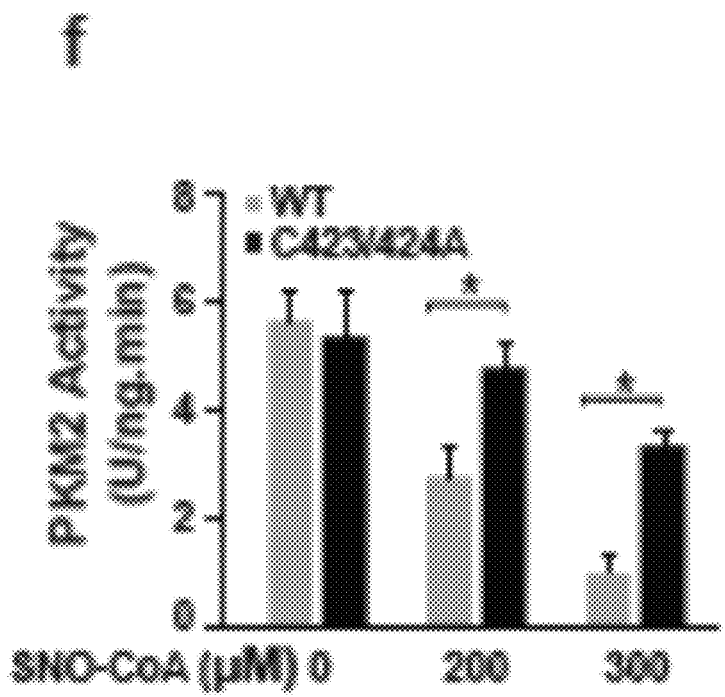
Figure 3G:
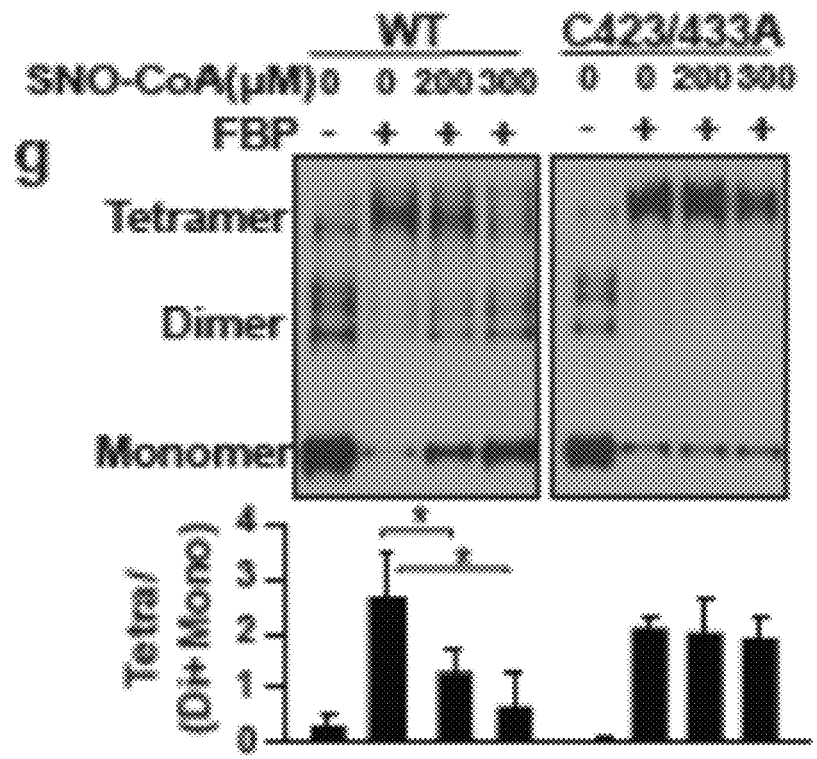
Figure 3H:
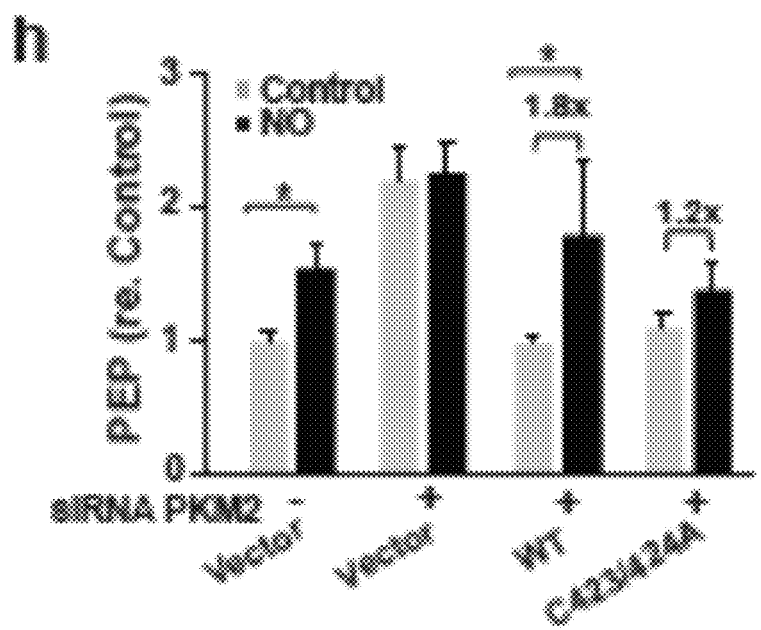
Figure 9A:
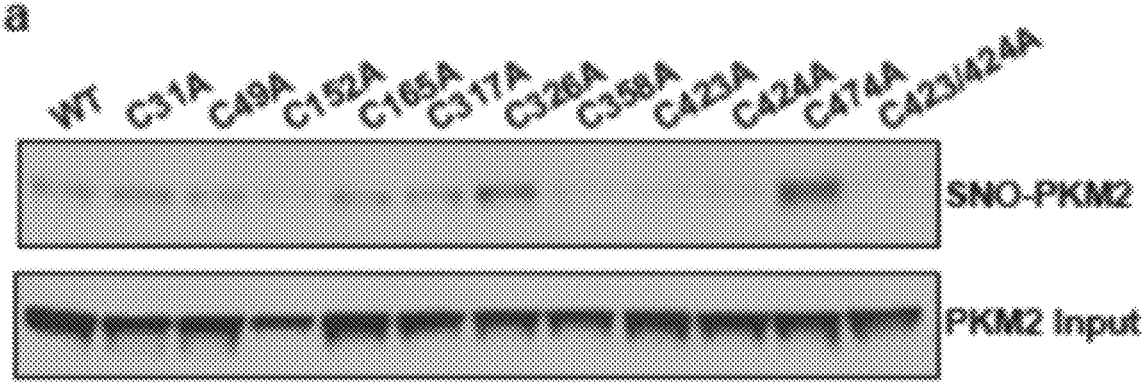
FIGS. 9(a-e) illustrate: (a) endogenous SNO-PKM2 in PKM2 Cys-mutants eNOS-overexpressing HEK cells. (b) Mutation of C152 to alanine affects the SNO level of PKM2 in eNOS-overexpressing HEK cells. (c) Quantification of expression of Myc-PKM2-wild-type (WT), Myc-PKM2-C49A and. Myc-PKM2-C152A in eNOS-overexpressing HEK cells. Normalized with expression of GAPDH (n=3). Quantification of SNO-PKM2 in eNOS-overexpressing HEK cells. SNO is normalized to PKM2 (input) (n=3). (e) mRNA level of Myc-PKM2-WT, Myc-PKM2-C49A and Myc-PKM2-C152A in eNOS-overexpressing HEK cells (n=3). Results in FIGS. 9c and d are presented as mean±SD. Two-tailed Student's t-test d to detect significance. *P<0.05.
Figure 9B:
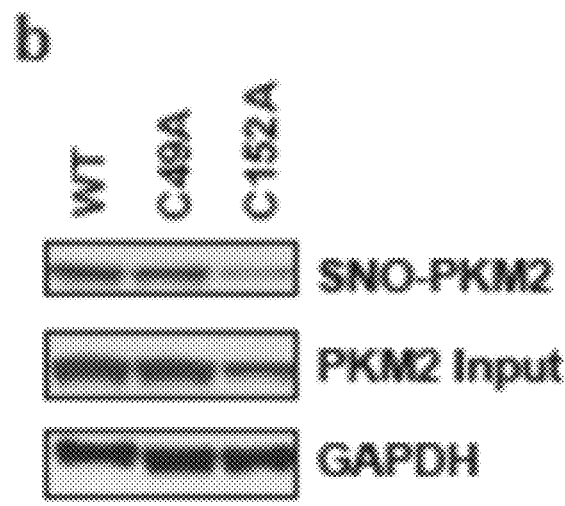
Figure 9C:
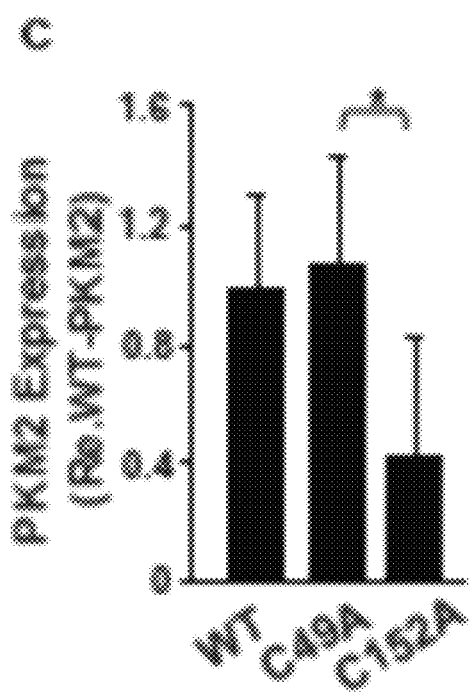
Figure 9D:
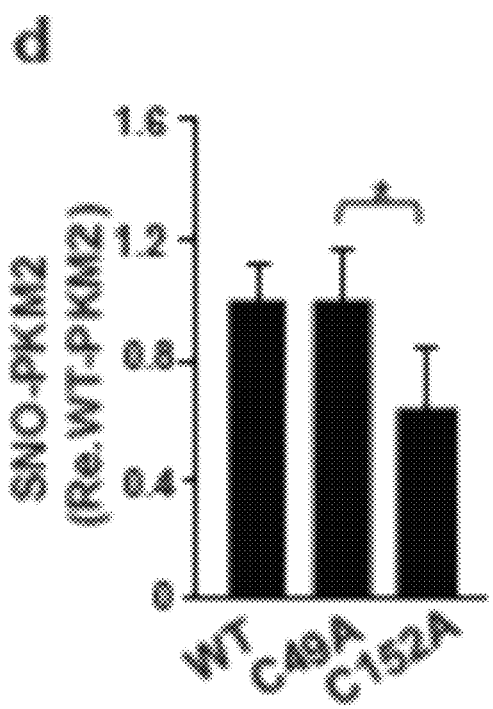
Figure 9E:
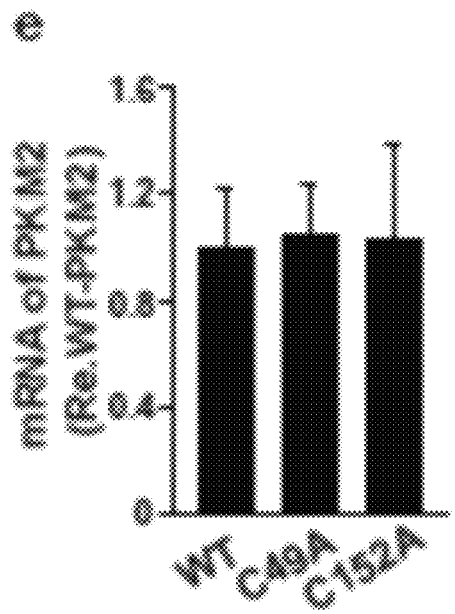
Figure 11A:
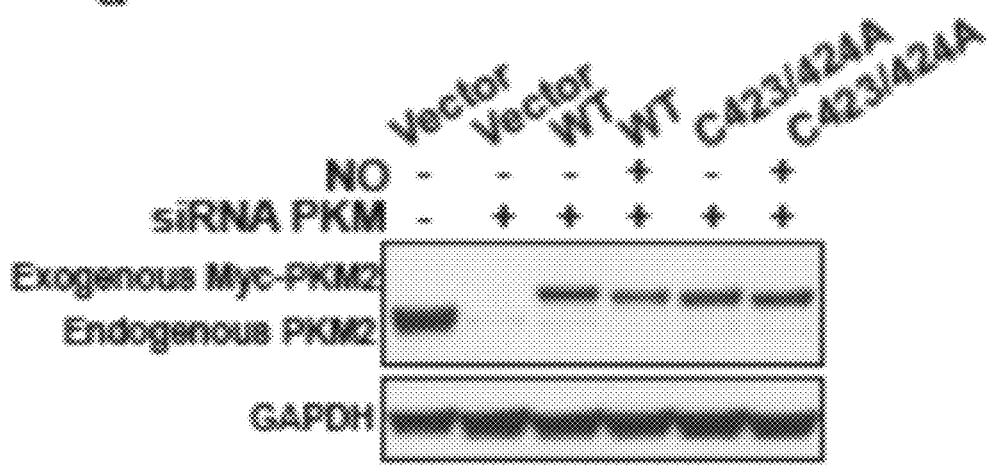
FIGS. 11(a-g) illustrate: (a) expression of endogenous and overexpressed PKM2 in HEK cells. (b) Activity of Myc-PKM2-WT and Myc-PKM2-C423/424A after NO (DETANO; 50004) treatment in HEK cells (n=3). (c) The total amount of GSH+GSSG in sham-treated or AKI kidneys of SCoR$^{+/+}$, SCoR$^{-/-}$ and SCoR$^{-/-}$/eNOS$^{-/-}$ mice (n=6 per group). (d) The amount of 6-phosphogluconate (6PG), a key PPP intermediate, in Myc-PKM2-WT and Myc-PKM2 C423/424A expressing HEK cells after NO (DETANO; 500 µM) treatment (n=4). (e) The amount of serine in injured kidneys of SCoR$^{+/+}$ vs. SCoR$^{-/-}$ mice (n=11 per group). (f) The amount of serine in Myc-PKM2-WT and Myc-PKM2-C423/424A HEK cells after NO treatment (DETANO; 504M) (n=4). (g) The amount of gamma-hydroxybutyric acid (GHB) in serum of SCoR$^{+/+}$ and SCoR$^{-/-}$ mice (n=7 per group). Results are presented as mean±SD. Two-tailed Student's t-test was used to detect significance. *P<0.05, **P<0.01.
Figure 11B:
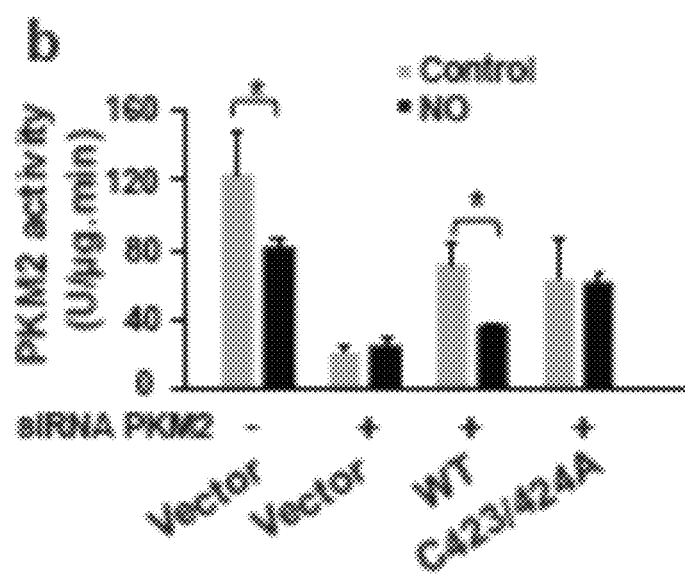
Figure 11C:
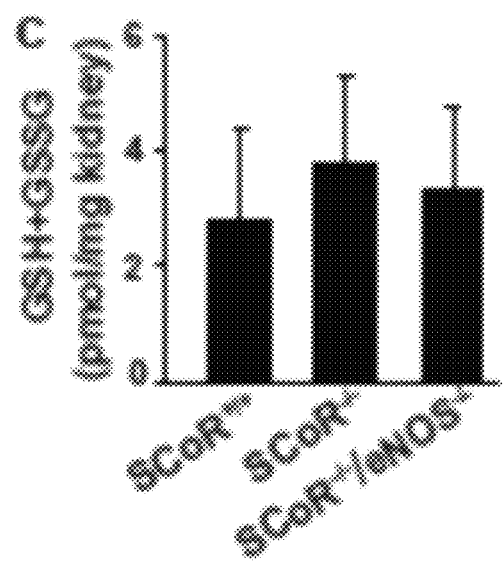

PKM2 has 10 Cys residues; each was individually mutated to alanine and mutant proteins were expressed together with eNOS in HEK cells. These analyses revealed that four cysteine residues, C152, C358, C423 and C424, are targeted by S-nitrosylation and thus account for measureable SNO in PKM2 (FIG. 9a) (FIG. 3e). PKM2 degradation was promoted by C152 mutation (FIGS. 9b-e). S-nitrosylation of PKM2 may therefore rationalize reduced PKM2 expression in $SCoR^{-/-}$ mice (FIG. 3a) (FIGS. 8c & d). It is has been previously shown that oxidation of PKM2 at C358 can inhibit PKM2 activity; however, C423/424 are newly discovered regulatory sites. Interestingly, C423 and C424 are encoded by the PKM2-specific, alternatively spliced exon 10 and are localized at the interacting surfaces of the PKM2 tetramer FIG. 6a&b). Furthermore, the activity of PKM2-C423/424A cannot be inhibited by either SNO-CoA in vitro or the NO donor DETA-NO in HEK cells, confirming that cysteines 423 and 424 are the principal targets of NO (FIG. 3f) (FIG. 11b). The activity of PKM2 is mainly determined by the amount of high-activity tetramer vs. low-activity dimer. Using purified proteins, we found that SNO-CoA inhibited formation of tetrameric PKM2-WT but not of tetrameric PKM2-C423/424A (FIG. 3g). To show that NO blocks glycolysis by this mechanism, we overexpressed Myc-PKM2-WT or Myc-PKM2-C423/424A in a HEK cells in which endogenous PKM2 has been knocked down (FIG. 11a). NO promoted the accumulation of PEP in Myc-PKM2-WT but not Myc-PKM2-C423/424A cells (FIG. 3h). Thus, S-nitrosylation of C423/424 is primarily responsible for inhibition of PKM2 by SNO-CoA.

Figure 4A:
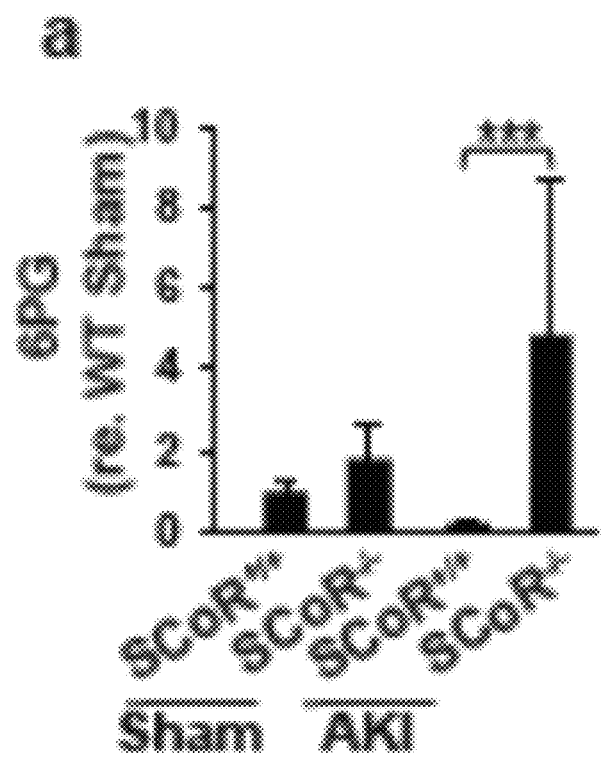
FIGS. 4(a-q) illustrate tables, immunoblots, and images showing inhibition of PKM2 increases flux through the pentose phosphate pathway (PPP) and protects from AKI. (a-c) Quantification of key PPP intermediates 6-phosphogluconate (6PG), xylulose 5-P (X5P), ribose 5-P (R5P), erythrose-4-phosphate (E4P) in sham-treated vs. injured kidneys of SCoR$^{+/+}$ and SCoR$^{-/-}$ mice (n=11 per group). Injury induced with I/R. (d) Pentose phosphate pathway. Intermediates are increased. (e) Ratio of NADPH/NADP+ in sham-treated or AKI kidneys of SCoR$^{+/+}$, SCoR$^{-/-}$ and SCoR$^{-/-}$/eNOS$^{-/-}$ mice (n=6 per group). (f-g) The ratio of GSSG/GSH and lipid peroxidation in sham-treated or AKI kidneys of SCoR$^{+/+}$, SCoR$^{-/-}$ and SCoR$^{+/+}$eNOS$^{-/-}$ mice (n=6 per group). (h) Expression of PKM2 and PKM1 in the kidneys of wild-type control (PKM2$^{+/+}$) and PKM2$^{-/-}$ mice. Quantification is based on 5 mice per group. (i) Pyruvate kinase (PK) activity in the kidney from PKM2$^{+/+}$ and PKM2$^{-/-}$ mice (n=5 per group). (j-k) Serum creatinine and BUN in PKM2$^{+/+}$ and PKM2$^{-/-}$ after I/R-induced AKI (n=7 per group). (l) H&E staining in AKI-damaged kidneys. Renal tubular injury includes tubular lysis (black arrow), loss of brush borders (green arrow) and debris in tubular lumen (red arrow). (m) Pathological scores of tubular injury of WT vs PKM2$^{-/-}$ mice (n=5 per group). (n-p) NADPH/NADP+, GSSG/GSH and lipid peroxidation in AKI-damaged kidneys of WT and PKM2$^{-/-}$ mice (n=5 per group). (q) Working model showing how metabolic reprogramming by the SNO-CoA/SCoR system protects against kidney injury. Results are presented as mean±SD. One-way ANOVA with Tukey post hoc was used to detect significance in FIG. 4a-g. Two-tailed Student's t-test was used to detect significance in FIGS. 4i-k, 4m and 4n-p. * P<0.05, **P<0.01.
Figure 4B:
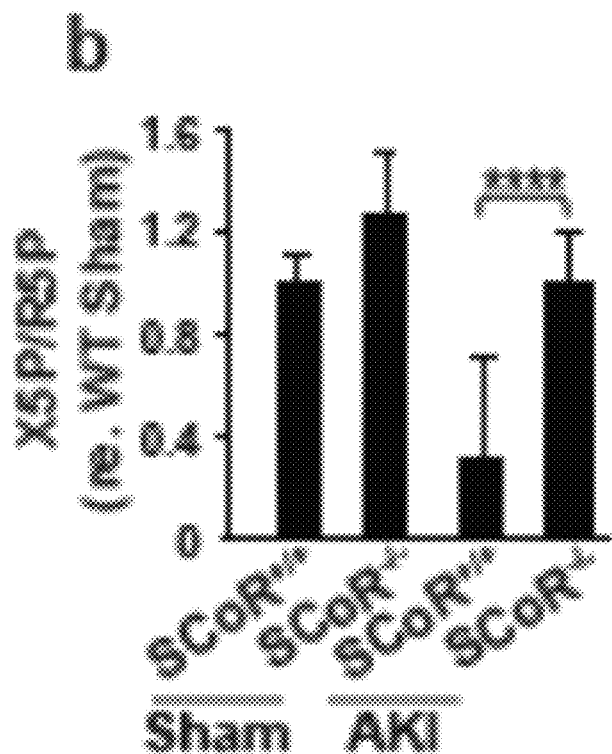
Figure 4C:
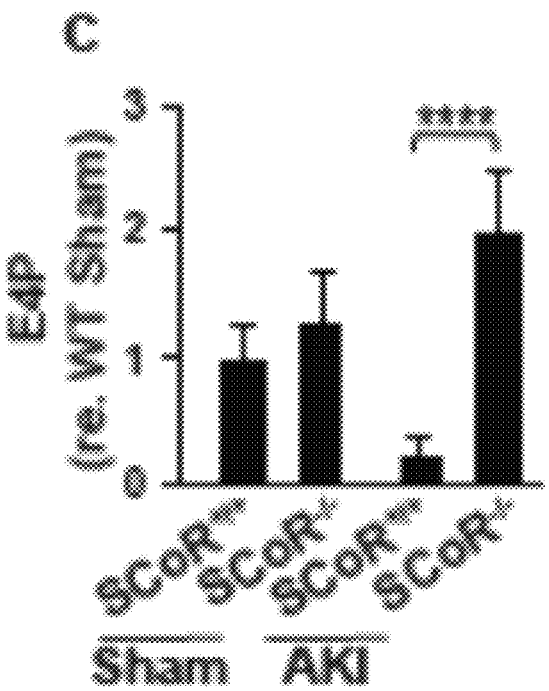
Figure 4E:
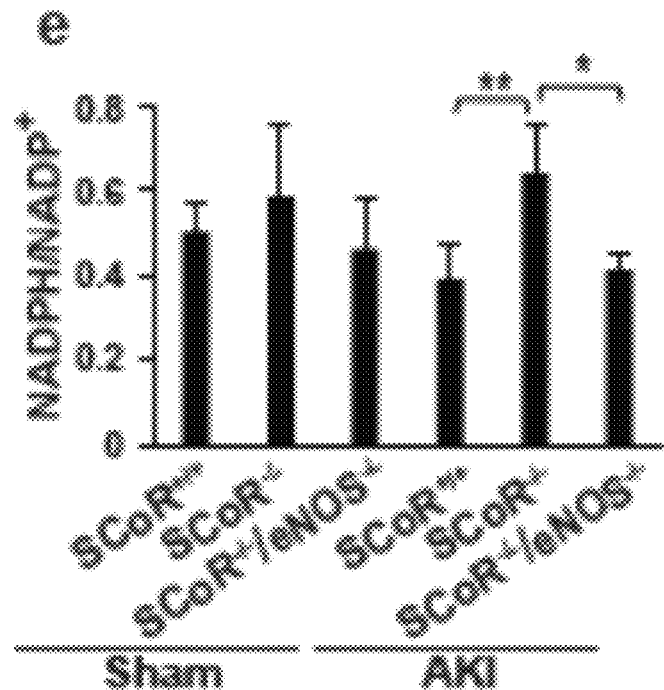
Figure 4D:
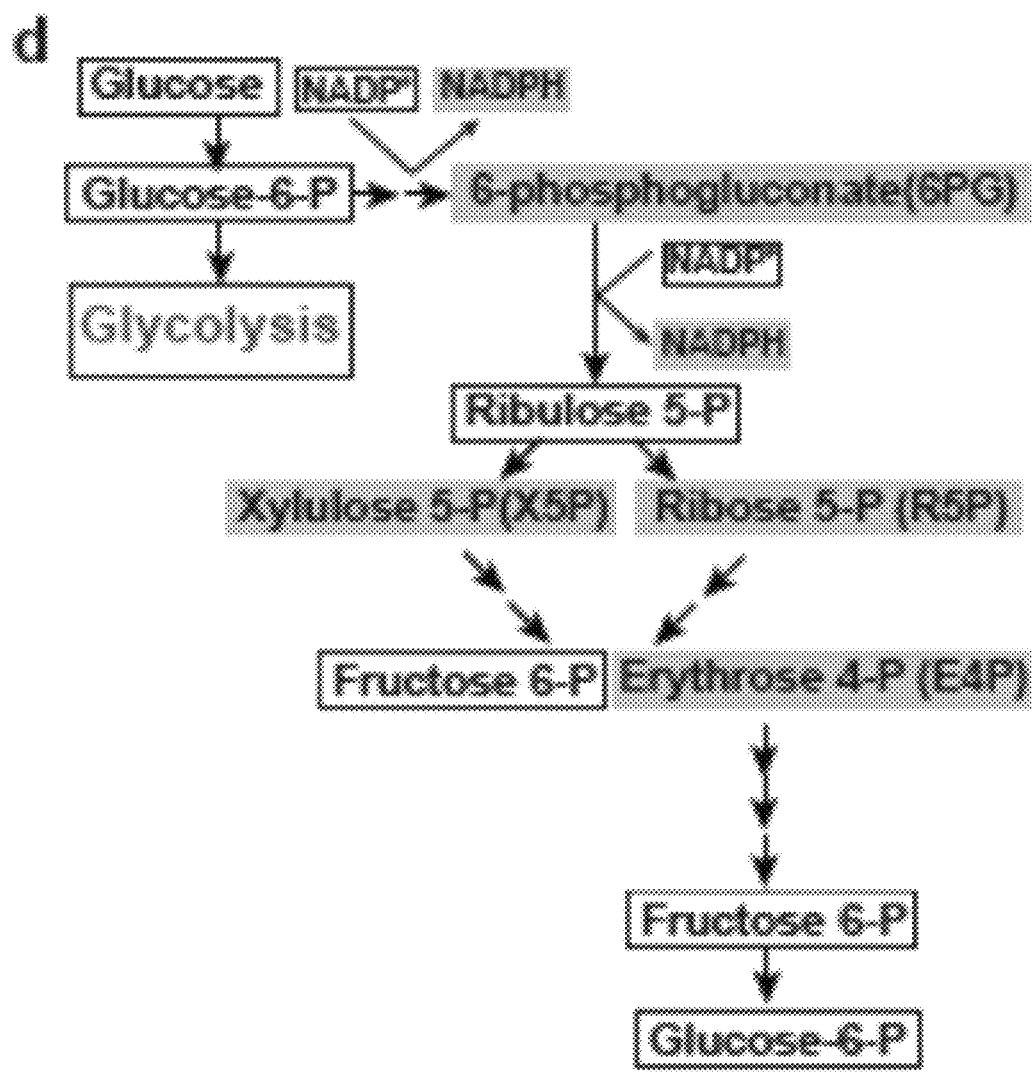
Figure 11D:
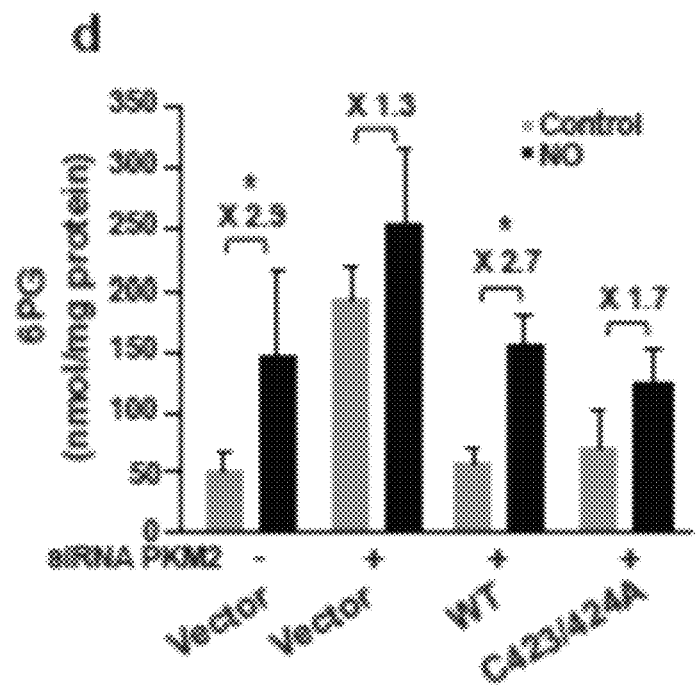
Figure 11E:
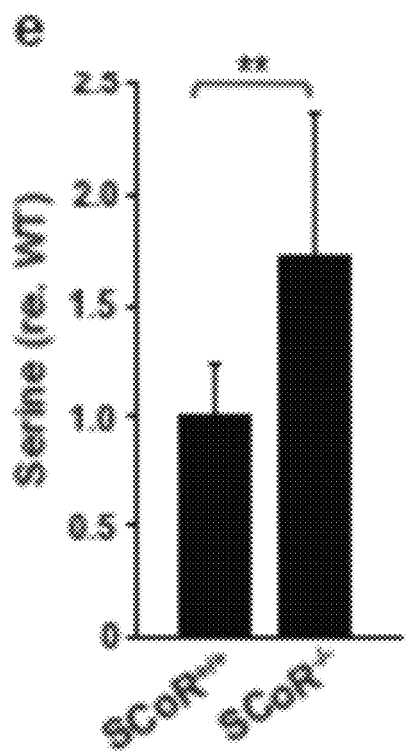
Figure 11F:
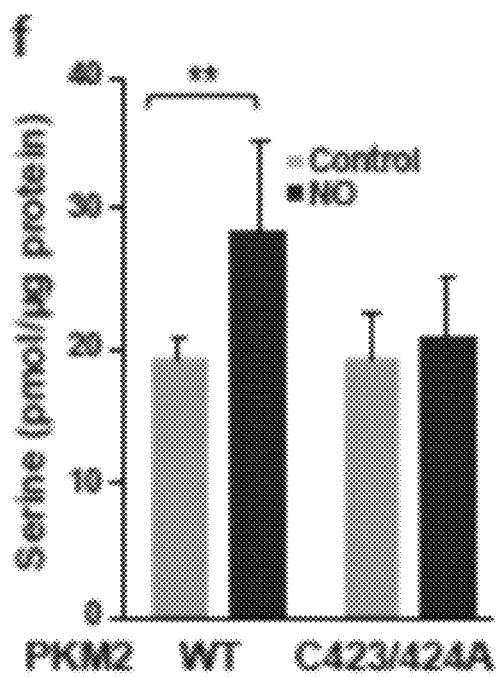

We wondered how inhibition of a terminal step in glycolysis could confer protection against AKI. We noted that multiple pentose phosphate pathway (PPP)-related intermediates, including 6-phosphogluconate, erythrose-4-phosphate, xylulose 5-P and ribose 5-P, were increased in $SCoR^{-/-}$ kidneys following AKI (FIGS. 4a-d). We also found that NO promotes accumulation of 6-phosphogluconate in Myc-PKM2-WT vs. Myc-PKM2-C423/424A cells (FIG. 11d). PPP is a metabolic pathway for generating NADPH, which can increase glutathione (GSH) and activate anti-oxidant enzymes, lessening kidney injury, and we confirmed that the NADPH/NADP+ ratio following AKI was significantly higher in kidneys of $SCoR^{-/-}$ mice vs. $SCoR^{+/+}$ or $SCoR^{-/-}/eNOS^{-/-}$ mice (FIG. 4e). Thus, inhibitory S-nitrosylation of PKM2 increases flux through the PPP.

Figure 4F:
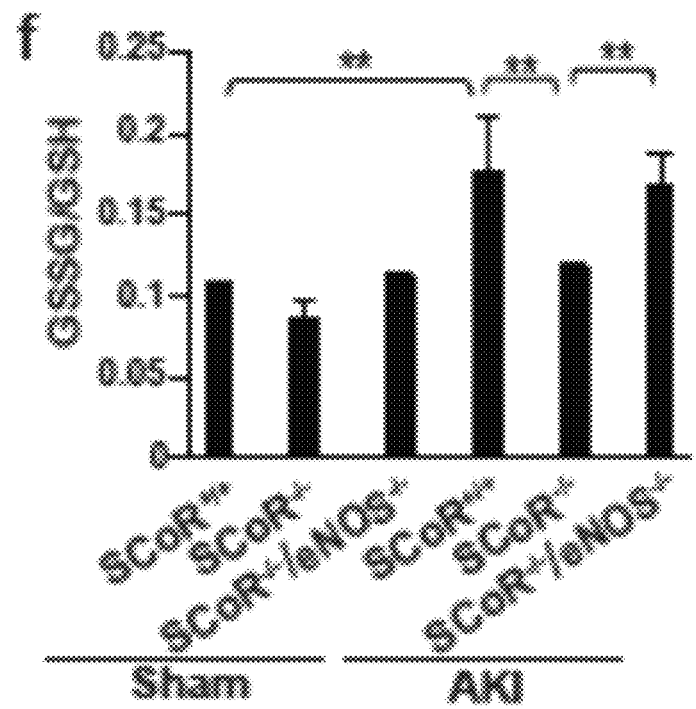
Figure 4G:
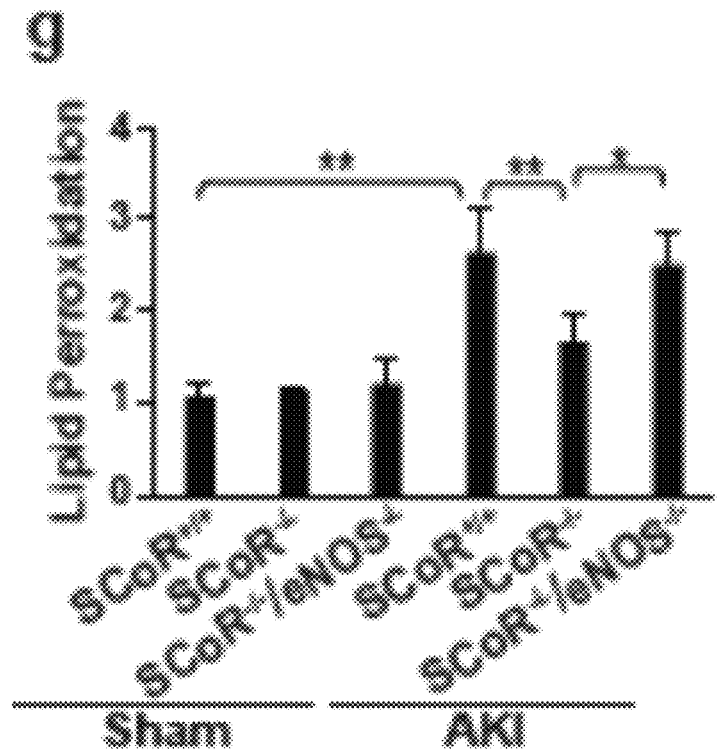

Reactive oxygen species (ROS) are central mediators of AKI, and enhancement of antioxidant defenses can ameliorate AKI. Tissue indicators of oxidative stress, GSSG/GSH ratio and lipid peroxidation, were lower in injured kidneys of $SCoR^{-/-}$ mice than in $SCoR^{+/+}$ or $SCoR^{-/-}/eNOS^{-/-}$ mice (FIGS. 4f & g) (without change in total GSH; Extended Data FIG. 7c). ROS levels may reflect mitochondrial dysfunction. However, levels of multiple TCA cycle intermediates (aconitate, isocitrate, succinate, fumarate, malate) were similar in AKI-injured $SCoAR^{-/-}$ mice and $SCoAR^{+/+}$ mice, and the ADP/ATP ratio was also no different between Myc-PKM2-WT and Myc-PKM2-C423/424A cells under NO treatment (FIG. 12). Thus, we conclude that inhibition of PKM2 by the SNO-CoA/SCoR system shunts metabolic intermediates through the PPP to alleviate oxidative stress and protect against AKI.

Figure 4H:
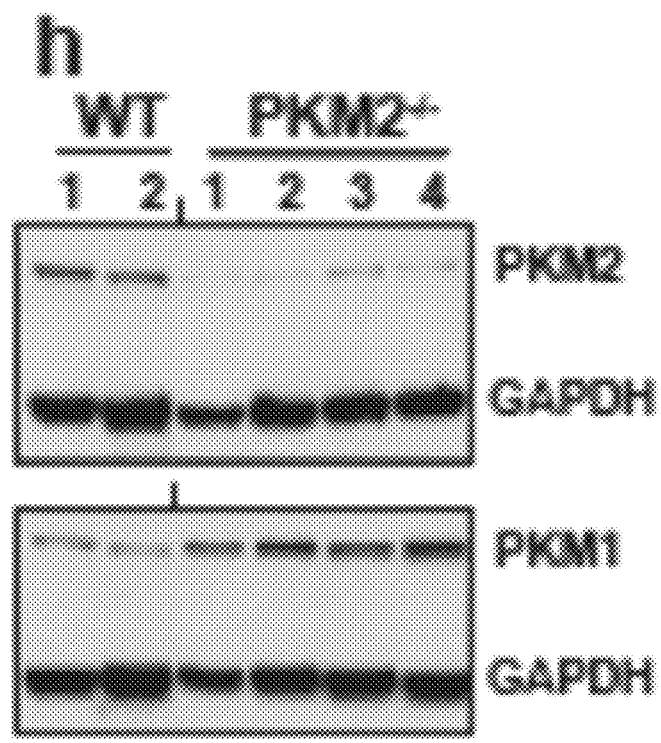
Figure 4H:
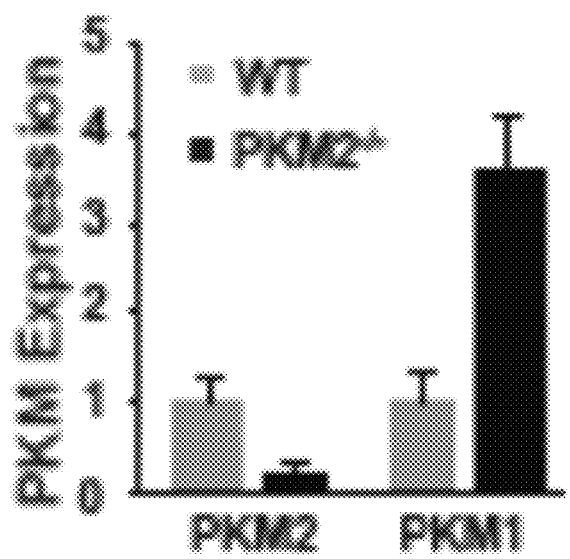
Figure 4I:
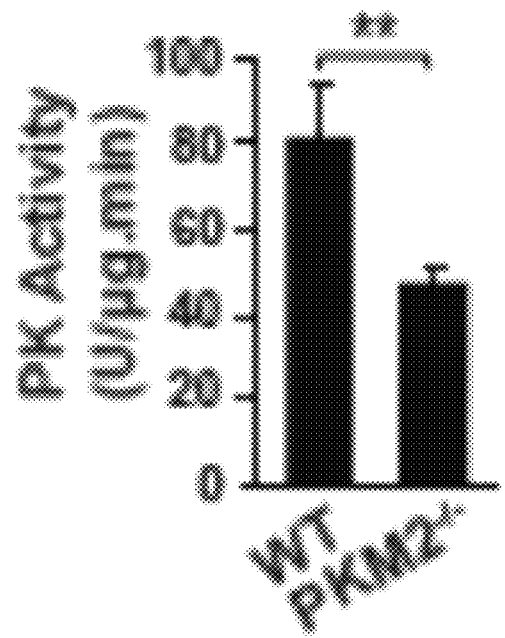
Figure 4J:
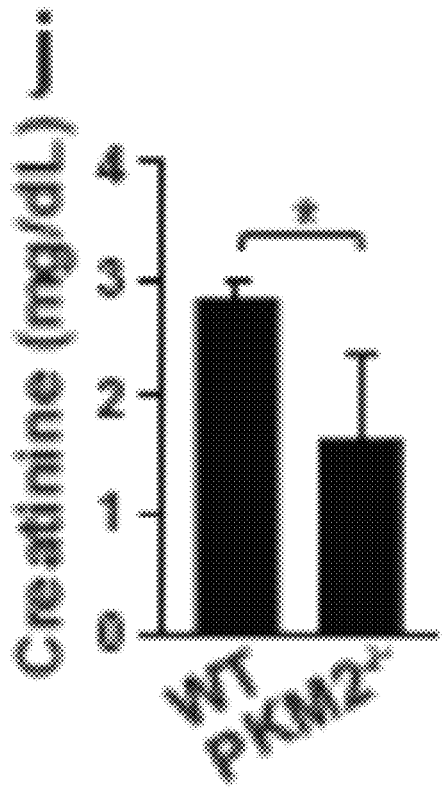
Figure 4K:
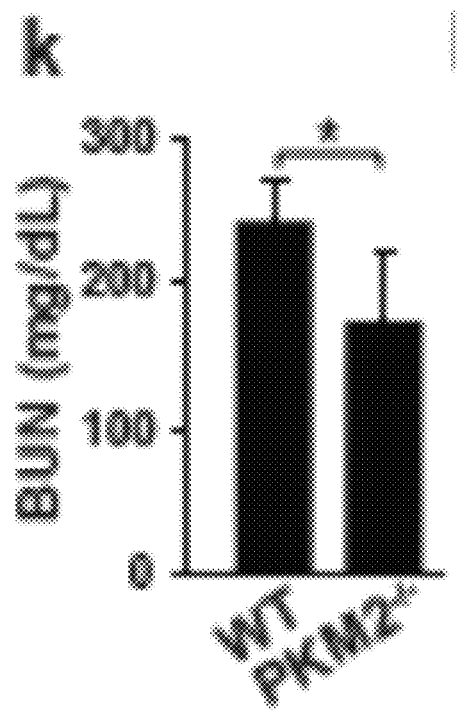
Figure 4L:
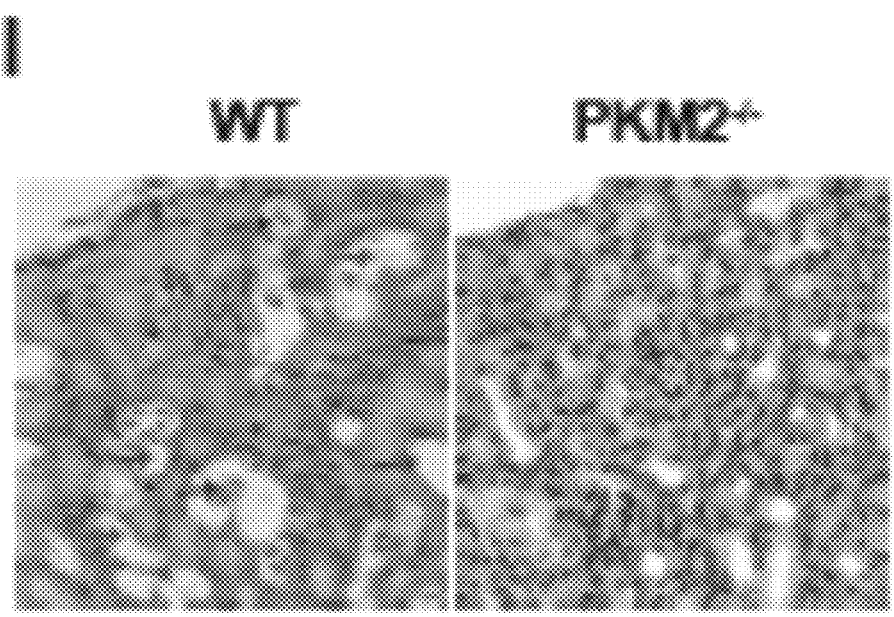
Figure 4M:
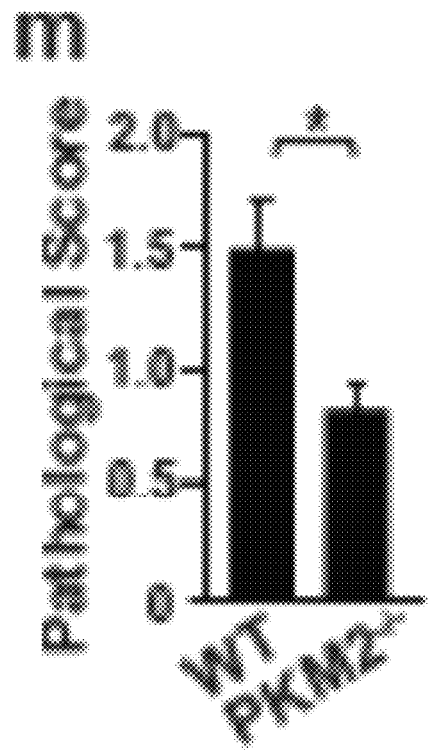
Figure 4N:
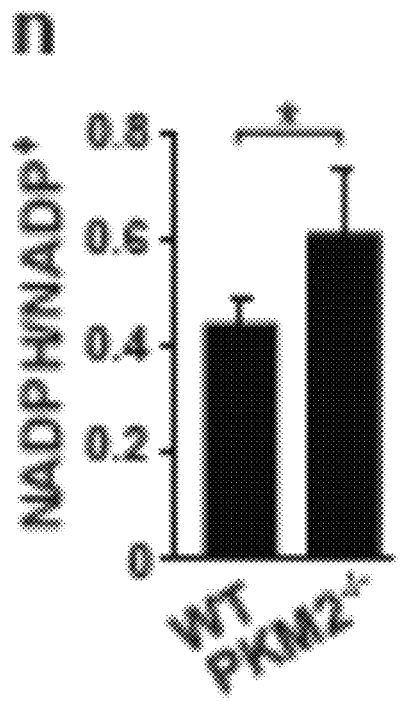
Figure 4O:
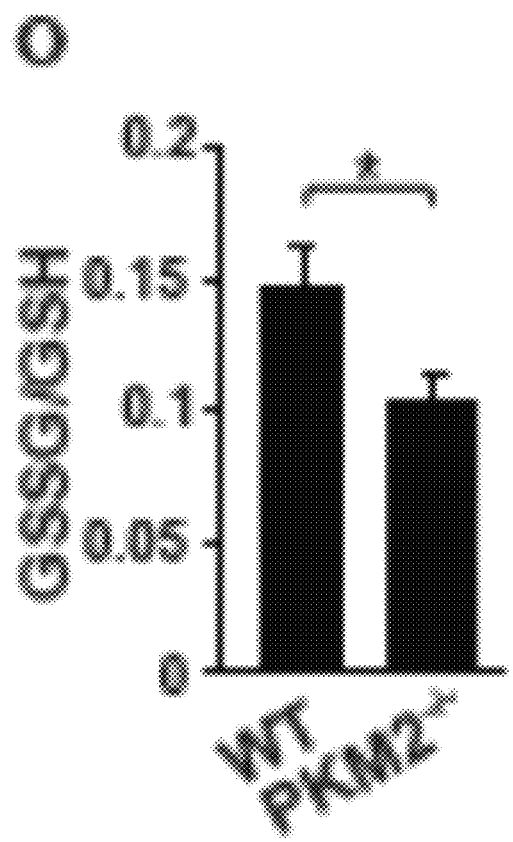
Figure 4P:
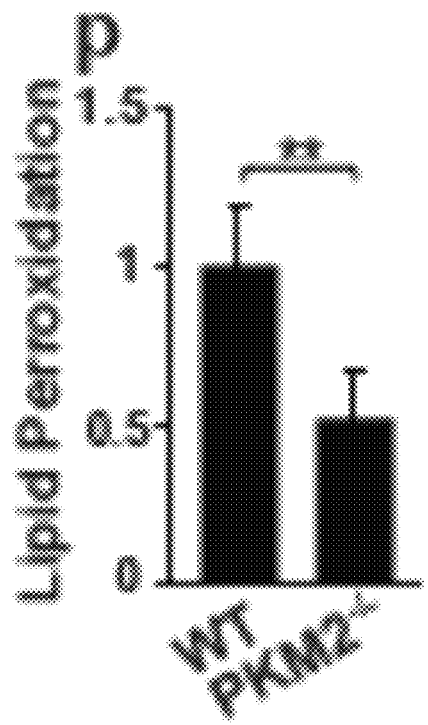
Figure 13A:
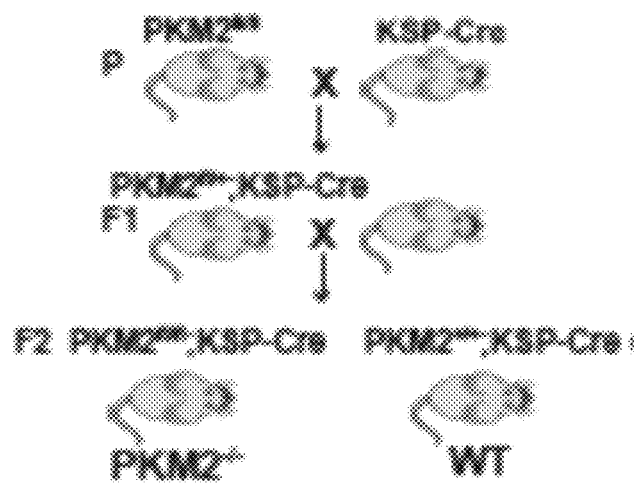
FIGS. 13(*a-d*) illustrate: (a) Schema illustrating generation of renal epithelial cell-specific PKM2$^{-/-}$ mice. (b) Survival curve following AKI (23 WT mice; 20 PKM2$^{-/-}$ mice). Survival was analyzed by Kaplan-Meier estimation using the SAS program. P=0.0413 for the Wilcoxon test. (c) Phosphoenolpyruvate (PEP) in injured kidneys of WT vs. PKM2$^{-/-}$ mice (n=5 per group). (d) Pyruvate in injured kidneys of WT vs. PKM2$^{-/-}$ mice (n=5 per group). Results in FIGS. 9C and 9D are presented as mean±SD. Two-tailed Student's t-test was used to detect significance. *P<0.05.
Figure 13B:
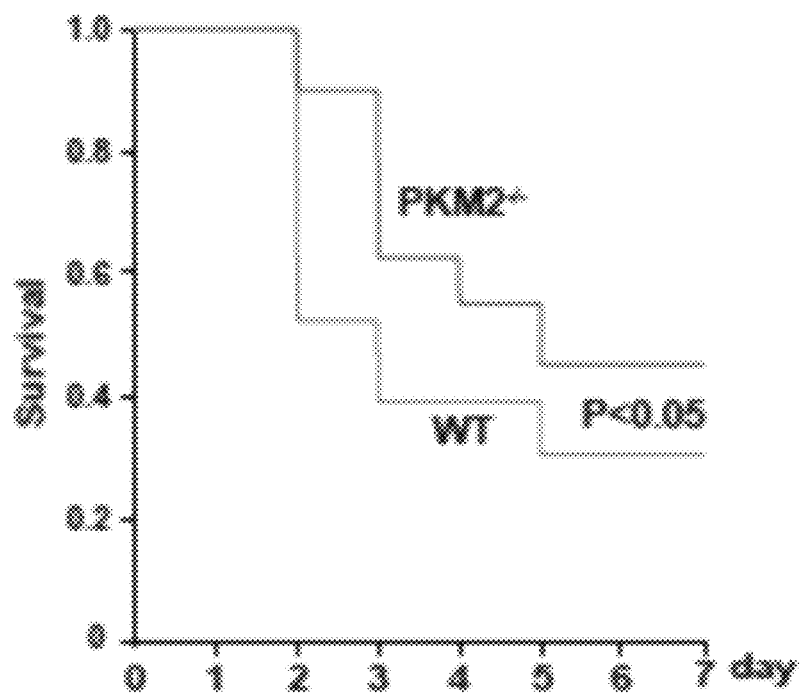
Figure 13C:
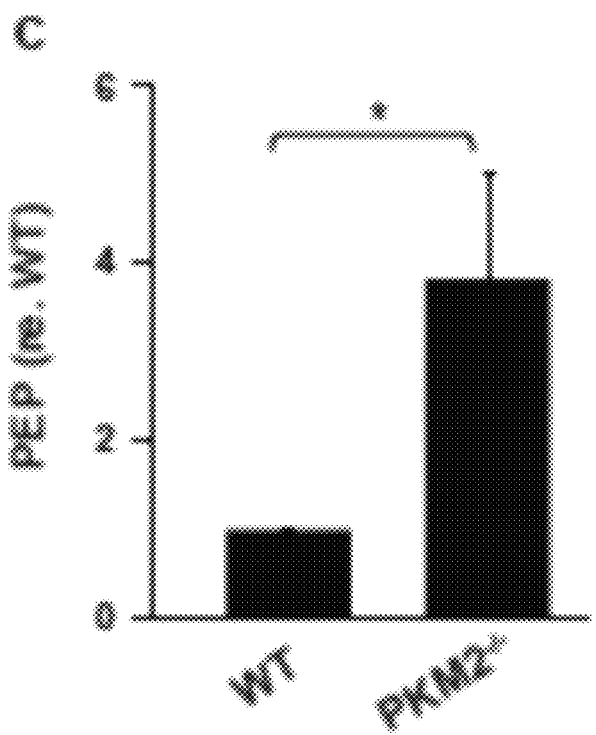
Figure 13D:
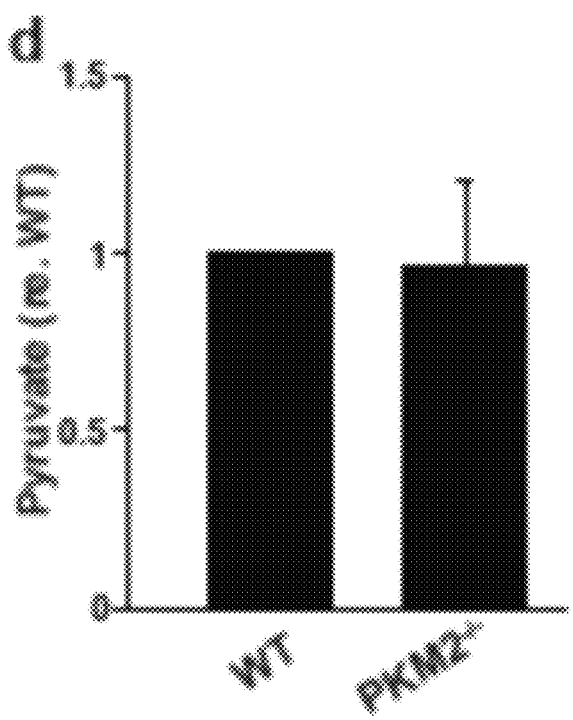

To establish conclusively the importance of PKM2 inhibition in protection against AKI and of metabolic reprogramming (PPP versus glycolytic flux) in renoprotection, we generated renal tubular epithelial cell-specific PKM2-knockout mice (PKM2fl/fl; KSP-Cre or $PKM2^{-/-}$) by crossing conditional PKM2-knockout mice (PKM2fl/fl) with KSP-Cre mice (FIG. 13a). Levels of PKM2 were markedly reduced in kidneys of $PKM2^{-/-}$ mice; however, levels of PKM1 were increased compensatorily (FIG. 4H). Overall, pyruvate kinase activity in the kidney was reduced by about 40%, which recapitulates precisely PKM activity in the injured kidneys of $SCoR^{-/-}$ mice (FIGS. 3c & 4i). Seram creatinine and BUN were significantly lower in $PKM2^{-/-}$ mice than in WT mice (FIGS. 4j & k) following PR-induced AKI, indicative of renoprotection. Histology showed that tubular injury was attenuated in $PKM2^{-/-}$ mice vs. WT mice (FIGS. 4l & m). Knockout of PKM2 improved survival by Kaplan-Meier estimation (FIG. 13b). NADPH/NADP+ ratio and PEP levels, but not pyruvate levels, were increased in $PKM2^{-/-}$ mice vs. WT mice (FIG. 4n) (FIGS. 13c & d). The GSSG/GSH ratio and lipid peroxidation was lower in injured kidneys of $PKM2^{-/-}$ mice than in WT mice (FIGS. 4o & p). These results confirm that function-regulated inhibition of PKM2 can shift metabolic flux from energy-generating (glycolytic) to anti-oxidant (PPP) pathways to protect kidneys from AKI.

Figure 4Q:
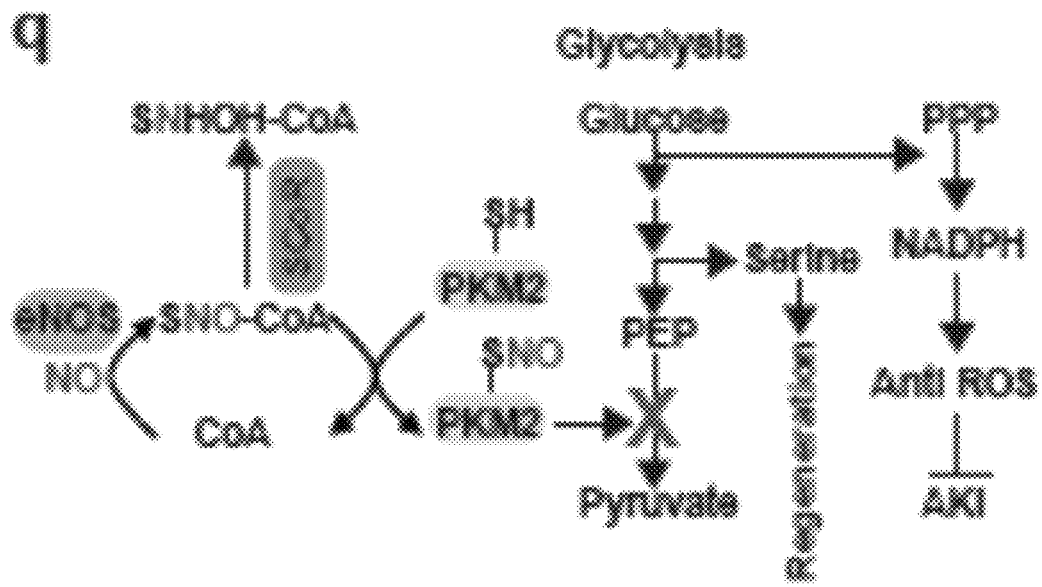

Our results establish an essential role for SNO-CoA in metabolic regulation. SNO-CoA serves as an endogenous source of NO groups and thus as a newly discovered mediator of protein S-nitrosylation, including of key metabolic enzymes. By coordinating metabolic flux through glycolysis versus PPP, the SNO-CoA/SCoR system regulates the balance between energy and reducing equivalents, and thereby protects against AKI (FIG. 4q). It has been reported that NO regulates glycolysis in neurons and glia, but the mechanism has remained unclear. Our findings thus raise the idea that SCoR-regulated, SNO-CoA-mediated protein S-nitrosylation may subserve metabolic signaling broadly.

SNO-CoA reductases are enzymes of previously unknown function that mediate the breakdown of SNO-CoA. Alcohol dehydrogenase gene 6 (ADH6) is the main SNO-CoA reductase in yeast, where it functions in microbial metabolism. However, ADH6 has no mammalian homologue. Our demonstration here that aldo-keto reductase family 1 member A1 (AKR1A1) has physiologically relevant SNO-CoA reductase activity in mammals establishes that SCoRs are functionally conserved across phylogeny. SCoRs operate as SNO-CoA-dependent denitrosylases, thereby regulating protein S-nitrosylation in both microbes and mammals.

Figure 11G:
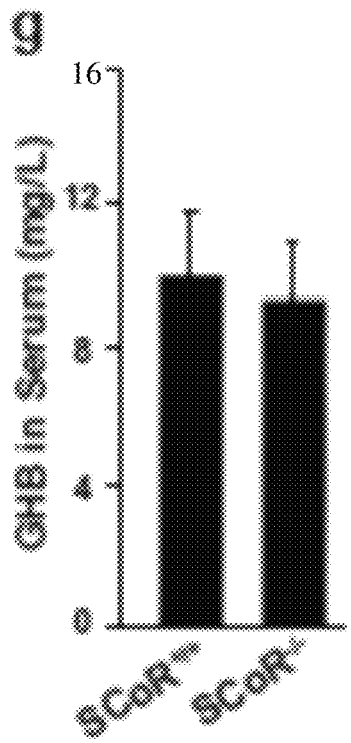
Figure 12A:
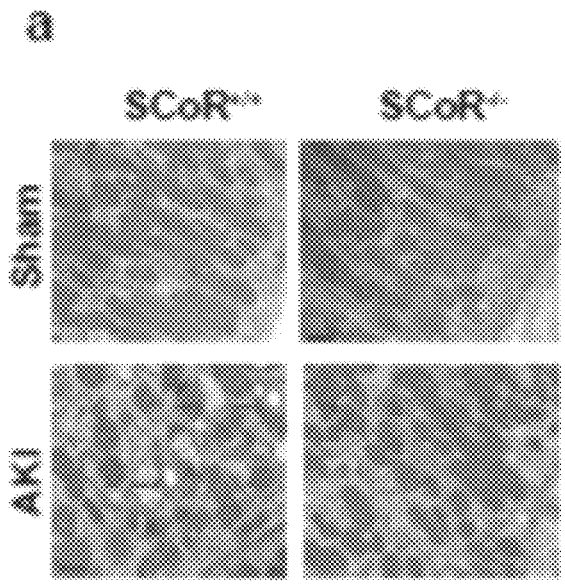
FIGS. 12(a-d) illustrate (a) mitochondrial morphology in tubular cells after sham operation and I/R injury as assessed by electron microscopy. Mitochondrial swelling is indicated by the red arrow. Scale bars, 200 nm. (b) Quantification of swollen mitochondria vs. total mitochondria in I/R-injured SCoR$^{+/+}$ vs. SCoR$^{-/-}$ mice. (c) The ratio of ADP vs. ATP in Myc-PKM2-WT and Myc-PKM2-C423/424A HEK cells after NO (DETANO; 500 µM) (n=4). (d) Amounts of multiple TCA cycle intermediates (aconitate, isocitrate, succinate, fumarate and malate) in sham-treated or injured kidneys of SCoR$^{+/+}$ vs. SCoR$^{-/-}$ mice (n=11 per group). Results are presented as mean±SD. One-way ANOVA with Tukey post hoc was used to detect significance in FIGS. 12*d* and 12*d*.
Figure 12B:
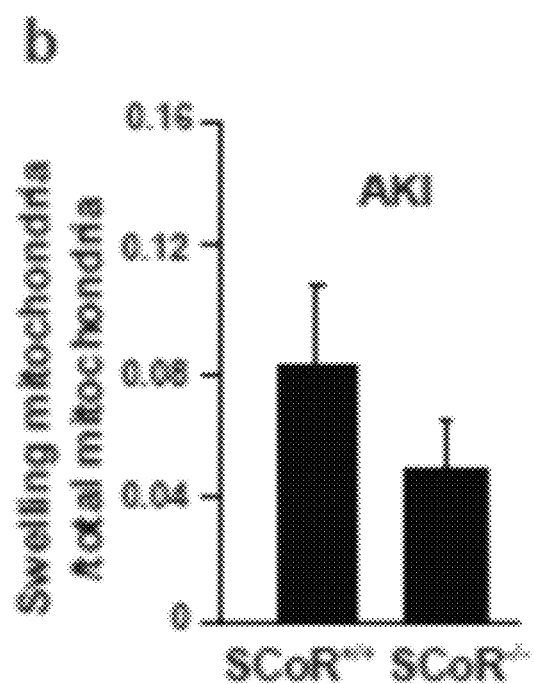
Figure 12C:
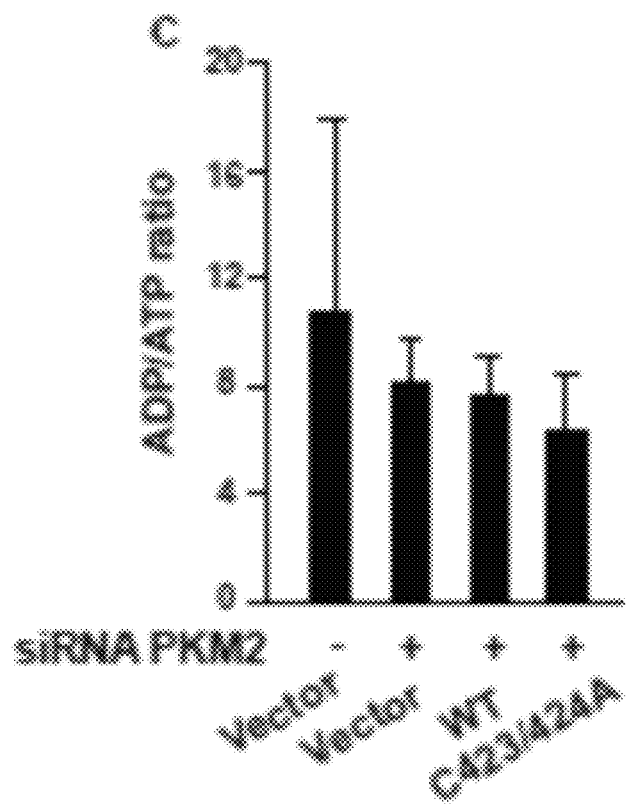
Figure 12D:
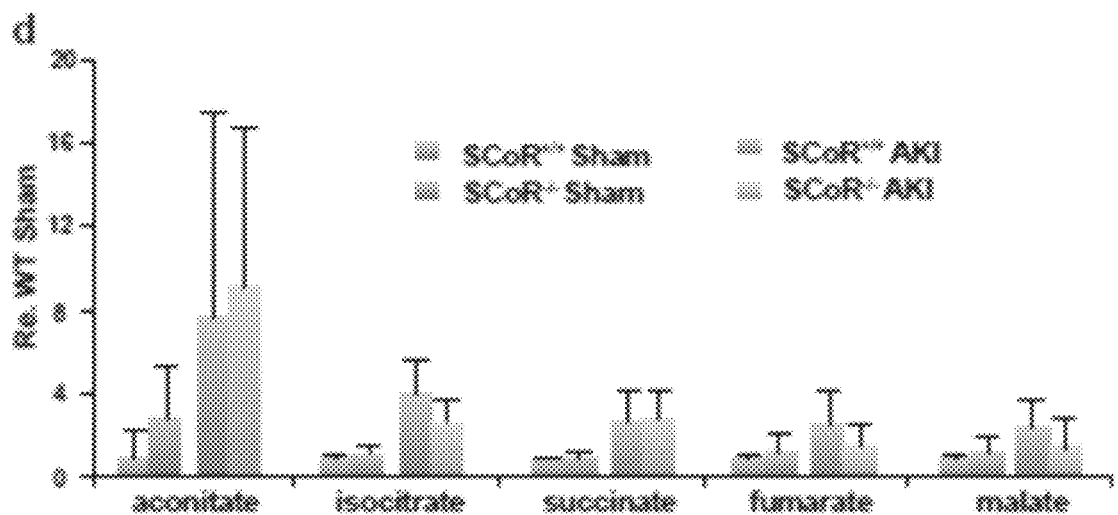

AKR1A1 has an essential role in ascorbic acid synthesis in rodents and activity against gamma-hydroxybutyric acid (GHB)-related aldehydes in vitro. But humans and yeast do not synthesize ascorbic acid and AKR1A1 does not regulate GHB in vivo (FIG. 11g). Therefore, the primary function of AKR1A (and Adh6) had been a mystery. Our work indicates that, as in yeast, the major function of AKR1A/SCoR in mammals is to regulate NO-based metabolic signaling. Notably eNOS-derived NO had been previously identified with both metabolic regulation and renoprotection, but the molecular mechanisms were poorly understood. Our new findings provide an unanticipated mechanistic basis for eNOS-derived NO protection in the kidney that is mediated by SNO-CoA and governed by SCoR (FIG. 4Q).

Figure 2K:
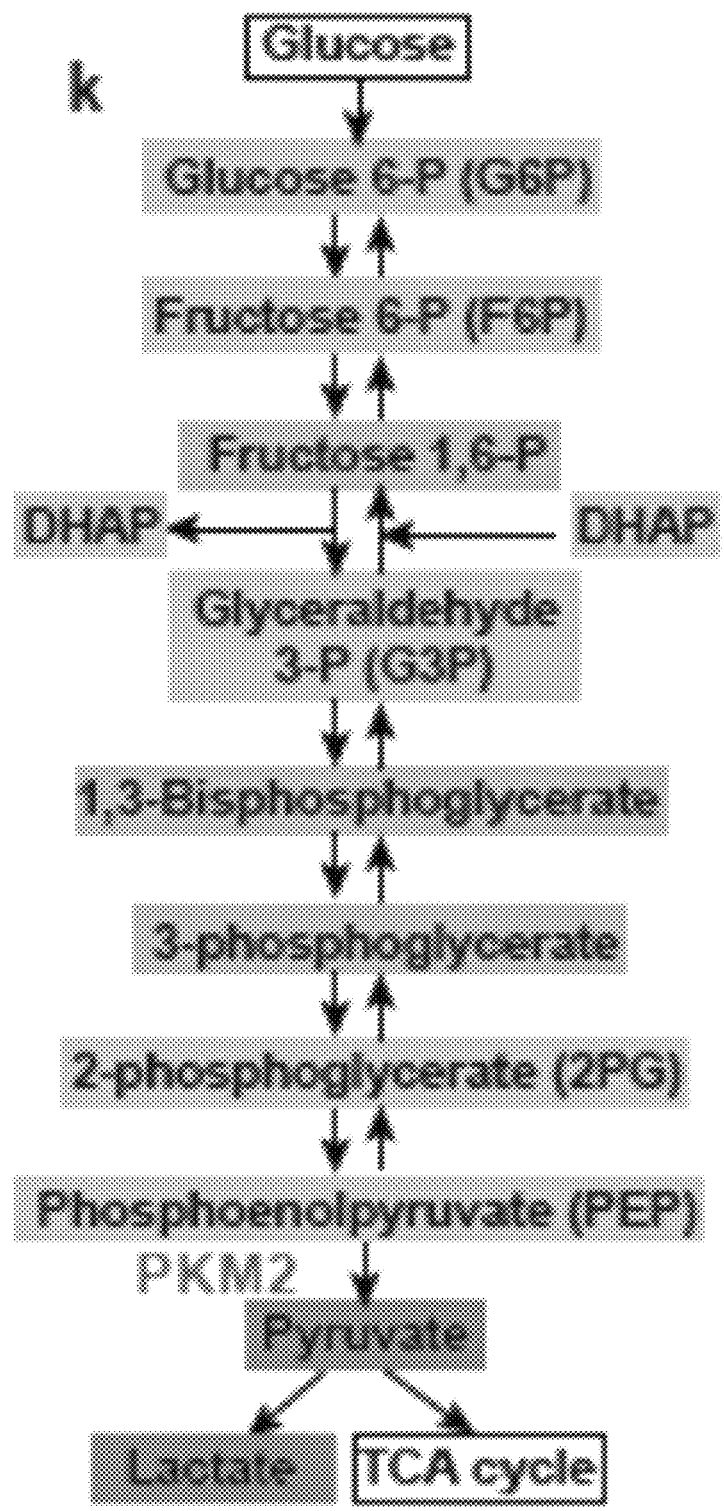
Figure 10A:
FIGS. 10(A-C) illustrate: (a) alternative splicing of PKM gene (PKM2 (SEQ ID NO: 1) and PKM1 (SEQ ID NO: 1)). C423 and C424 are encoded by PKM2-specific exon 10. (b) Ribbon structure of tetrameric PKM2 analyzed by MacPyMOL. Four pairs of C423 and C424 in tetrameric PKM2 are highlighted in red. (c) Expression of PKM1 and PKM2 in fifteen different mouse tissues.
Figure 10B:
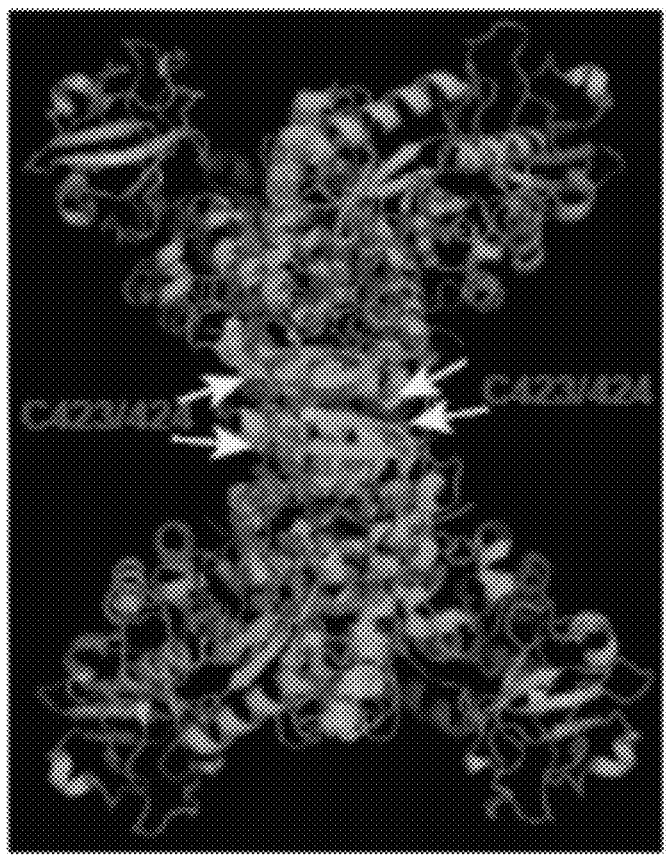
Figure 10C:
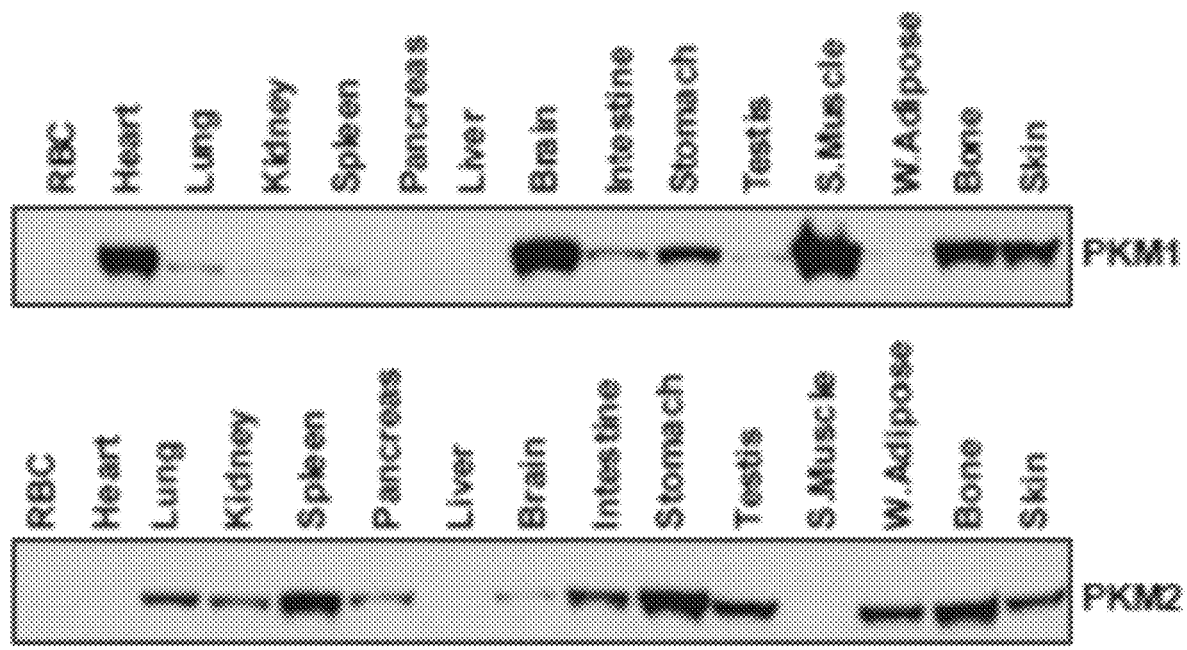
Figure 14A:
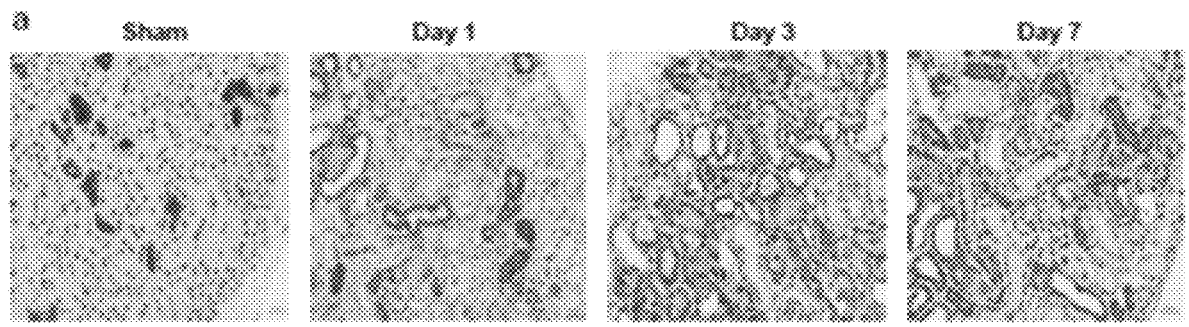
FIGS. 14(*a-c*) illustrate (a) Immunostaining showing expression of PKM2 in sham or AKI kidneys of WT mice. (b) Western blot showing expression of PKM2, PKM1 and PKLR in sham or AKI kidneys of WT mice. (c) Quantification of expression of PKM2, PKM1 and PKLR in (b) (n=3).
Figure 14B:
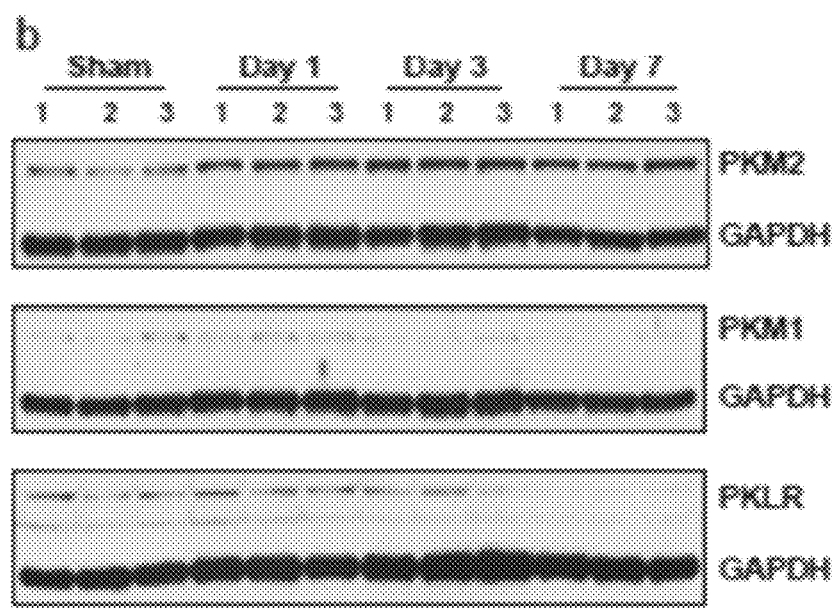
Figure 14C:
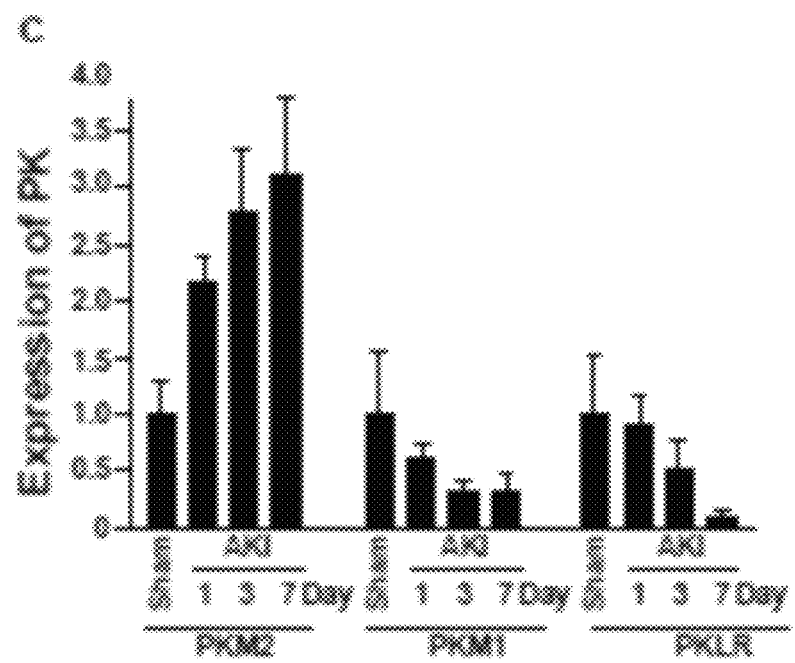

Pyruvate kinase isoforms (PKLR, PKM1 and PKM2) catalyze the last step in glycolysis (FIG. 2k). PKM1 is expressed in high energy-requiring organs including heart, muscle and brain (FIG. 10c) and forms a constitutively active tetramer, whereas PKM2 is expressed primarily in fetal (and tumor) cells, and can shift reversibly between tetramer and lower-activity dimer to program metabolism for growth or survival. Why PKM2 expresses in some differentiated tissues and predominantly after AKI (FIG. 14) has been unclear. We now show that PKM2 expression enables protection by metabolic reprogramming. S-nitrosylation of PKM2 by SNO-CoA forces glucose flux into the PPP to detoxify ROS (FIG. 4q). PKM2 inhibition also increases serine synthesis, which serves as a precursor for lipids, proteins and nucleotides, and indeed serine levels are elevated in SCoR$^{-/-}$ mice following AKI (FIGS. 7e & f). Therefore, an additional advantage of metabolic programming via PKM2 may be to regenerate tissues following injury. By contrast with reversible regulation of PKM2 in AKI, irreversible, longstanding PKM2 inactivation has been associated with diabetic nephropathy. Thus, inhibition of SCoR and/or PKM2 may be most advantageous therapeutically in acute injurious conditions including AKI.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, I claim:

1. A method for preventing or treating acute kidney injury associated with renal ischemia reperfusion injury in a subject in need thereof, the method comprising:
    administering to the subject a therapeutically effective amount of an AKR1A1 inhibitor in combination with nicotinamide adenine dinucleotide (NAD$^+$) and/or a NAD+ precursor, wherein the AKR1A1 inhibitor includes a compound selected from the group consisting of:

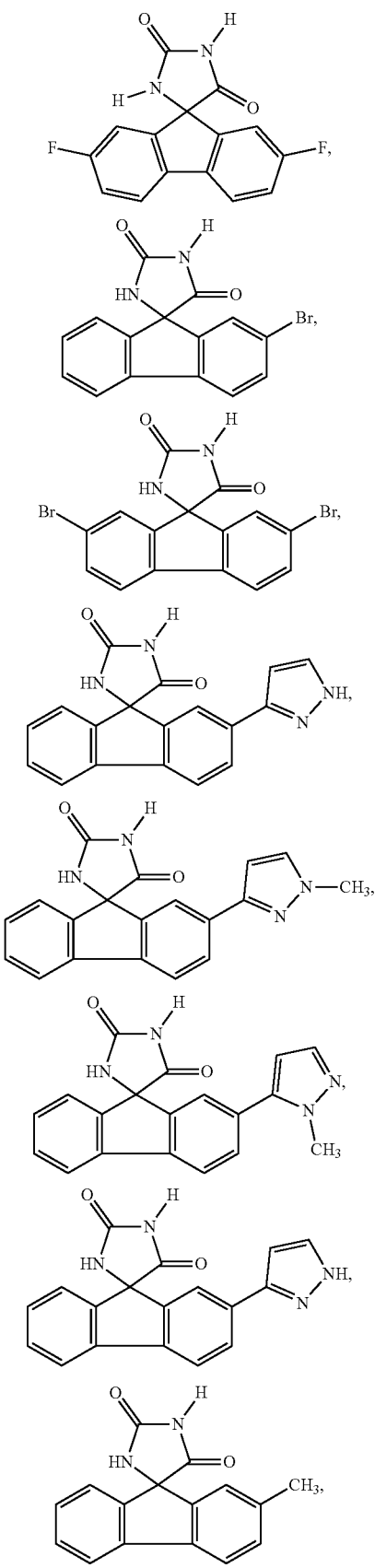

-continued
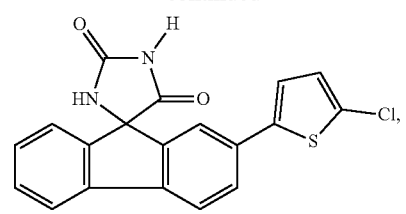
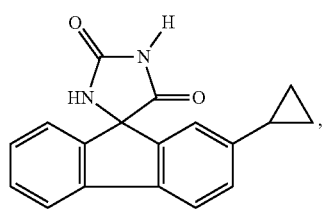
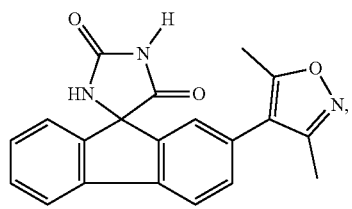
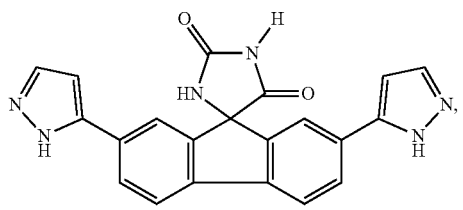
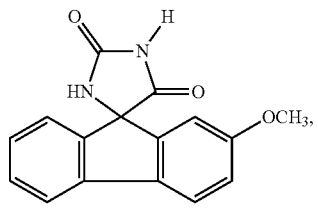
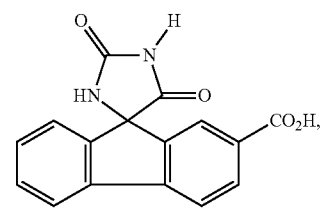
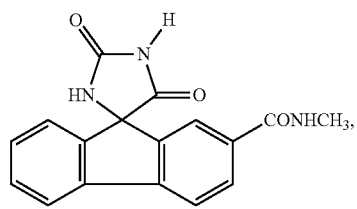
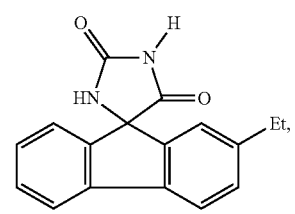
-continued
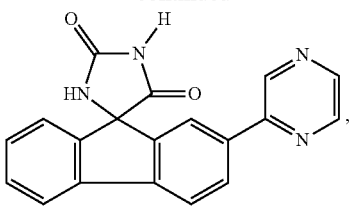
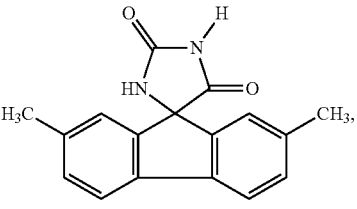
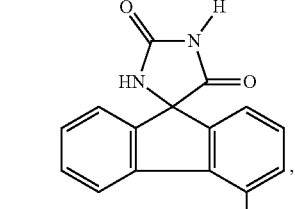
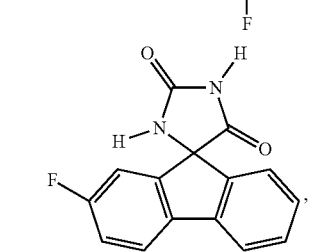
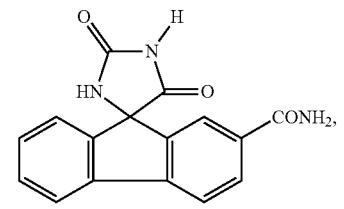
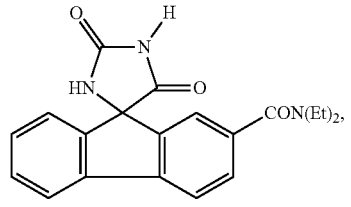
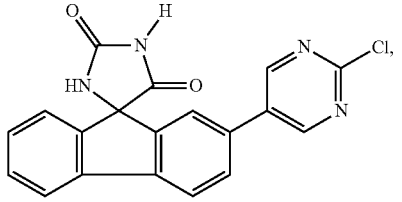
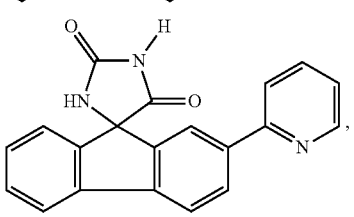

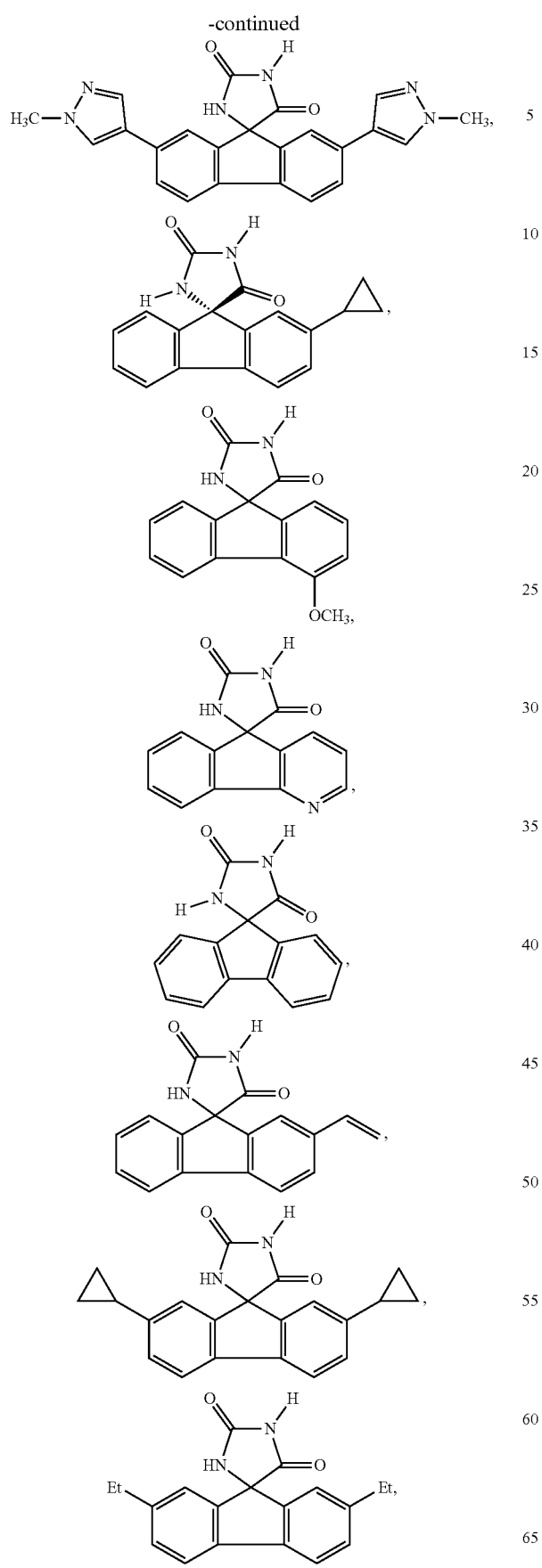
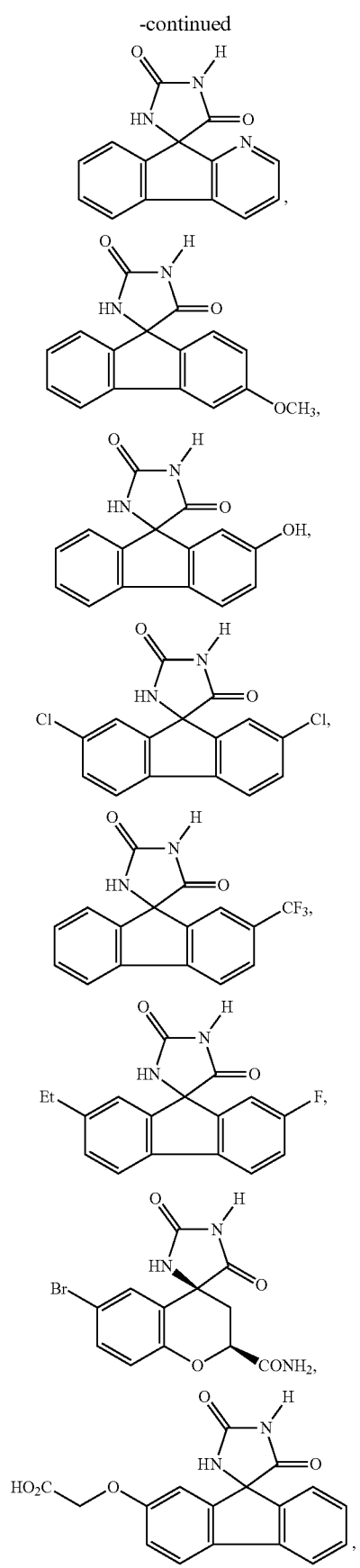

77
-continued
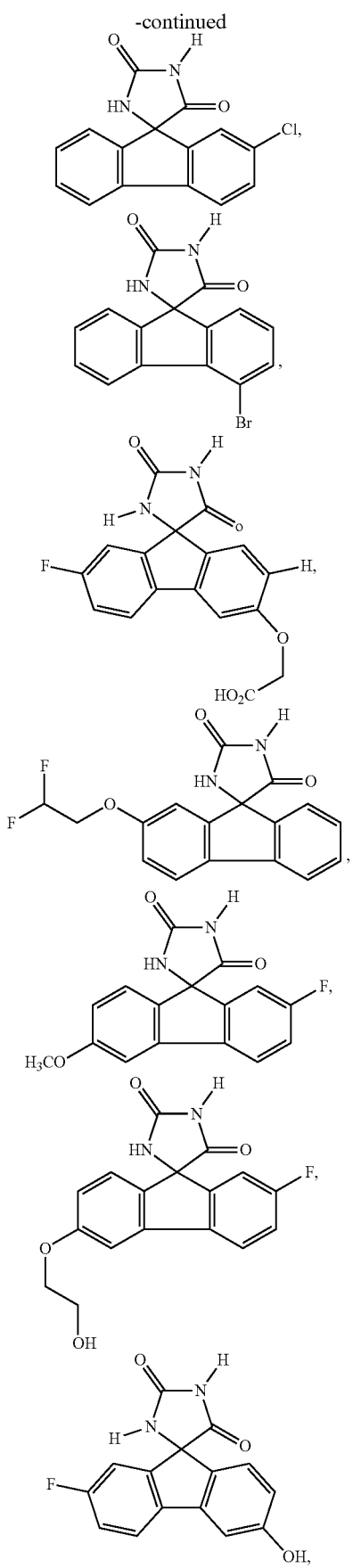
78
-continued
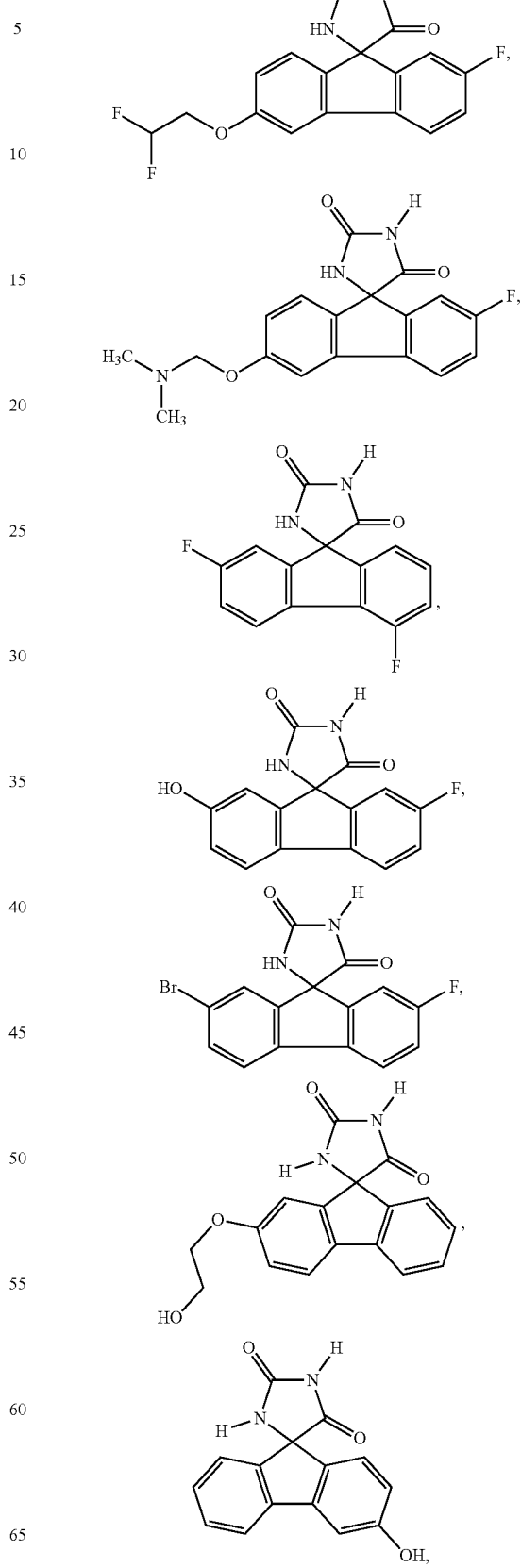

79
-continued
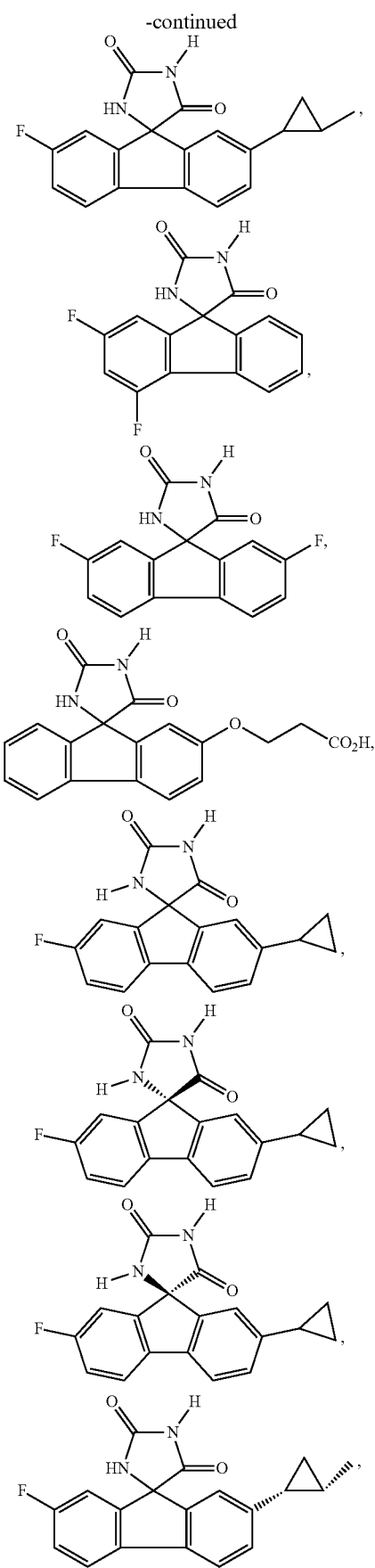
80
-continued
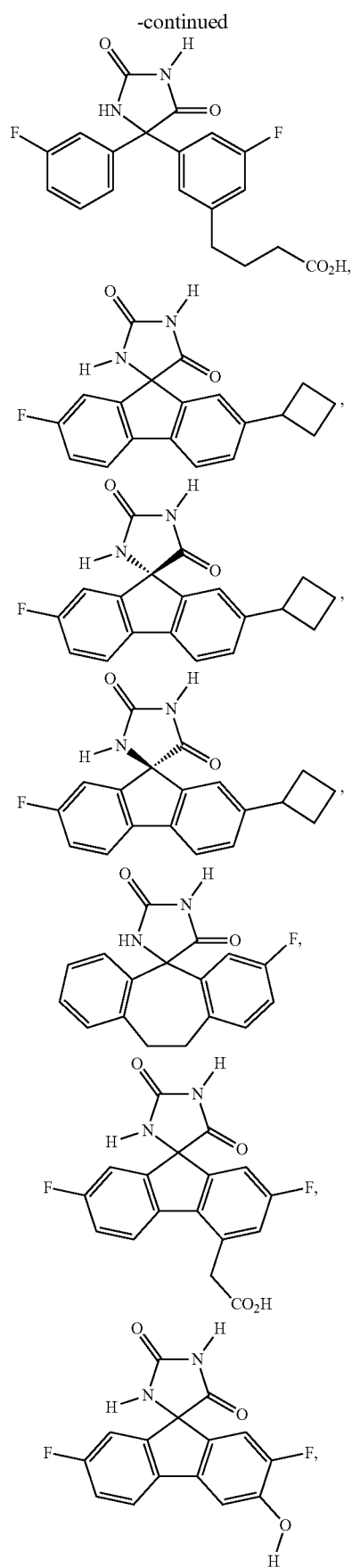

81
-continued
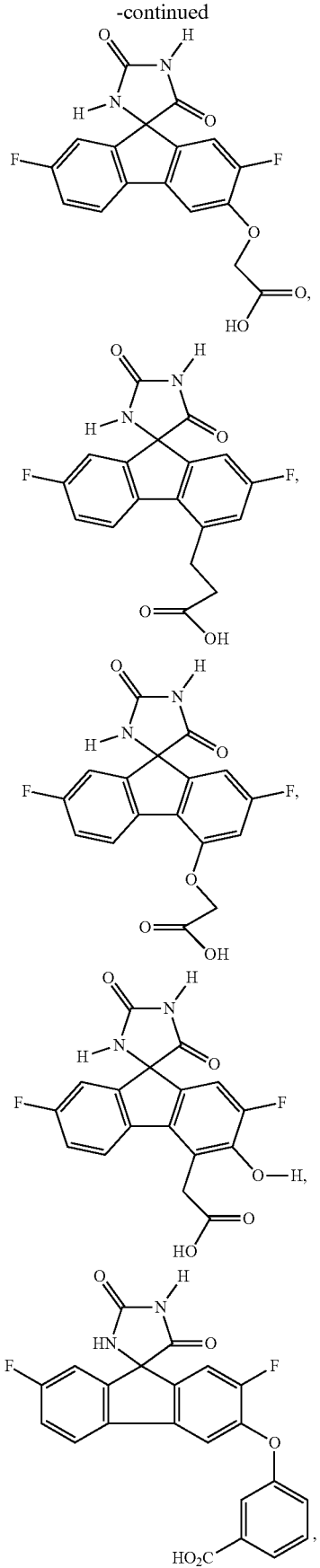
82
-continued
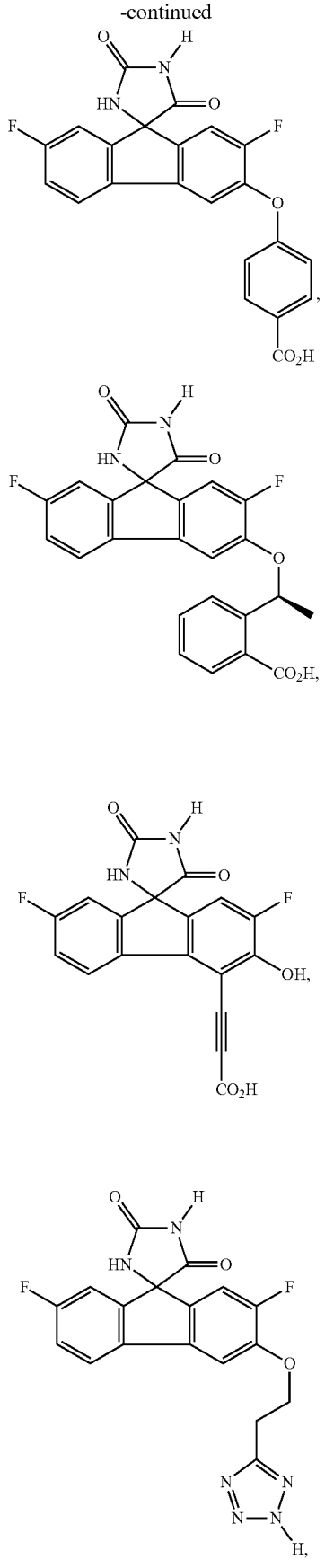

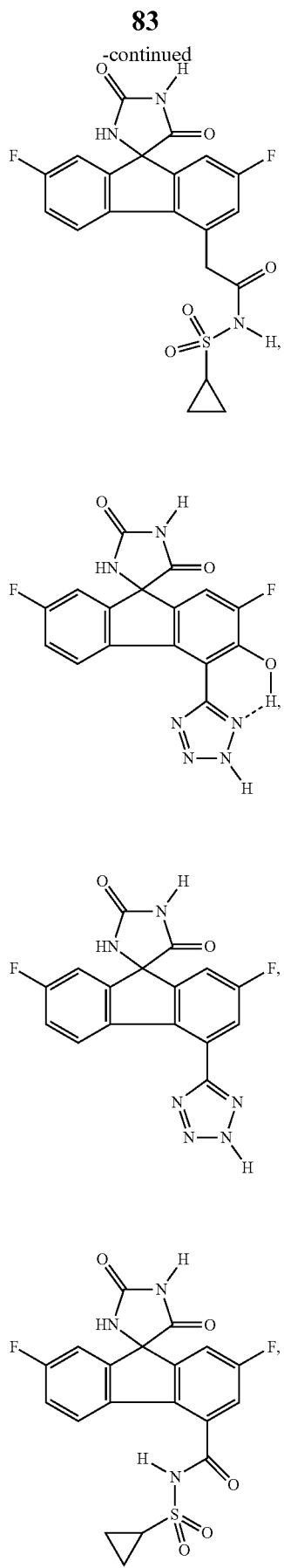
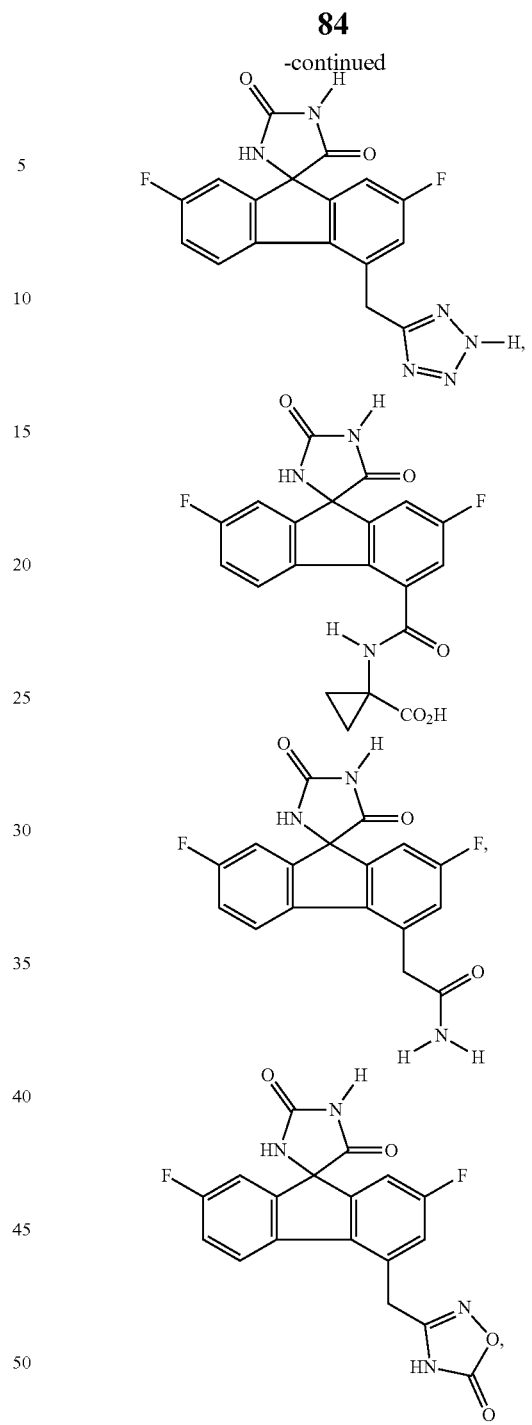

and pharmaceutically acceptable salts thereof.

2. The method of claim 1, wherein the amount of AKR1A1 inhibitor administered to the subject is an amount effective to induce renal vasodilatation, enhance resistance to hypoxia, improve renal hemodynamics, decrease renal oxidative stress, reduce renal inflammation, and/or preserve renal function.

3. The method of claim 1, wherein the AKR1A1 inhibitor is administered before and/or after the ischemia reperfusion injury.

4. The method of claim 1, wherein the AKR1A1 inhibitor is administered at a range of about 1 minute to about 72 hours before the ischemia reperfusion injury.

5. The method of claim 1, wherein the is administered at at least about 2 hours before the ischemia reperfusion injury.

6. The method of claim 1, wherein the AKR1A1 inhibitor is administered at least about 30 minutes after the ischemic reperfusion injury.

7. The method of claim 1, wherein the renal ischemia reperfusion injury is associated with a kidney transplant in the subject.

8. The method of claim 1, wherein the AKR1A1 inhibitor is administered at an amount(s) effective to promote S-nitrosylation of proteins in the subject.

9. The method of claim 1, wherein the AKR1A1 inhibitor has a selectivity for AKR1A1 versus AKR1B1≥2 or more times.

10. The method of claim 1, wherein a selective or partially selective AKR1A1 inhibitor is administered in combination with a selective or partially selective AKR1B1 inhibitor.

11. The method of claim 10, wherein the AKR1B1 inhibitor has a selectivity for AKR1B1 versus AKR1A1≥2 or more times.

12. The method of claim 1, wherein the NAD+ precursor is selected from the group consisting of tryptophan, nicotinic acid, nicotinic acid riboside, nicotinamide riboside (NR), and nicotinamide (NAM).

* * * * *